United States Patent
Stephenson et al.

(10) Patent No.: US 11,634,389 B2
(45) Date of Patent: Apr. 25, 2023

(54) SUCCINATE DEHYDROGENASE INHIBITORS AND METHODS OF MAKING AND USING THE SAME

(71) Applicant: THE REGENTS OF THE UNIVERSITY OF MICHIGAN, Ann Arbor, MI (US)

(72) Inventors: Corey Stephenson, Ann Arbor, MI (US); Daryl Staveness, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/281,687

(22) PCT Filed: Nov. 13, 2019

(86) PCT No.: PCT/US2019/061303
§ 371 (c)(1),
(2) Date: Mar. 31, 2021

(87) PCT Pub. No.: WO2020/112357
PCT Pub. Date: Jun. 4, 2020

(65) Prior Publication Data
US 2022/0002252 A1   Jan. 6, 2022

Related U.S. Application Data

(60) Provisional application No. 62/772,302, filed on Nov. 28, 2018.

(51) Int. Cl.
| | |
|---|---|
| C07D 231/14 | (2006.01) |
| C07D 231/16 | (2006.01) |
| C07D 401/12 | (2006.01) |
| C07D 409/12 | (2006.01) |
| A01P 3/00 | (2006.01) |
| A01N 43/56 | (2006.01) |

(52) U.S. Cl.
CPC .......... *C07D 231/14* (2013.01); *A01N 43/56* (2013.01); *A01P 3/00* (2021.08); *C07D 231/16* (2013.01); *C07D 401/12* (2013.01); *C07D 409/12* (2013.01)

(58) Field of Classification Search
CPC ................ C07D 231/14; C07D 231/16; C07D 401/12; C07D 409/12
See application file for complete search history.

(56) References Cited

U.S. PATENT DOCUMENTS

| RE39,991 E | 1/2008 | Ricks et al. |
| 2012/0195857 A1 | 8/2012 | Belema et al. |
| 2015/0079028 A1 | 3/2015 | Zhang et al. |

FOREIGN PATENT DOCUMENTS

| WO | WO-2006/016708 A1 | 2/2006 |
| WO | WO-2013/167545 A1 | 11/2013 |
| WO | WO-2018/108977 A1 | 6/2018 |
| WO | WO-2018/109002 A1 | 6/2018 |

OTHER PUBLICATIONS

Applequist et al., Displacement reactions at bridgeheads of bridged polycarbocyclic systems, Chem. Rev., 54:1065-85 (1954).
Beresford, Succinate dehydrogenase inhibitor (SDHI) fungicide resistance prevention strategy, published online at: <https://resistance.nzpps.org/index.php?p=fungicides/sdhi> (Aug. 2011).
International Application No. PCT/US2019/061303, International Search Report and Written Opinion, dated Feb. 14, 2020.
McKay et al., Succinate Dehydrogenase Inhibitor (SDHI) Fungicide Resistance Prevention Strategy, New Zealand Plant Protection 64 (Jan. 8, 2011): 119-124.
Pubchem. CID 138272, Mar. 27, 2005, pp. 1-16, Retrieved from the Internet <URL: https://pubchem.ncbi.nlm.nih.gov/compound/138272>: p. 2, formula.
Staveness et al., Providing a New Aniline Bioisostere through the Photochemical Production of 1-Aminonorbornanes, Chem., 5(1):215-26 (Jan. 2019).
Succinate dehydrogenase, Wikipedia, published online at: <https://en.wikipedia.org/wiki/Succinate_dehydrogenase> (last edited Jan. 21, 2021).
Walter et al., Sedaxane, Isopyrazam and Solatenol: Novel Broad-spectrum Fungicides Inhibiting Succinate Dehydrogenase (SDH)—Synthesis Challenges and Biological Aspects, Chimia, 69:425-34 (2015).
Wilt et al., The preparation and study of some 1-norbornenyl and norbornenyl-1-carbinyl derivatives, J. Org. Chem., 33:694-708 (1968).
Xiong et al., Succinate Dehydrogenase: An Ideal Target for Fungicide Discovery, IN: Maienfisch et al. (eds.), Discovery and Synthesis of Crop Protection Products, American Chemical Society, Chapter 13, pp. 175-194 (2015).
Yao et al., Discovery of Novel Succinate Dehydrogenase Inhibitors by the Integration of in Silico Library Design and Pharmacophore Mapping, J. Agricultural and Food Chemistry, 65:3204-11 (2017).

*Primary Examiner* — Shawquia Jackson
(74) *Attorney, Agent, or Firm* — Marshall, Gerstein & Borun LLP

(57) ABSTRACT

Provided herein are compounds of Formula (I), including methods of making the same. The disclosed compounds are succinate dehydrogenase inhibitors and can be useful in, e.g., inhibiting or preventing fungal growth.

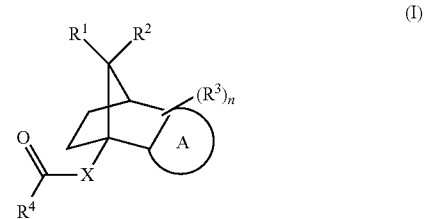

19 Claims, 6 Drawing Sheets

SUCCINATE DEHYDROGENASE INHIBITORS AND METHODS OF MAKING AND USING THE SAME

CROSS REFERENCE TO RELATED APPLICATIONS

This application is the U.S. National phase of International Patent Application No. PCT/US19/61303 filed Nov. 13, 2019, which in turn claims the priority benefit of U.S. Provisional Application 62/772,302 filed on Nov. 28, 2018, the respective disclosures of which are hereby incorporated by reference in their entireties.

BACKGROUND

Agrochemicals are chemical products that are used in agriculture to improve crop yields or quantity. These chemicals can be divided into two major classes: fertilizers and pesticides. Fertilizers promote crop growth by providing nutrients necessary for plant health and can also include hormones and other growth-promoting agents. Pesticides are used to prevent crop damage from harmful organisms such as insects, fungi, nematodes, and other plants.

Fungicides are a specific class of agrochemical that controls the growth of fungi and fungal spores, which may otherwise cause damage to crops and significantly reduce yield or quantity. Fungicides can be classified based on the mode of action within the crop being treated. For example, contact fungicides are sprayed on the plant and kill surface-attached fungi, but provide no protection to internal plant tissues. Translaminar fungicides can be redistributed from the upper sprayed leaf surface to the underside, unsprayed surface of the leaf. Systemic fungicides are absorbed by the plant and redistributed throughout the entire organism through xylem vessels.

Succinate dehydrogenase (SDH), also known as Complex II, is an enzyme complex found in many species of bacteria and in the inner mitochondrial membrane of eukaryotes. It is the only enzyme involved in both the citric acid cycle and the electron transport chain, which makes it a unique component of cellular respiration and ATP production. Inhibitors of SDH (SDHIs) are potent fungicides and have been used as crop protecting agrochemicals since the first SDHI, carboxin, was discovered in the early 1960s. SDH inhibitors can have contact, translaminar, or systemic modes of action depending upon the crop being treated and the pathogen being targeted.

Pyrazole carboxamides are an important class of SDHI fungicides. Minor substitutions on the core of the small molecule can dramatically affect the spectrum of organisms the molecule can treat. Examples of recently developed pyrazole-carboxamide SDHI fungicides include sedaxane, isopyrazam, and benzovindiflupyr. However, due to the ability of fungi to develop resistance to various classes of fungicides, new molecules may be useful in mitigating the rise of fungicide-resistant organisms.

SUMMARY

Provided herein are compounds having a structure of Formula (I):

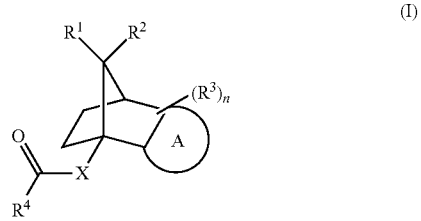

wherein:

X is NH or O;

ring A is $C_{6-10}$ aryl or 5-12 membered heteroaryl having 1-3 ring heteroatoms selected from N, O, and S;

each of $R^1$ and $R^2$ is independently selected from H, halo, $C_{1-18}$ alkyl, $C_{2-18}$ alkenyl, $C_{2-18}$ alkynyl, $C_{1-18}$ alkoxy, $C_{1-18}$ haloalkyl, $C_{1-18}$ hydroxyalkyl, C(O)NHC$_{1-18}$alkyl, C(O)OC$_{1-18}$alkyl, C(O)SC$_{1-18}$alkyl, $C_{2-18}$ heteroalkyl having 1-3 backbone heteroatoms selected from N, O, and S, $C_{6-10}$ aryl, or 5-8 membered heteroaryl having 1-3 ring heteroatoms selected from N, O, and S; or $R^1$ and $R^2$ together form $C_{2-6}$ alkene, $C_{3-8}$ cycloalkyl, or $C_{3-8}$ heterocycloalkyl having 1-3 ring heteroatoms selected from N, O, and S, optionally substituted with 1-3 $R^3$ groups;

each $R^3$ is independently halo, CN, OH, $NO_2$, $C_{1-6}$ alkoxy, $C_{1-6}$ alkyl, $C_{1-6}$ hydroxyalkyl, $C_{1-6}$ haloalkyl, or $C_{1-6}$ haloalkylene-OH $R^4$ is $C_{2-6}$ alkyl, $C_{1-6}$ haloalkyl, $C_{1-6}$ heteroalkyl having 1-3 backbone heteroatoms selected from N, O, and S, $C_{3-8}$ cycloalkyl, $C_{6-10}$ aryl, 3-12 membered heterocycloalkyl having 1-3 ring heteroatoms selected from N, O, and S, or 5-12 membered heteroaryl having 1-3 ring heteroatoms selected from N, O, and S, and the aryl or heteroaryl group is optionally substituted with 1-3 $R^3$ groups; and n is 0, 1, 2, or 3;

with the proviso that if ring A is $C_6$ aryl, n is 0, and $R^1$ and $R^2$ are each H, then $R^4$ is not unsubstituted phenyl.

Also provided are methods of inhibiting or preventing fungal growth on a plant, comprising applying to the plant a compound as disclosed herein.

Further provided are methods of preparing a compound having a structure of Formula (I) comprising irradiating a compound of formula (II) to form an intermediate of formula (III):

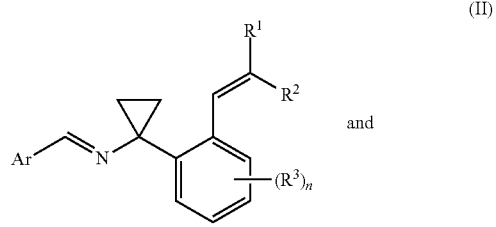

and

-continued

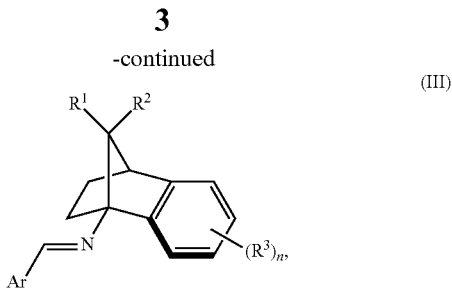

(III)

wherein Ar comprises a $C_6$ aryl.

Further aspects and advantages will be apparent to those of ordinary skill in the art from a review of the following detailed description. The description hereafter includes specific embodiments with the understanding that the disclosure is illustrative and is not intended to limit the invention to the specific embodiments described herein.

BRIEF DESCRIPTION OF THE DRAWINGS

FIG. 9 illustrates the mean number of diseased kernels of a summer wheat varietal inoculated with *Fusarium graminearum* when various compounds according to the disclosure were applied to the plant 4 hours prior to inoculation.

FIG. 10 illustrates the mean number of diseased kernels of a summer wheat varietal inoculated with *Fusarium graminearum* when various compounds according to the disclosure were applied to the plant 24 hours after inoculation.

DETAILED DESCRIPTION

Figure 1:
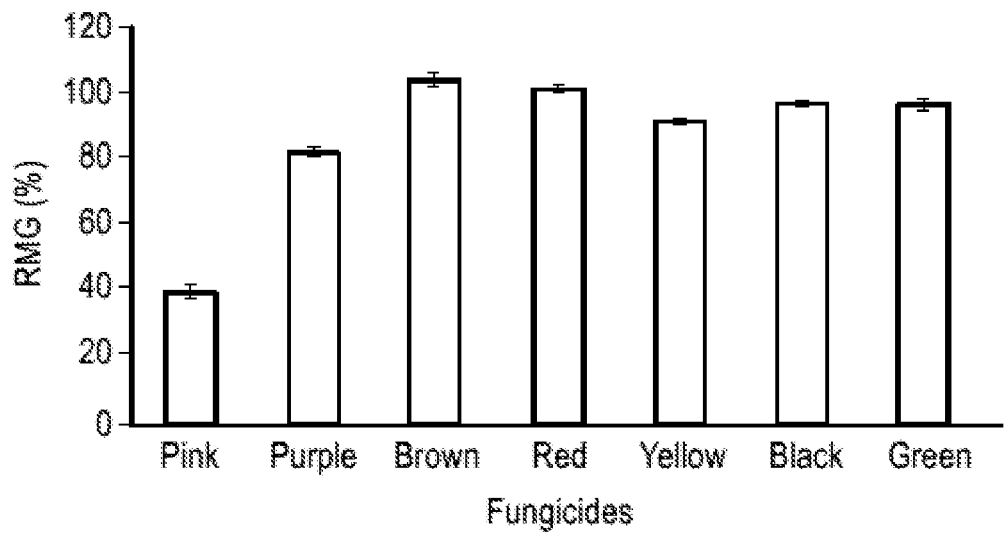
FIG. 1 illustrates the fungicidal performance of various compounds according to the disclosure against *Sclerotinia sclerotiorum* isolate. RMG (%) indicates the normalized radial mycelial growth.
Figure 2:
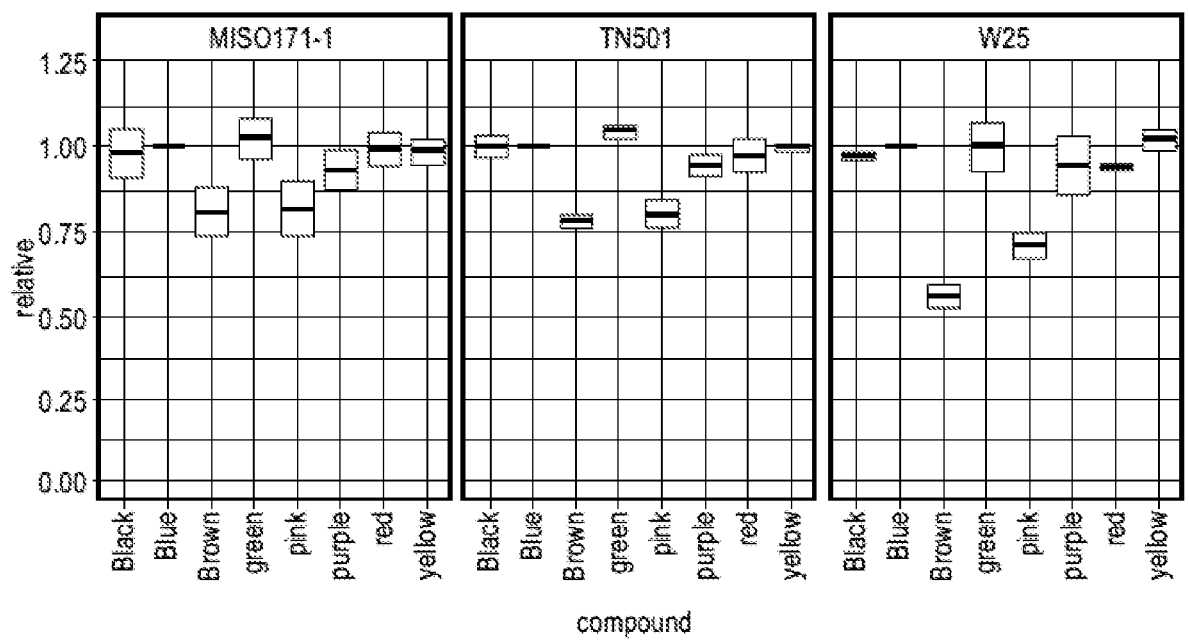
FIG. 2 illustrates the fungicidal performance of various compounds according to the disclosure against *Macrophomina phaseolina* isolates (e.g., MISO17101, TN501, and W25). "Relative" indicates the normalized percent radial mycelial growth.
Figure 3:
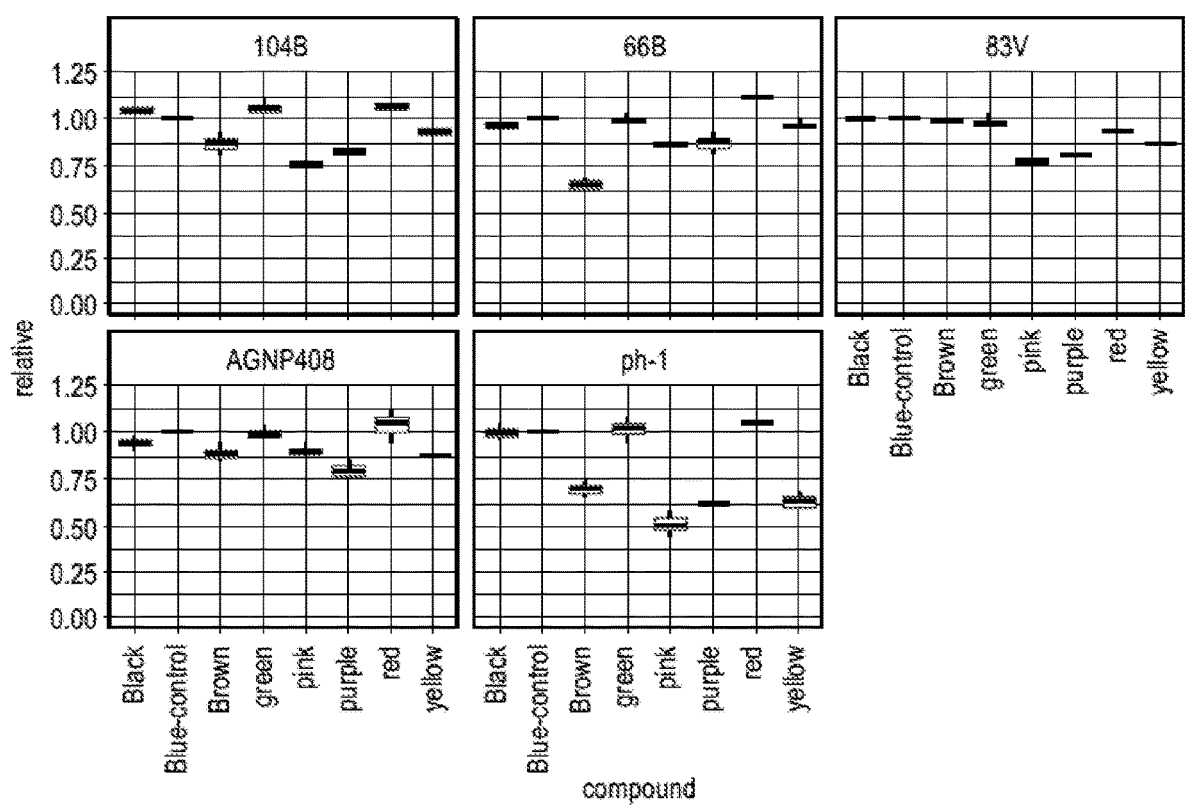
FIG. 3 illustrates the fungicidal performance of various compounds according to the disclosure against *Fusarium graminearum* isolates (e.g., 104B, 66B, 83V, AGNP408, and ph-1). "Relative" indicates the normalized percent radial mycelial growth.

Provided herein are compounds that inhibit succinate dehydrogenase (SDH). In particular, provided are compounds of Formula (I), and methods of making and using the same. The compounds described herein have a structure of Formula (I):

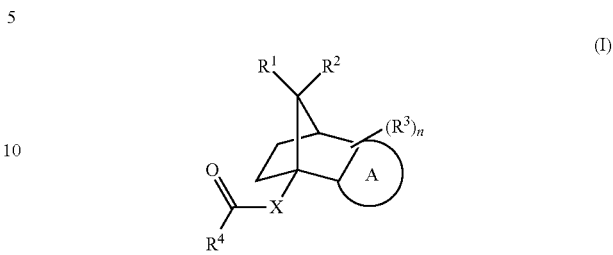

(I)

wherein the substituents are described in detail below.

The compounds described herein exhibit inhibitory activity against SDH and can be useful as fungicides.

Chemical Definitions

As used herein, the term "alkyl" refers to straight chained and branched saturated hydrocarbon groups. The term $C_n$ means the alkyl group has "n" carbon atoms. For example, $C_4$ alkyl refers to an alkyl group that has 4 carbon atoms. $C_{1-18}$ alkyl refers to an alkyl group having a number of carbon atoms encompassing the entire range (i.e., 1 to 18 carbon atoms), as well as all subgroups (e.g., 1-17, 1-16, 2-18, 1, 2, 3, 4, 5, 6, 7, 8, 9, 10, 11, 12, 13, 14, 15, 16, 17, and 18 carbon atoms). Nonlimiting examples of alkyl groups include, methyl, ethyl, n-propyl, isopropyl, n-butyl, sec-butyl (2-methylpropyl), and t-butyl (1,1-dimethylethyl), pentyl, hexyl, heptyl, octyl, nonyl, decyl, and dodecyl. Unless otherwise indicated, an alkyl group can be an unsubstituted alkyl group or a substituted alkyl group.

Specific substitutions on an alkyl group can be indicated by inclusion in the alkyl term, e.g., "haloalkyl" or "hydroxyalkyl" which mean an alkyl group substituted with at least one halo or at least one hydroxy group, respectively. A haloalkyl group can be perhalogenated. Nonlimiting examples of hydroxyalkyl include hydroxymethyl, hydroxyethyl, 2-hydroxypropyl, 2-hydroxybutyl, 3-hydroxybutyl, 2,3-dihydroxybutyl, and hydroxypentyl. Alkyl groups can be substituted with more than one type of substitution. For example, specifically contemplated are alkyl groups substituted with each of halo and hydroxy—i.e., a haloalkylene-OH moiety.

As used herein, the term "alkylene" refers to a bivalent saturated aliphatic radical. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups.

As used herein, the term "alkenyl" is defined identically as "alkyl" except for containing at least one carbon-carbon double bond. The term $C_n$ means the alkenyl group has "n" carbon atoms. For example, $C_4$ alkenyl refers to any alkenyl group that has 4 carbon atoms. $C_{2-18}$ alkenyl refers to an alkenyl group having a number of carbon atoms encompassing the entire range (i.e., 2 to 18 carbon atoms), as well as all subgroups (e.g., 2-17, 2-16, 3-18, 2, 3, 4, 5, 6, 7, 8, 9, 10, 11, 12, 13, 14, 15, 16, 17, and 18 carbon atoms). Nonlimiting examples of alkenyl groups include ethenyl, 1-propenyl, 2-propenyl, and butenyl. Unless otherwise indicated, an alkenyl group can be an unsubstituted alkenyl group or a substituted alkenyl group.

As used herein, the term "alkynyl" is defined identically as "alkyl" except for containing at least one carbon-carbon triple bond. The term $C_n$ means the alkynyl group has "n" carbon atoms. For example, $C_4$ alkynyl refers to any alkynyl group that has 4 carbon atoms. $C_{2-18}$ alkynyl refers to an alkynyl group having a number of carbon atoms encompassing the entire range (i.e., 2 to 18 carbon atoms), as well as all subgroups (e.g., 2-17, 2-16, 3-18, 2, 3, 4, 5, 6, 7, 8, 9, 10, 11, 12, 13, 14, 15, 16, 17, and 18 carbon atoms). Nonlimiting examples of alkynyl groups include ethynyl, 1-propynyl, 2-propynyl, and butynyl. Unless otherwise indicated, an alkynyl group can be an unsubstituted alkynyl group or a substituted alkynyl group.

As used herein, the term "heteroalkyl" is defined similarly as alkyl, except the backbone of the alkyl chain contains one to three heteroatoms independently selected from oxygen, nitrogen, or sulfur, but the point of attachment of the heteroalkyl moiety is a carbon atom, not the heteroatom. Nonlimiting examples of heteroalkyl includes ethers, thioethers, amines, esters, thioesters, and amides.

As used herein, the term "cycloalkyl" refers to a cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_{5-8}$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

As used herein, the term "heterocycloalkyl" is defined similarly as cycloalkyl, except the ring contains one to three heteroatoms independently selected from oxygen, nitrogen, or sulfur. Nonlimiting examples of heterocycloalkyl groups include piperidine, tetrahydrofuran, tetrahydropyran, dihydrofuran, morpholine, and oxazepaneyl. Cycloalkyl and heterocycloalkyl groups can be saturated or partially unsaturated ring systems optionally substituted with, for example, one to three groups, independently selected alkyl, alkylene-OH, C(O)NH$_2$, NH$_2$, oxo (=O), aryl, haloalkyl, halo, and OH.

As used herein, the term "aryl" refers to monocyclic or polycyclic (e.g., fused bicyclic and fused tricyclic) carbocyclic aromatic ring systems. $C_{6-10}$ aryl indicates the number of carbon atoms in the aromatic ring system is 6-10. Examples of aryl groups include, but are not limited to, phenyl, naphthyl, tetrahydronaphthyl, phenanthrenyl, biphenylenyl, indanyl, indenyl, anthracenyl, fluorenyl, tetralinyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to three ring atoms are selected from oxygen, nitrogen, or sulfur, and the remaining ring atoms are carbon, said ring system being joined to the remainder of the molecule by any of the ring atoms. Nonlimiting examples of heteroaryl groups include pyridyl, pyridazinyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thienyl, quinolinyl, isoquinolinyl, benzoxazolyl, benzimidazolyl, benzofuranyl, benzothiazolyl, triazinyl, triazolyl, purinyl, pyrazinyl, purinyl, indolinyl, phthalzinyl, indazolyl, quinolinyl, isoquinolinyl, cinnolinyl, quinazolinyl, naphthyridinyl, pyridopyridinyl, indolyl, 3H-indolyl, pteridinyl, and quinooxalinyl. Unless otherwise indicated, a heteroaryl group can be an unsubstituted heteroaryl group or a substituted heteroaryl group.

As used herein, the term "alkoxy" refers to a "—O-alkyl" group.

Compounds of the Disclosure

Provided herein are compounds having a structure of Formula (I), wherein

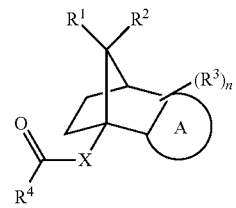

X is NH or O;

ring A is $C_{6-10}$ aryl or 5-12 membered heteroaryl having 1-3 ring heteroatoms selected from N, O, and S;

each of $R^1$ and $R^2$ is independently selected from H, halo, $C_{1-18}$ alkyl, $C_{2-18}$ alkenyl, $C_{2-18}$ alkynyl, $C_{1-18}$ alkoxy, $C_{1-18}$ haloalkyl, $C_{1-18}$ hydroxyalkyl, C(O)NHC$_{1-18}$alkyl, C(O)OC$_{1-18}$alkyl, C(O)SC$_{1-18}$alkyl, $C_{2-18}$ heteroalkyl having 1-3 backbone heteroatoms selected from N, I, and S, $C_{6-10}$ aryl, or 5-8 membered heteroaryl having 1-3 ring heteroatoms selected from N, O, and S; or $R^1$ and $R^2$ together form $C_{2-6}$ alkene, $C_{3-8}$ cycloalkyl, or $C_m$ heterocycloalkyl having 1-3 ring heteroatoms selected from N, O, and S, optionally substituted with 1-3 $R^3$ groups;

each $R^3$ is independently halo, CN, OH, NO$_2$, $C_{1-6}$ alkoxy, $C_{1-6}$ alkyl, $C_{1-6}$ hydroxyalkyl, $C_{1-6}$ haloalkyl, or $C_{1-6}$ haloalkylene-OH;

$R^4$ is $C_{2-6}$ alkyl, $C_{1-6}$ haloalkyl, $C_{1-6}$ heteroalkyl having 1-3 backbone heteroatoms selected from N, O, and S, $C_{3-8}$ cycloalkyl, $C_{6-10}$ aryl, 3-12 membered heterocycloalkyl having 1-3 ring heteroatoms selected from N, O, and S, or 5-12 membered heteroaryl having 1-3 ring heteroatoms selected from N, O, and S, and the aryl or heteroaryl group is optionally substituted with 1-3 $R^3$ groups; and n is 0, 1, 2, or 3;

with the proviso that if ring A is $C_6$ aryl, n is 0, and $R^1$ and $R^2$ are each H, then $R^4$ is not unsubstituted phenyl.

As described herein, X is NH or O. Accordingly, in embodiments, X is NH. In other embodiments, X is O.

In embodiments, ring A is $C_{6-10}$ aryl or 5-12 membered heteroaryl having 1-3 ring heteroatoms selected from N, O, and S. In embodiments, ring A is $C_{6-10}$ aryl. In embodiments, ring A is $C_6$ aryl. In some embodiments, ring A comprises phenyl. In embodiments, ring A is a 5-12 membered heteroaryl having 1-3 heteroatoms selected from N, O, and S. In embodiments, ring A is a 5-12 membered heteroaryl having 1 ring S atom. For example, ring A can comprise thiophenyl or thiazolyl. In certain embodiments, ring A comprises thiophenyl. In embodiments, ring A is a 6-membered heteroaryl having 1-2 ring N atoms. For example, ring A can comprise pyridyl or pyrimidyl. In some embodiments, ring A comprises pyridyl.

As described herein, each of $R^1$ and $R^2$ can be independently selected from H, halo, $C_{1-18}$ alkyl, $C_{2-18}$ alkenyl, $C_{2-18}$ alkynyl, $C_{1-18}$ alkoxy, $C_{1-18}$ haloalkyl, $C_{1-18}$ hydroxyalkyl, C(O)NHC$_{1-18}$alkyl, C(O)OC$_{1-18}$alkyl, C(O)SC$_{1-18}$alkyl, $C_{2-18}$ heteroalkyl having 1-3 backbone heteroatoms selected from N, O, and S, $C_{6-10}$ aryl, or 5-8 membered heteroaryl having 1-3 ring heteroatoms selected from N, O, and S. Alternatively, $R^1$ and $R^2$ can be together to form $C_{2-6}$ alkene, $C_{3-8}$ cycloalkyl, or $C_{3-8}$ heterocycloalkyl having 1-3 ring heteroatoms selected from N, O, and S, optionally substituted with 1-3 $R^3$ groups. In embodiments, at least one of $R^1$ and $R^2$ is $C_{1-6}$ alkyl.

In embodiments, $R^3$ is independently halo, CN, OH, $NO_2$, $C_{1-6}$ alkoxy, $C_{1-6}$ alkyl, $C_{1-6}$ hydroxyalkyl, $C_{1-16}$ haloalkyl, or $C_{1-6}$ haloalkylene-OH. The number and location of the $R^3$ group(s) on the disclosed compound are not particularly limited. In embodiments, an $R^3$ group is attached to the norbornane ring. In embodiments, an $R^3$ group is attached to ring A. In some embodiments, an $R^3$ group is attached to both ring A and the norbornane ring. In embodiments, the total number of $R^3$ groups in the compound ranges from 0 to 3. That is, there can be 0, 1, 2, or 3 $R^3$ groups attached to ring A and/or the norbornane ring.

As described herein, $R^4$ is $C_{2-6}$ alkyl, $C_{1-16}$ haloalkyl, $C_{1-16}$ heteroalkyl having 1-3 backbone heteroatoms selected from N, O, and S, $C_{3-8}$ cycloalkyl, $C_{6-10}$ aryl, 3-12 membered heterocycloalkyl having 1-3 ring heteroatoms selected from N, O, and S, or 5-12 membered heteroaryl having 1-3 ring heteroatoms selected from N, O, and S, and the aryl or heteroaryl group is optionally substituted with 1-3 $R^3$ groups. In some aspects, $R^4$ is $C_{6-10}$ aryl or 5-8 membered heteroaryl. In some aspects, $R^4$ comprises pyrazolyl.

In embodiments, $R^4$ has the structure:

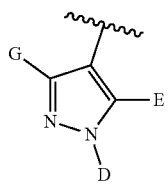

wherein each of G and E is independently H, halo, $C_{1-6}$ alkyl, $C_{1-6}$ hydroxyalkyl, $C_{1-6}$ haloalkylene-OH, or $C_{1-6}$ haloalkyl, and D is H, $C_{1-6}$ alkyl, or $C_{1-6}$ haloalkyl.

In some embodiments, D is $C_{1-6}$ alkyl. For example, D can be $CH_3$.

In some embodiments, G is H or $C_{1-6}$ haloalkyl. For example, in some aspects, G is H, $CHF_2$ or $CF_3$. In some embodiments, G is H. In some embodiments, G is $CHF_2$. In some embodiments, G is $CF_3$.

In some embodiments E is H, halo, $C_{1-6}$ haloalkylene-OH, or $C_{1-6}$ haloalkyl. For example in some aspects, E is H, Cl, $CHF_2$, $CF_3$, or $CF_2CH_2OH$. In some embodiments, E is H. In some embodiments, E is Cl. In some embodiments, E is $CHF_2$. In some embodiments, E is $CF_3$. In some embodiments, E is $CF_2CH_2OH$.

In embodiments, $R^4$ is selected from:

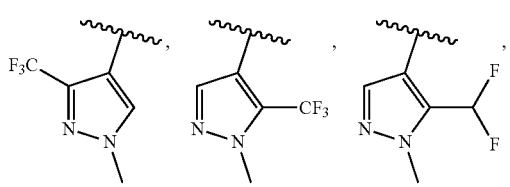

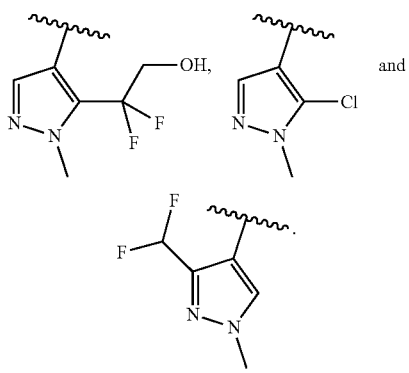

In aspects of the disclosure the compound can have a structure selected from the group consisting of:

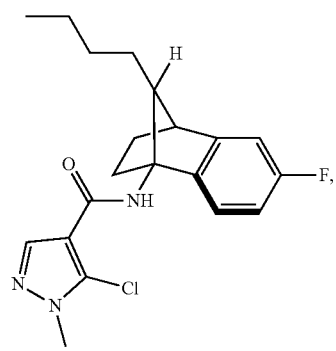

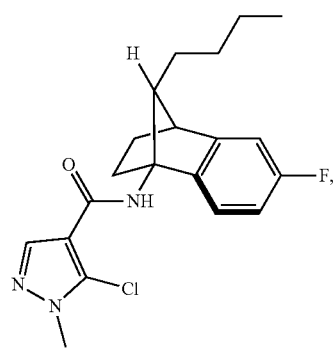

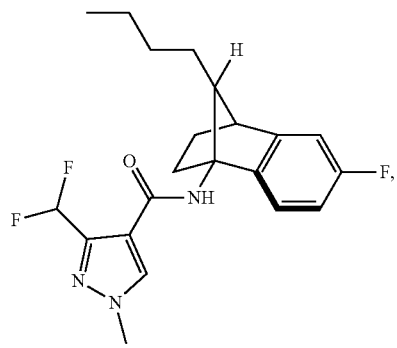

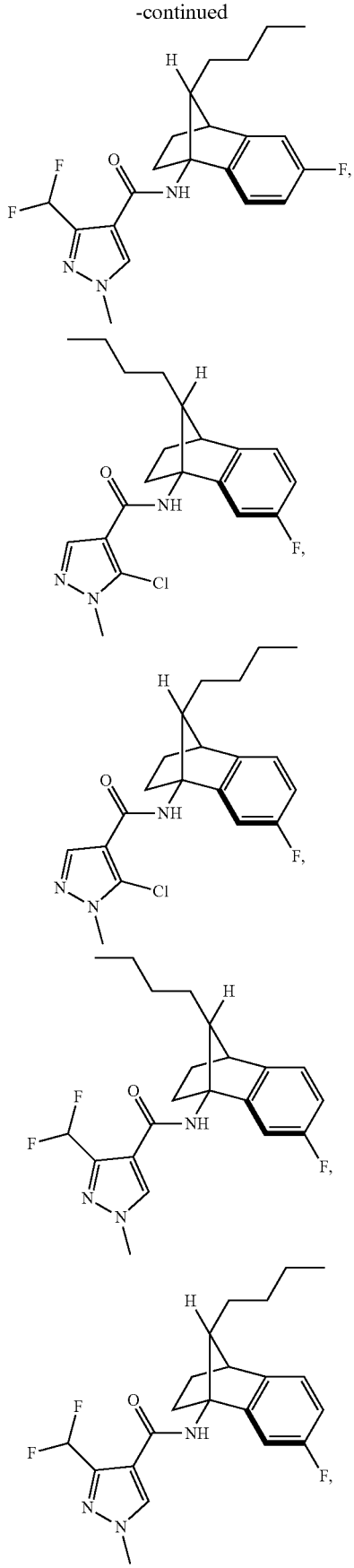
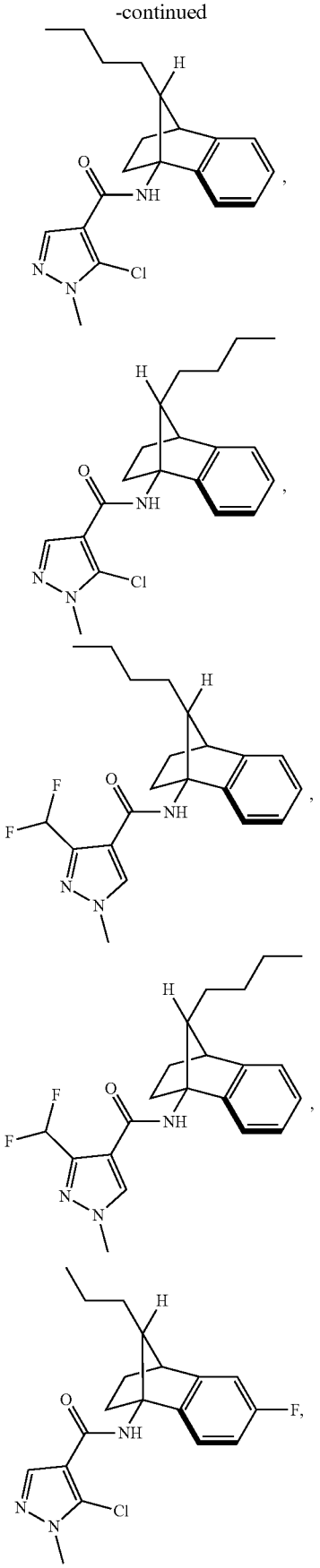

-continued
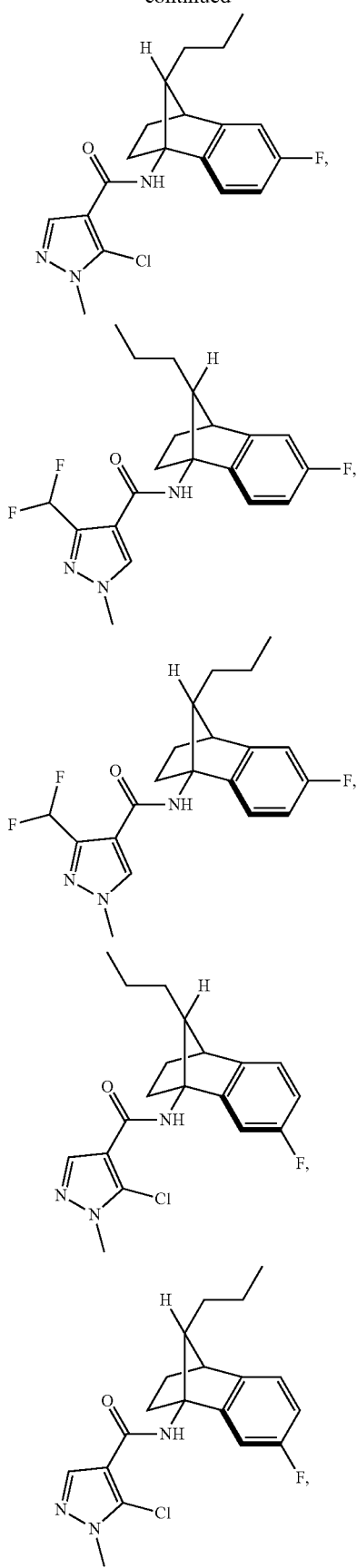
-continued
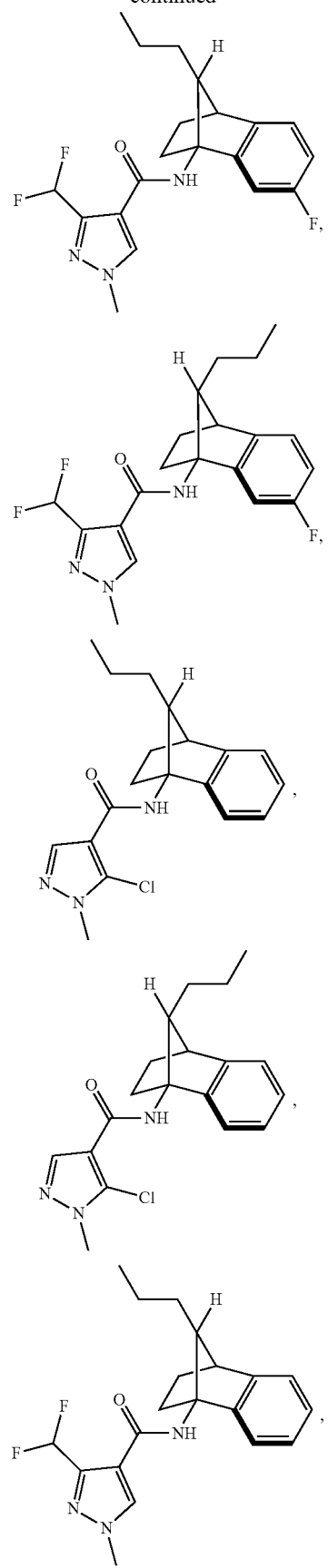

13
-continued
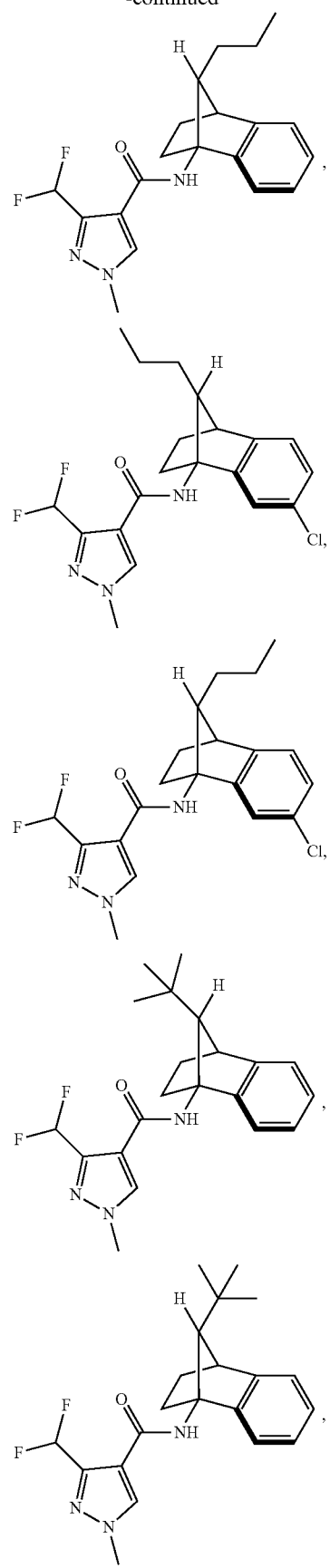
14
-continued
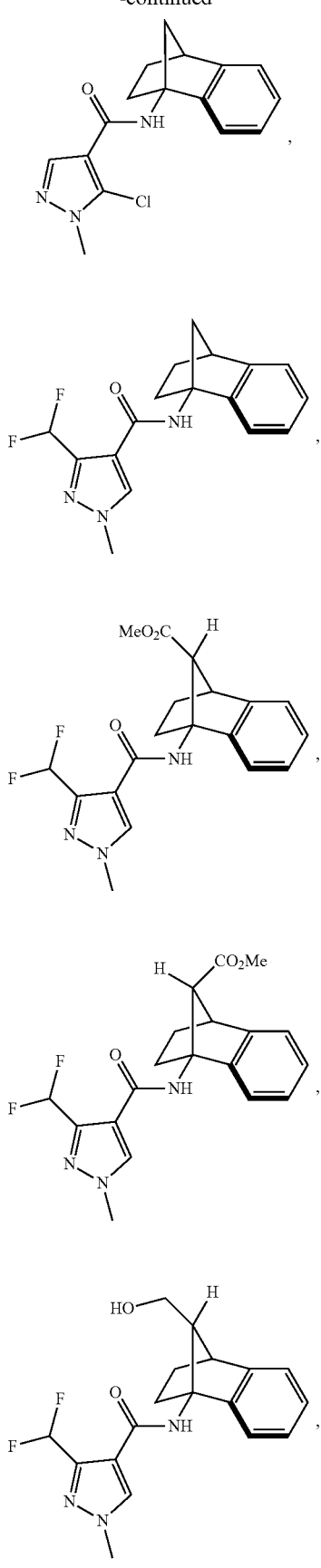

15
-continued
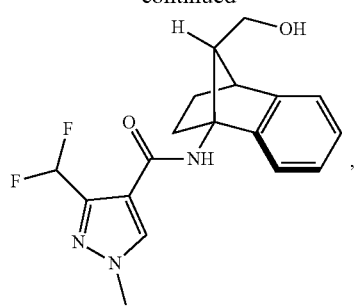
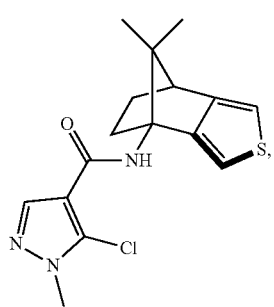
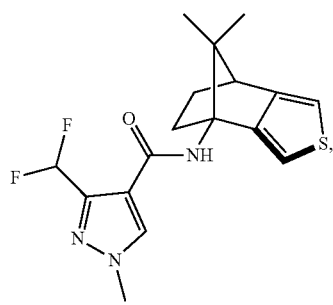
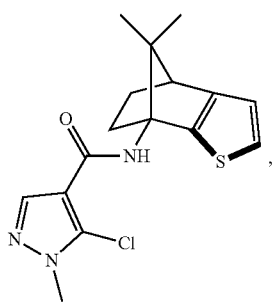
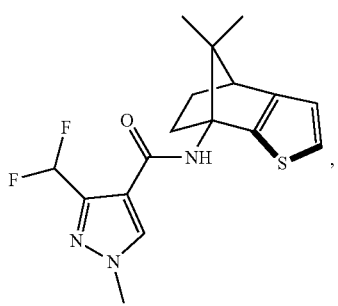
16
-continued
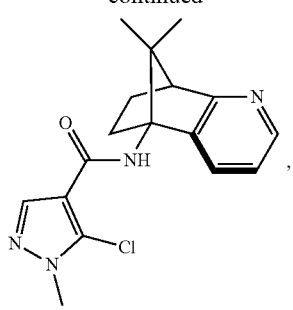
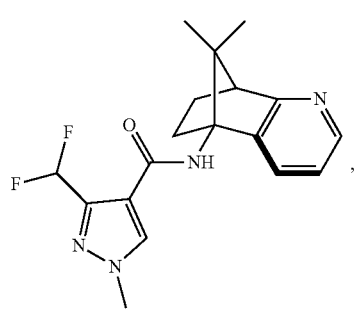
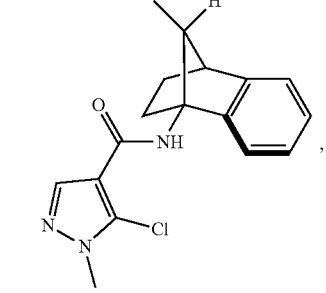
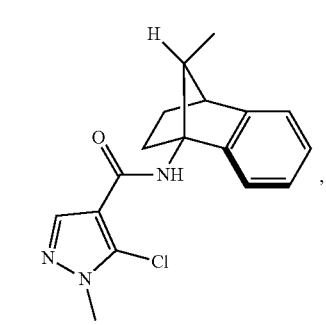
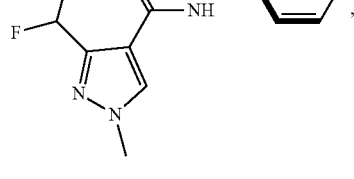

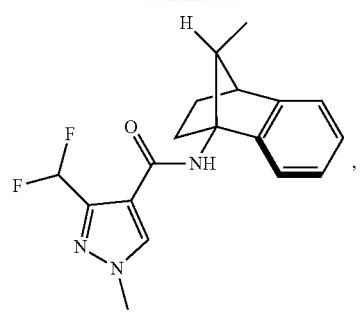,
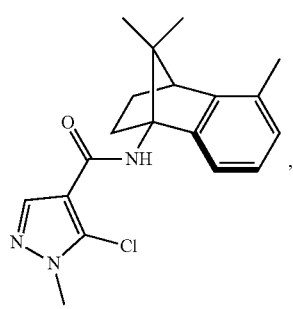,
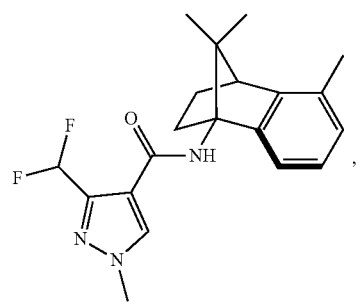,
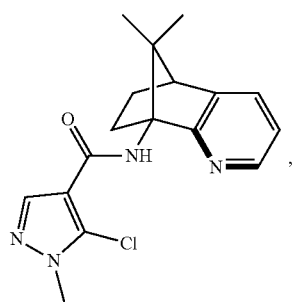,
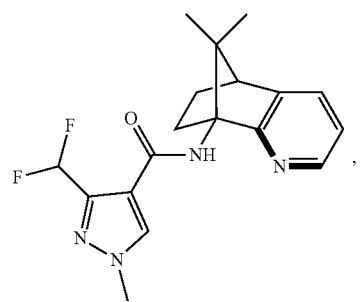,
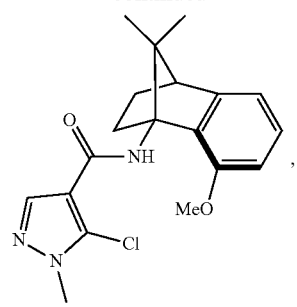,
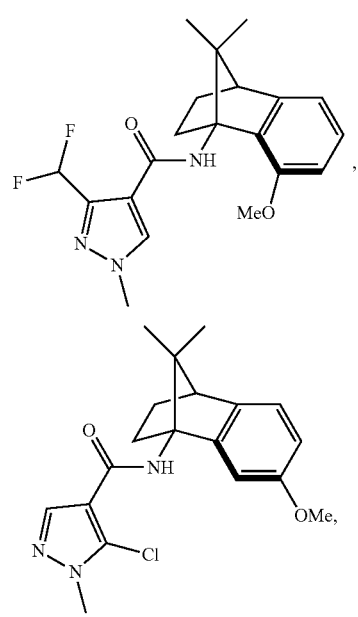
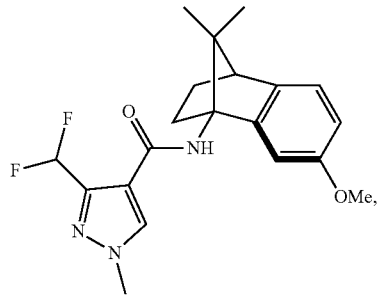,
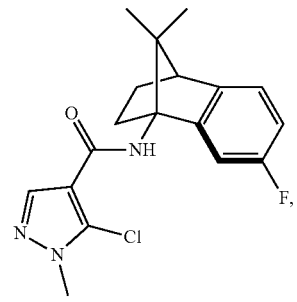, -continued
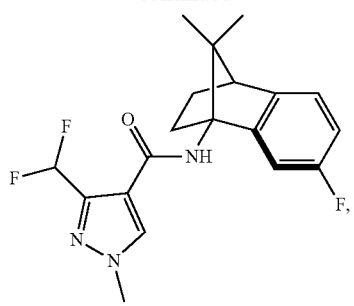
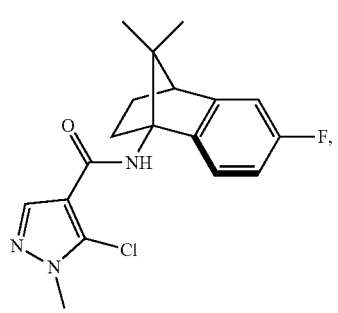
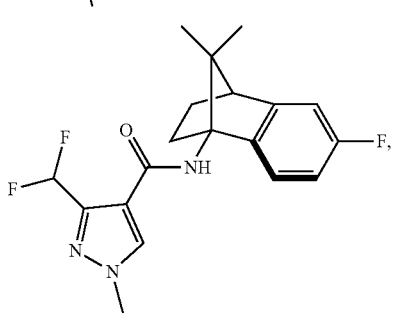
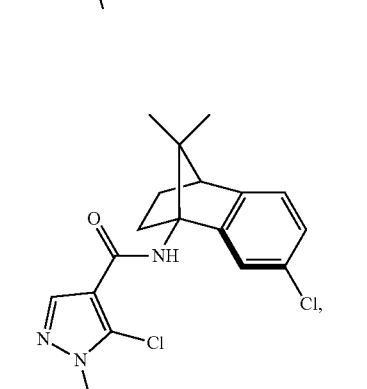
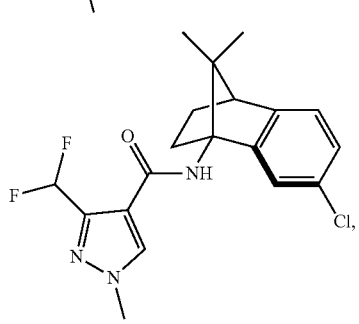
-continued
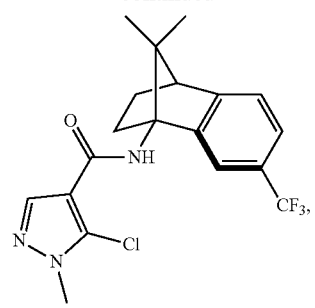
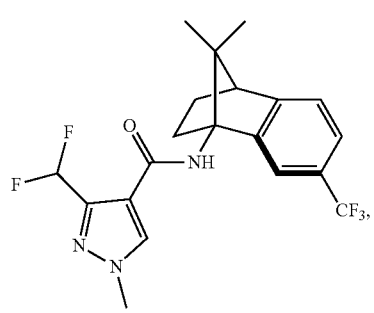
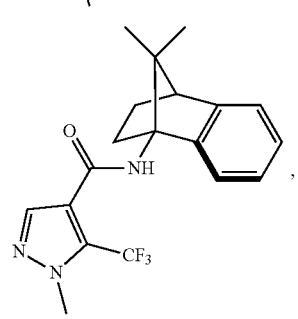
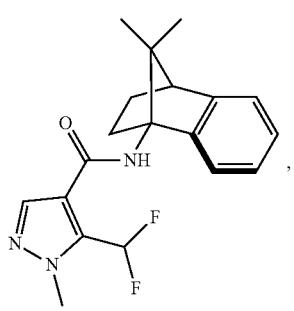
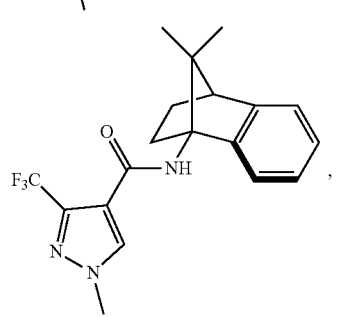

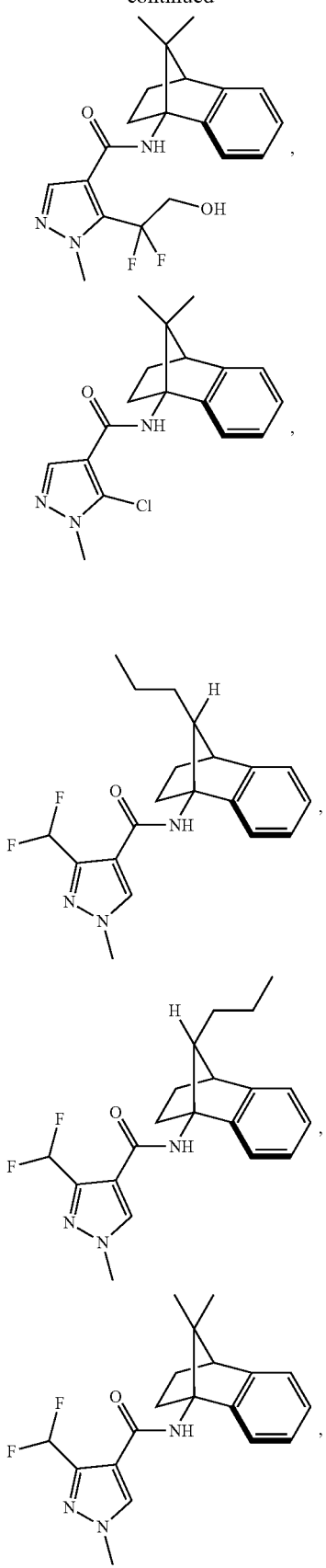
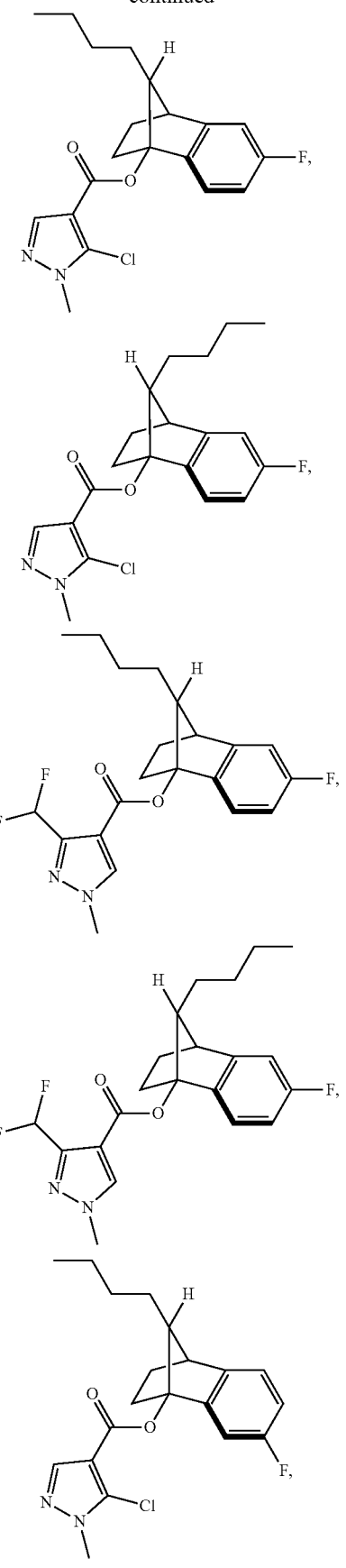

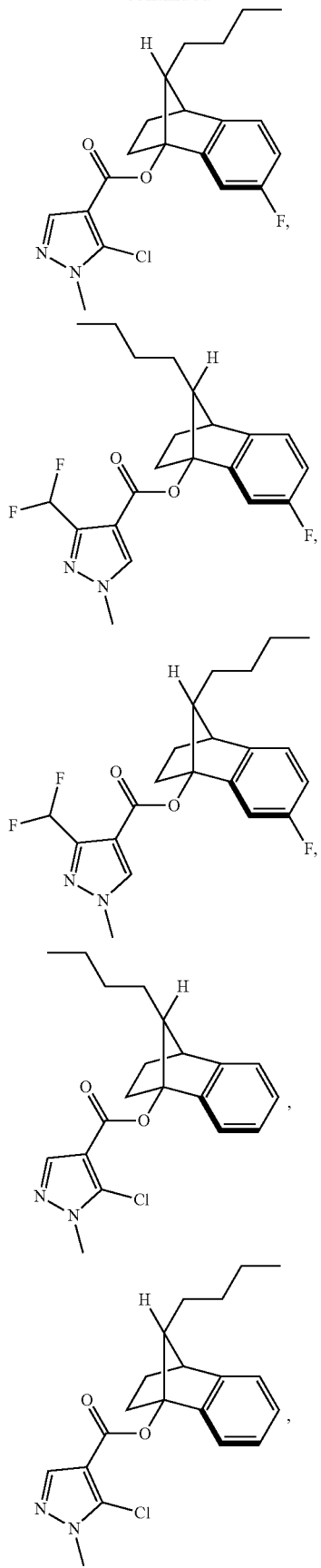
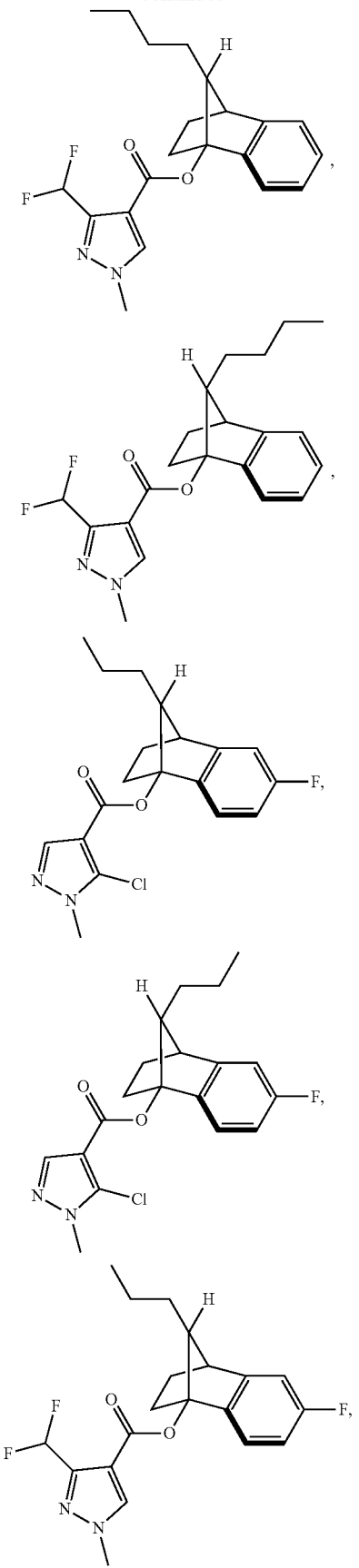

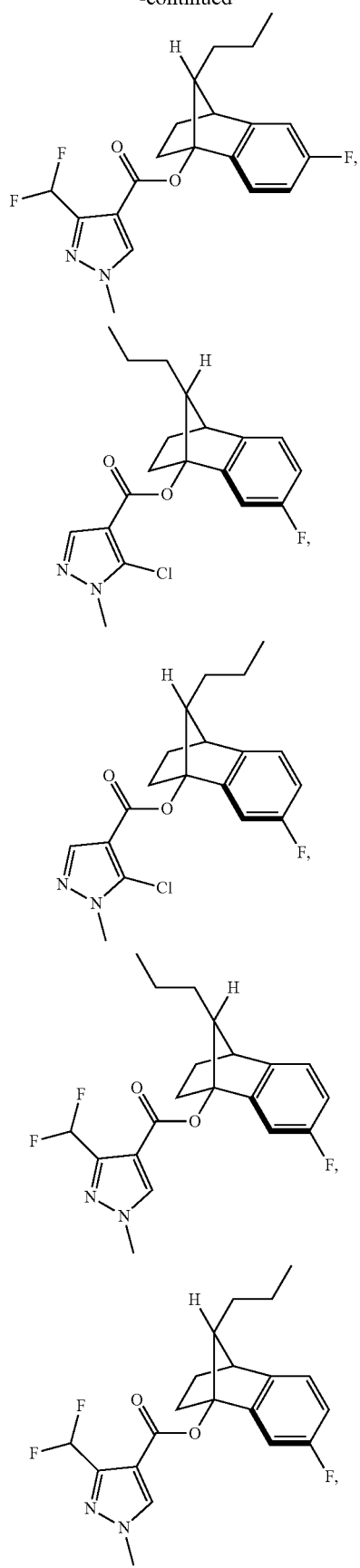
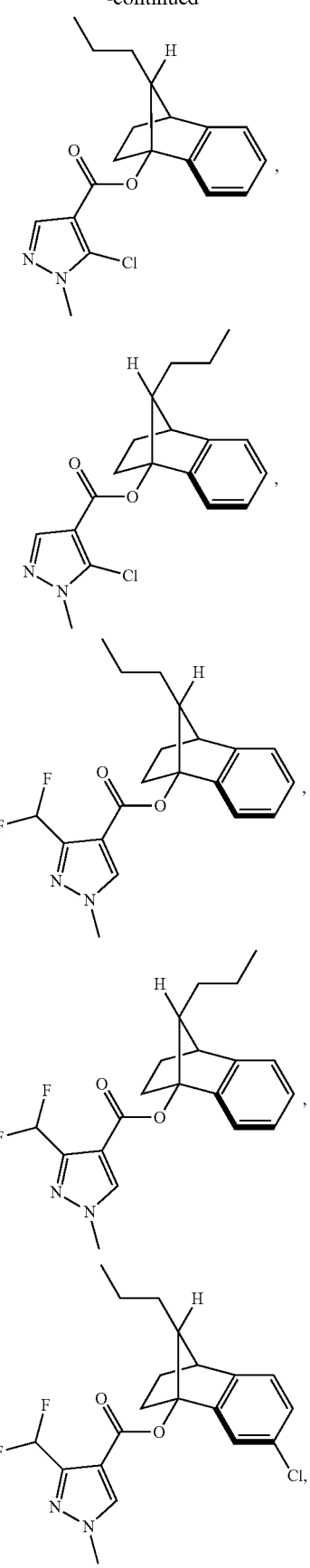

-continued
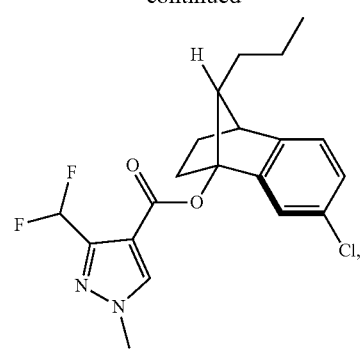
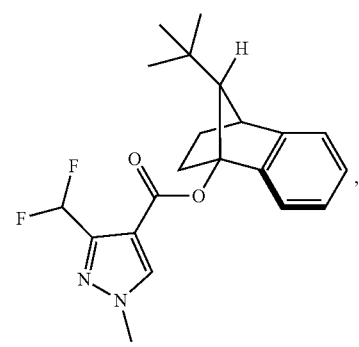
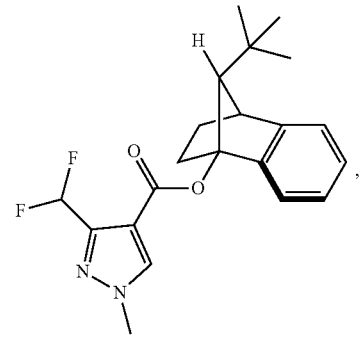
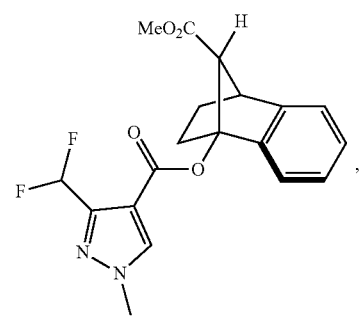
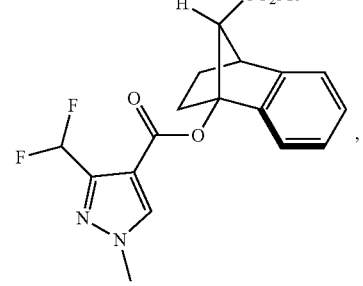
-continued
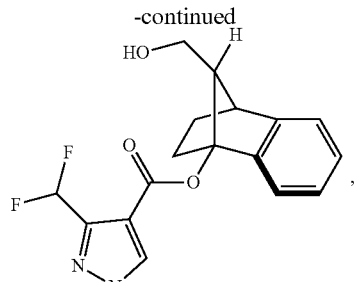
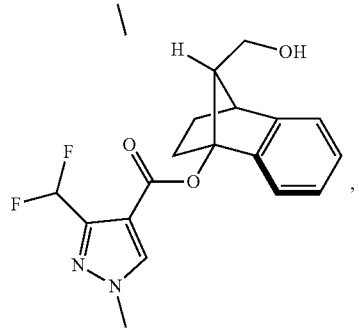
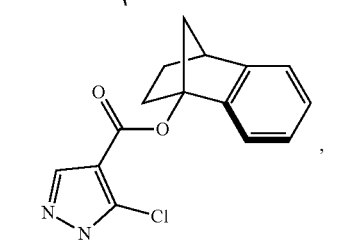
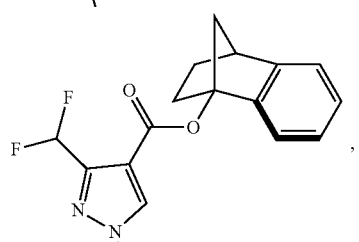
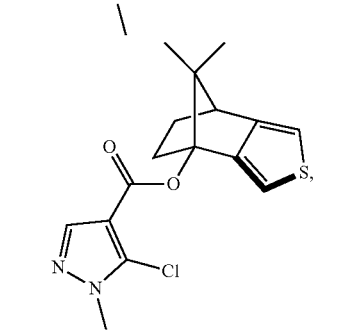
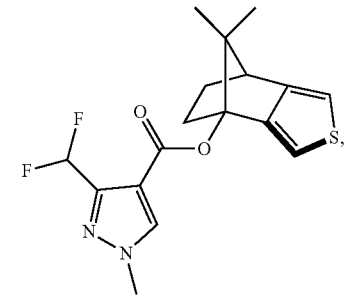

29
-continued
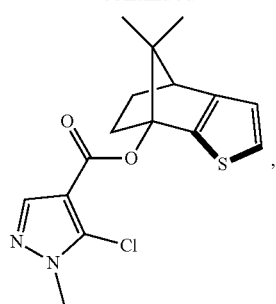
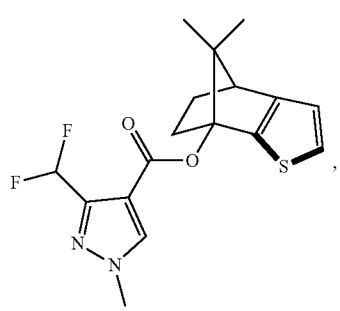
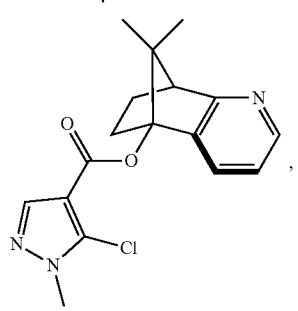
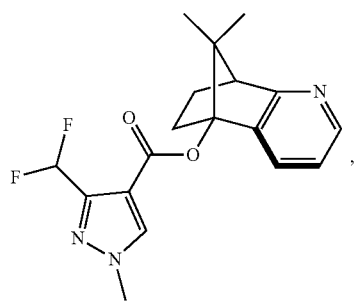
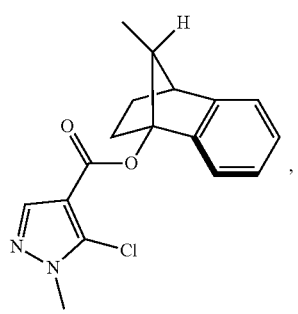
30
-continued
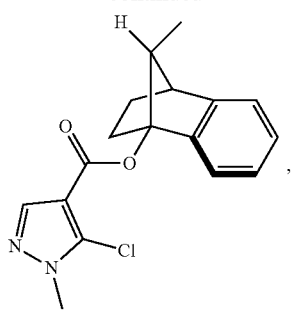
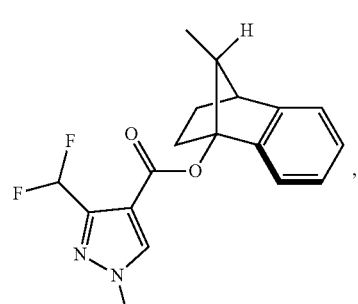
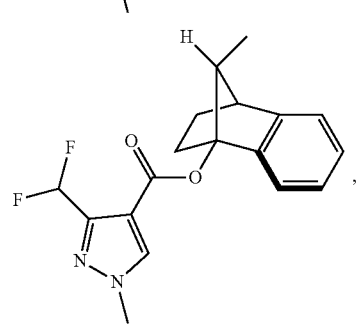
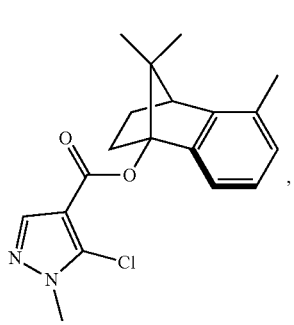
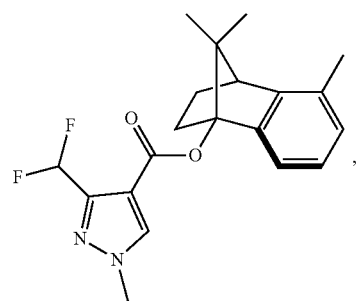

-continued
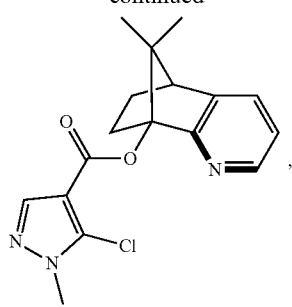
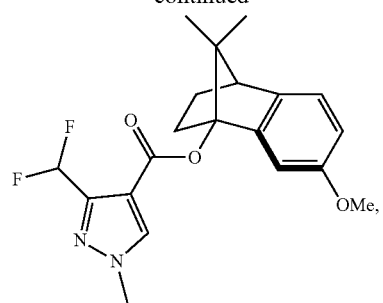
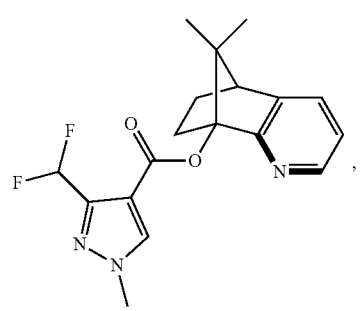
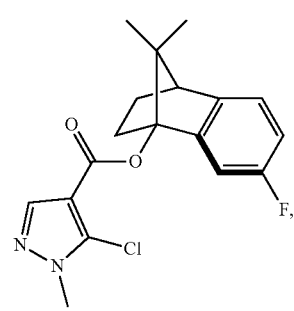
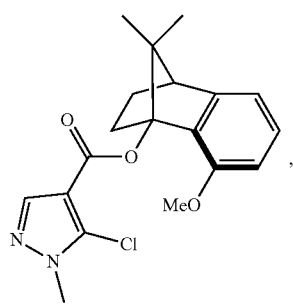
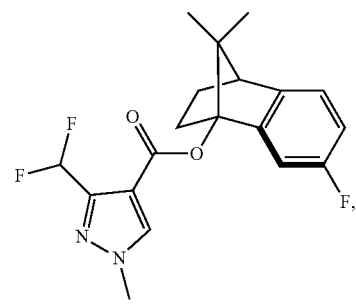
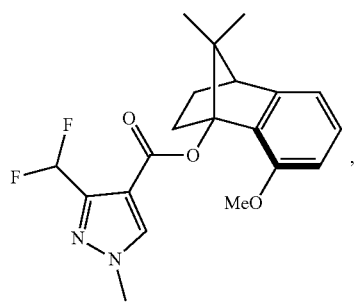
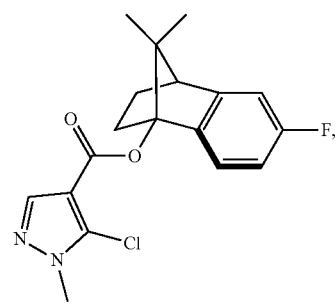
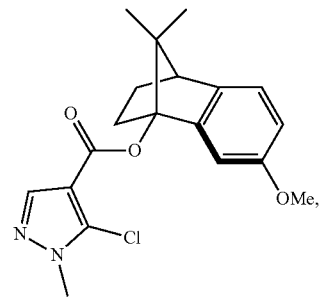
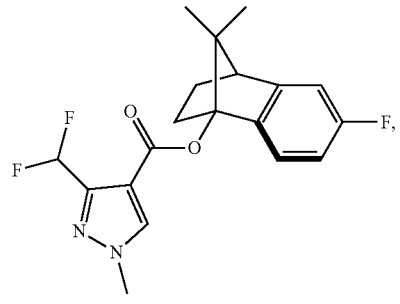

33
-continued
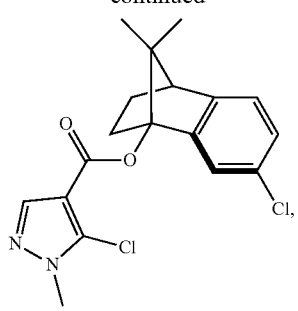
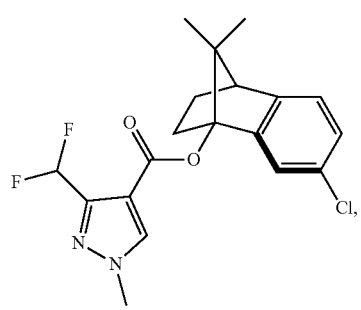
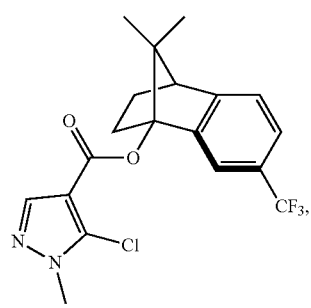
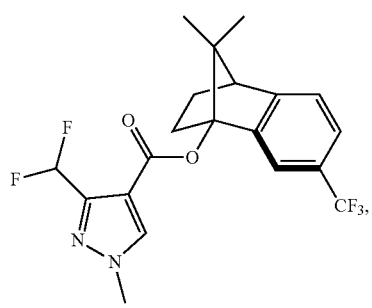
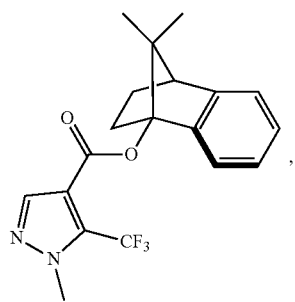
34
-continued
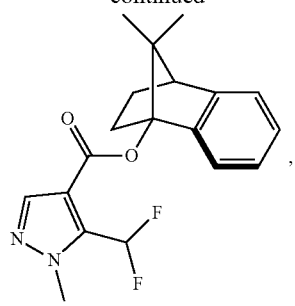
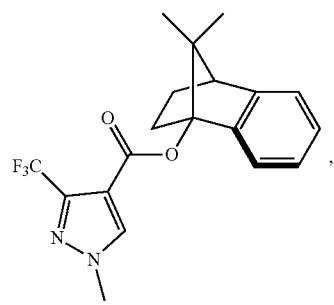
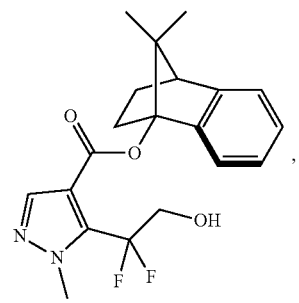
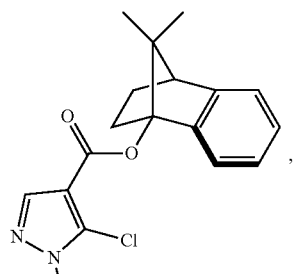
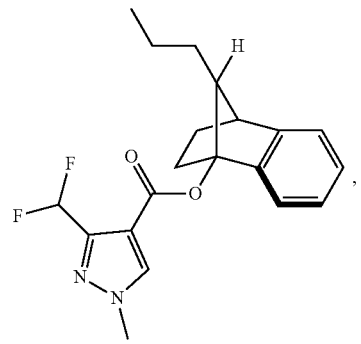

-continued

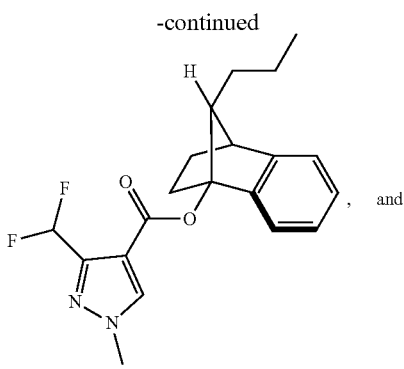, and

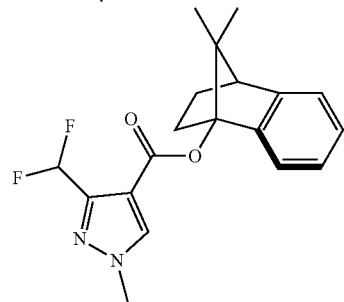.

Methods of Preparing Disclosed Compounds

The disclosure further provides methods of preparing compounds as described herein.

In embodiments, a method of preparing the compounds of the disclosure comprises irradiating a compound of Formula (II) to form an intermediate of formula (III):

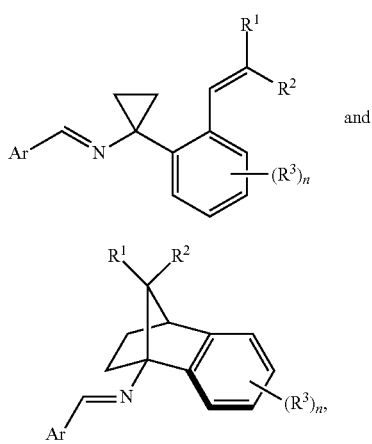

wherein Ar comprises a $C_6$ aryl.

In embodiments Ar comprises nitro-phenyl.

The disclosed methods comprise irradiating the compound of Formula (II). In embodiments, the irradiation can include UV, IR, or visible light. The compound of Formula (II) can be dissolved in any suitable solvent that does not prohibit or hinder the reaction, for example, acetonitrile.

The disclosed methods can be carried out at any temperature for any amount of time that is suitable to achieve the compounds described herein. For example, and without intending to be bound by theory, the irradiation time will generally increase with the quantity of the starting material. Further, the reaction can be carried out at any temperature suitable for the chemistry involved in achieving the claimed compounds. For example, the reaction can be carried out at temperatures ranging from about 0° C. to about 100° C., about 25° C. to about 75° C., or about 30° C. to about 40° C., for example about 0, 5, 10, 15, 20, 25, 30, 35, 40, 45, 50, 55, 60, 65, 70, 75, 80, 85, 90, 95, or 100° C.

In embodiments, the irradiating step is via exposure to a 390 nm light at a temperature for 30-35° C.

The disclosed methods can be carried out in any solvent compatible with the synthesis of compounds as described herein. Suitable solvents include, but are not limited to, dichloromethane (DCM), 1,2-dichloroethane, pentane, hexanes, heptane, methyl tert-butyl ether, diethyl ether, tetrahydrofuran (THF), ethyl acetate, methyl acetate, dimethyl formamide (DMF), N-methylpyrrolidinone, methanol, ethanol, isopropanol, acetic acid, and water.

In some embodiments, the disclosed methods further comprise hydrolyzing the intermediate of Formula (III) to form an amine and acylating the resulting amine to form a compound as described herein. In some embodiments, the method further comprises solvolyzing (e.g., with methanol) the Schiff base of the intermediate of Formula (III) to form an amine, and reacting the amine with an acyl reagent having a structure

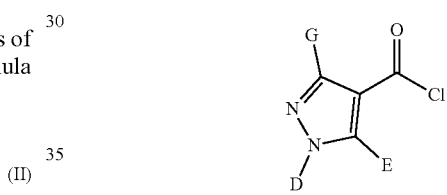

to form the compound of Formula (I). In embodiments, the acyl reagent has a structure of

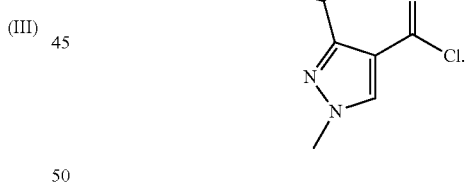

In some embodiments, the method further includes hydrolyzing the Schiff base of the intermediate of Formula (III) to form an amine, converting the resulting amine to an alcohol, and acylating the resulting alcohol to form a compound as described herein.

In embodiments, compounds according to the disclosure can be prepared through the functionalization of a carboxylic acid group at the $R^1$ or $R^2$ position. The compounds can be formed using a variety of known derivation techniques and pathways shown in Scheme 1, below, wherein R* is $C(O)R^4$ and R can be any $R^1$ and/or $R^2$ as described herein:

Scheme 1
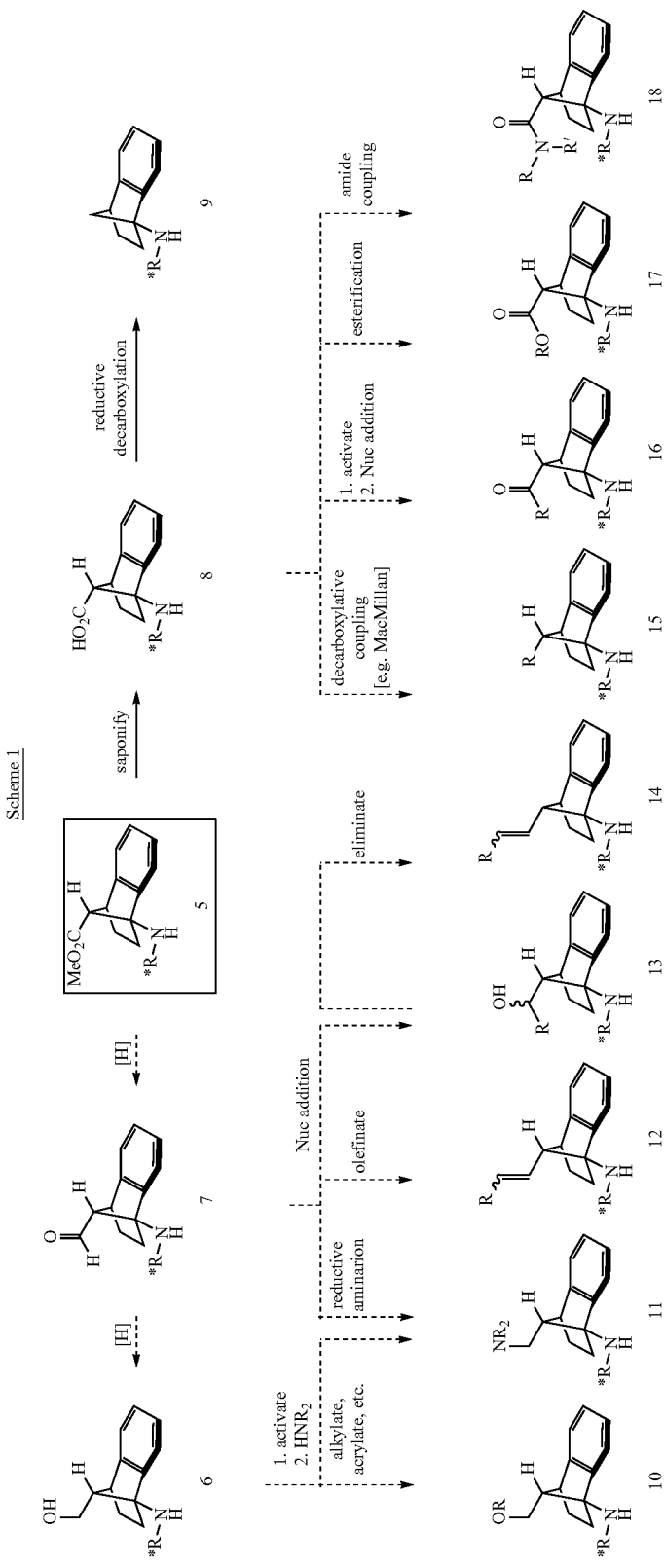

In embodiments, the intermediate of the irradiating step is not isolated prior to the hydrolyzing (or solvolyzing) step. In embodiments, the irradiating step and the hydrolyzing step can occur sequentially in the same vessel. In embodiments, the irradiating and the hydrolyzing step can occur via continuous manufacturing. Continuous manufacturing can comprise using, for example, a Y-mixer, T-mixer, reaction loop, falling film reactor, or a micromixer chip. As would be appreciated, any manufacturing equipment suitable for carrying out the described methods can be utilized.

The compounds according to the disclosure can be purified, e.g., via chromatography and/or crystallization (or recrystallization), to provide isolated isomers. The compounds can also be purified via chromatography. The compounds can also be purified via crystallization or recrystallization. In some cases, the compounds can be purified via crystallization or recrystallization of the crude reaction mixture, wherein no chromatography is necessary. Examples of suitable crystallization or recrystallization solvents include ethyl acetate, hexanes, dichloromethane, toluene, isopropanol, and mixtures thereof. For example, in some embodiments, the crystallization or recrystallization solvent can comprise an ethyl acetate:hexanes mixture, a dichloromethane:hexanes mixture, or a toluene:isopropanol mixture.

Formulations of the Disclosed Compounds

The disclosure further provides formulations comprising compounds as described herein. In embodiments, the formulation comprises a compound as described herein and a carrier.

Compounds as disclosed herein can be dispersed in water, or another liquid, for application, or formulations can be dust-like or granular, which can then be applied without further treatment. The formulations are prepared according to procedures which are conventional in the agricultural chemical art.

The formulation can be an aqueous suspension or emulsion. The formulation can be prepared as a solid, usually known as a wettable powder, or a liquid, usually known as an emulsifiable concentrate, aqueous suspension, or suspension concentrate. The present disclosure contemplates all vehicles by which the disclosed compounds can be formulated for delivery and use as a fungicide.

As will be readily appreciated, any material to which the disclosed compounds can be added may be used, provided they yield the desired utility without significant interference with the activity of these compounds as antifungal agents.

Wettable powders, which may be compacted to form water-dispersible granules, can comprise an intimate mixture of disclosed compound and a carrier. The wettable powder can further include agriculturally acceptable surfactants. The concentration of the disclosed compound in the wettable powder is usually from about 10% to about 90% by weight, or about 25% to about 75% by weight, based on the total weight of the formulation. In the preparation of wettable powder formulations, the disclosed compound can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the compound in a volatile organic solvent. Effective surfactants, comprising from about 0.5% to about 10% by weight of the wettable powder, can include sulfonated lignins, naphthalenesulfonates, alkylbenzenesulfonates, alkyl sulfates, and non-ionic surfactants, such as ethylene oxide adducts of alkyl phenols.

Emulsifiable concentrates of the aryl-fused 1-aminonorbornante compound can comprise a concentration of from about 10% to about 50% by weight of the compound, in a suitable liquid, based on the total weight of the emulsifiable concentrate formulation. The disclosed compound is dissolved in a carrier, which can be either a water-miscible solvent or a mixture of water-immiscible organic solvents, and emulsifiers. The concentrates can be diluted with water and oil to form spray mixtures in the form of oil-in-water emulsions. Useful organic solvents include aromatics, particularly the high-boiling naphthalenic and olefinic portions of petroleum such as heavy aromatic naphtha. Other organic solvents can also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which can be employed in preparing the emulsifiable concentrates of the present disclosure are the aromatic liquids such as xylene, propyl benzene fractions, or mixed naphthalene fractions, mineral oils, substituted aromatic organic liquids such as dioctyl phthalate, kerosene, dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The formulations can also contain other compatible additives, for example, plant growth regulators and other biologically active compounds used in agriculture.

Aqueous suspensions comprise suspensions of one or more water-insoluble compounds, dispersed in an aqueous vehicle at a concentration in the range from about 5% to about 70% by weight, based on the total weight of the aqueous suspension formulation. Suspensions are prepared by finely grinding the disclosed compound, and vigorously mixing the ground material into a vehicle comprised of water and surfactants chosen from the same types discussed above. Other ingredients, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The formulation may also be applied as a granular formulation, which is particularly useful for applications to the soil. Granular formulations usually contain from about 0.5% to about 10% by weight of the compounds, based on the total weight of the granular formulation, dispersed in a carrier which can include coarsely divided attapulgite, bentonite, diatomite, clay or a similar inexpensive substance. Such formulations are usually prepared by dissolving the disclosed compound in a suitable solvent and applying it to a granular carrier which has been performed to the appropriate particle size, for example, in the range of from about 0.5 to about 3 mm. Such formulations may also be prepared by making a dough or paste of the carrier and the disclosed compound, and crushing and drying to obtain the desired granular particle.

Dusts containing the disclosed compound are prepared by intimately mixing the compound in powdered form with a suitable dusty agricultural carrier, such as, for example, kaolin clay, ground volcanic rock, and the like.

The formulation can contain agriculturally acceptable adjuvant surfactants to enhance deposition, wetting and penetration of the compound onto the target crop and organism. These adjuvant surfactants may optionally be employed as a component of the formulation or as a tank mix. The amount of adjuvant surfactant will vary from about 0.01 percent to about 1.0 percent volume/volume (v/v) based on a spray-volume of water, preferably about 0.05 to about 0.5 percent. Suitable adjuvant surfactants include ethoxylated nonyl phenols, ethoxylated synthetic or natural alcohols, salts of the esters or sulfosuccinic acids, ethoxylated organosilicones, ethoxylated fatty amines and blends of surfactants with mineral or vegetable oils.

The formulations may optionally include combinations that can comprise one or more of the compounds disclosed herein with another active agent, such as a pesticide. Such pesticides may be fungicides, insecticides, nematocides, miticides, arthropodicides, bactericides or combinations thereof that are compatible with the compound of the present disclosure in the medium selected for application, and not antagonistic to the activity of the present compounds. Accordingly, in such embodiments the pesticide is employed as a supplemental toxicant for the same or for a different pesticidal use. The pesticide and the compound as disclosed herein can generally be mixed together in a weight ratio of from about 1:100 to about 100:1.

Methods of Inhibiting SDH and Use as Fungicides

The disclosure further provides methods of inhibiting SDH comprising contacting SDH with a compound as disclosed herein. Further provided are methods of preventing fungal growth on a plant, including applying to the plant the compound as disclosed herein.

The methods disclosed comprise applying the compound and/or formulations thereof to one or more of an area adjacent to a plant, soil adapted to support growth of the plant, a root of the plant, foliage of the plant, and/or a seed adapted to produce the plant. The methods can further comprise applying the compound and/or formulations thereof to the locus of the fungus, or to a locus in which the infestation is to be prevented. The compound and formulations are suitable for treatment of various plants at fungicidal levels, while exhibiting low phytotoxicity. The compound and/or formulation is useful in a protectant or eradicant fashion. The compound or formulation can be applied to the roots, seeds or foliage of plants for the control of various fungi, without damaging the commercial value of the plants. The compound or formulation is applied in the form of any of the generally used formulation types, for example, as solutions, dusts, wettable powders, flowable concentrates, or emulsifiable concentrates. These materials are conveniently applied in various known fashions.

In embodiments, the compounds disclosed inhibit or prevent the growth of a fungus selected from the group consisting of *Sclerotinia, Fusarium, Macrophomina, Monilinia, Mycosphaerella, Puccinia, Microdochium, Blumeria, Pyrenophora, Rhynchosporium, Ramularia, Botrytis, Erysiphe, Venturia, Podosphaera, Sphaerotheca, Golovinomyces, Alternaria, Leptosphaeria, Helminthosporium, Rhizoctonia, Oidium, Phakopsora, Corynespora, Ustilago, Aspergillus, Zymoseptoria, Pyrenophora, Didymella, Stemphylium, Erysiphe, Coprinus, Blumeriella, Pythium, Phytophthora, Septoria, Penicillium*, and *Cerospora*.

The exact amount of the compound and/or formulation to be applied is dependent not only on the relative amounts of the components, but also on the particular action desired, the fungal species to be controlled, and the stage of growth thereof, as well as the part of the plant or other product to be contacted with the synergistic composition. Thus, formulations containing the disclosed compound may not be equally effective at similar concentrations or against the same fungal species.

The present compounds and formulations thereof can be applied by the use of conventional ground sprayers, granule applicators, and by other conventional means known to those skilled in the art.

It is understood that while the disclosure is read in conjunction with the detailed description thereof, the foregoing description and following examples are intended to illustrate and not limit the scope of the disclosure, which is defined by the scope of the appended claims. Other aspects, advantages, and modifications are within the scope of the following claims.

EXAMPLES

Example 1: Synthesis of Disclosed Compounds

Compounds as provided herein can be prepared via cyclization of a Schiff base as shown in Scheme 2:

The resulting cyclic intermediate can be hydrolyzed and acylated to provide a compound according to the disclosure. A complete depiction of an exemplary reaction, inclusive of reaction conditions and yields, used to obtain a compound according to the disclosure is shown in reaction Scheme 3, below:

Scheme 3

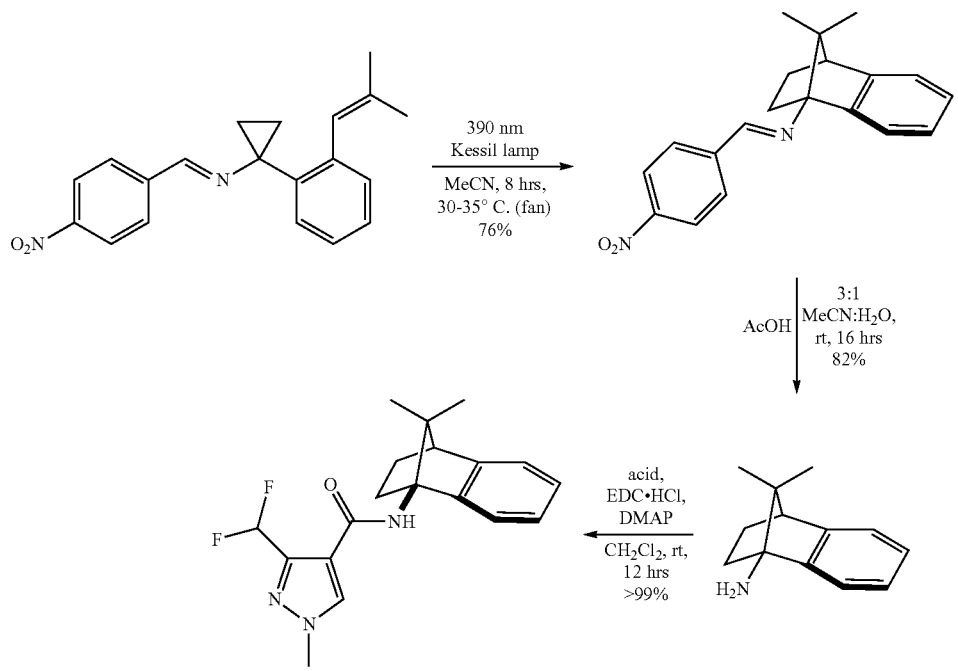

The nitrophenyl Schiff base was subjected to irradiation using a Kessil lamp at 390 nm in acetonitrile for 8 hours at 30-35° C. The resulting rearranged Schiff base was then hydrolyzed in acetic acid in a mixture of acetonitrile and water (3:1 volume ratio), stirred at room temperature for 16 hours. The free amine was then reacted with the pyrazole acid using a coupling reagent 1-ethyl-3-(3-dimethylaminopropyl)carbodiimide (EDC) and 4-dimethylaminopyrdine (DMAP) in methylene chloride at room temperature for 12 hours to form the amide bond and the desired compound.

A carboxymethyl group at the $R^1/R^2$ position can also be present in the compounds being prepared. The presence of the carboxymethyl group permits the functionalization at the $R^1/R^2$ positions, in addition to ring A, $R^3$ and $R^4$. Compound 4, as shown in reaction Scheme 4, below, was prepared using reductive decarboxylation of Compound 3, in addition to the use of irradiation with blue, visible light.

Scheme 4

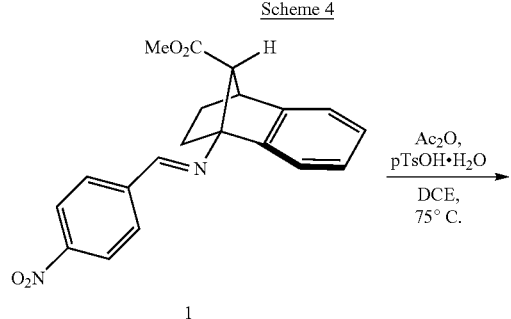

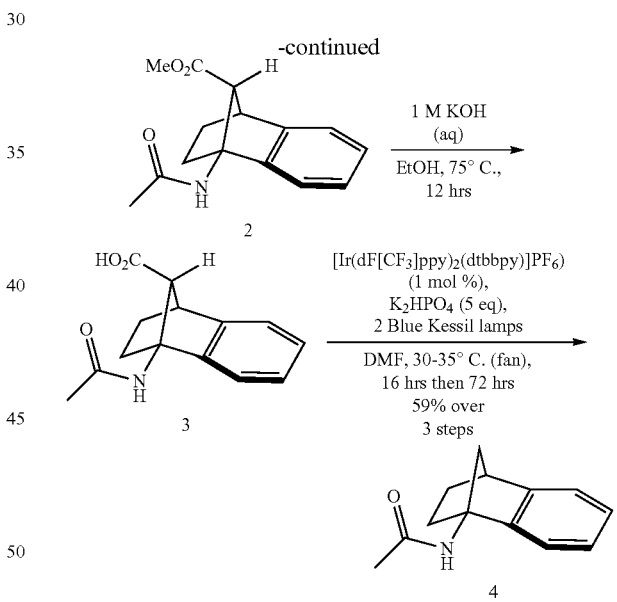

As shown in Scheme 4, the rearranged nitrophenyl Schiff base having a CO$_2$Me group (compound 1) was reacted in a mixture of acetic anhydride and p-toluenesulfonic acid monohydrate in 1,2-dichloroethane (DCE) at a temperature of 75° C. to form the corresponding amide (compound 2). The ester was then hydrolyzed using 1 M potassium hydroxide (KOH) in an ethanol solution at 75° C. for 12 hours to provide the free acid of compound 3. Compound 3 was then irradiated with 2 blue Kessil lamps in the presence of 1 mol % [4,4'-Bis(1,1-dimethylethyl)-2,2'-bipyridine-N1,N1]bis [3,5-difluoro-2-[5-(trifluoromethyl)-2-pyridinyl-N]phenyl-C]Iridium(III) hexafluorophosphate ([Ir(dF[CF$_3$]ppy)$_2$(dtbbpy)](PF$_6$)) and 5 equivalents potassium hydrogen phosphate (K$_2$HPO$_4$) in dimethylformamide (DMF) at 30-35° C. for 72 hours to provide the decarboxylated compound (compound 4).

Introduction of a hydroxy moiety in the compound was achieved by derivation of the amine intermediate as shown in Scheme 5 below.

Scheme 5

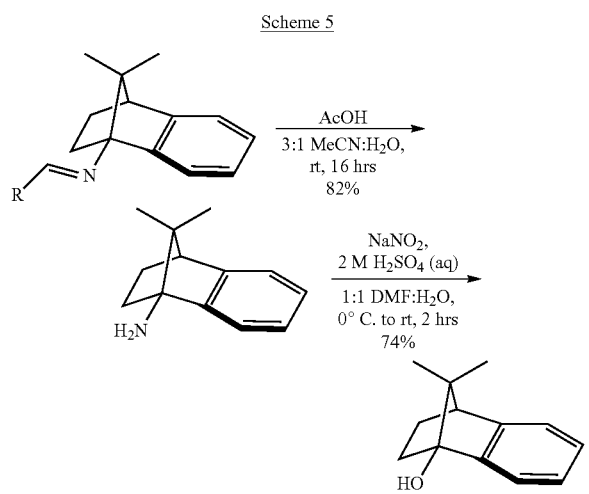

As shown in Scheme 5, the rearranged Schiff base was hydrolyzed in acetic acid in a mixture of acetonitrile and water (3:1 volume ratio), stirred at room temperature for 16 hours. The free amine was then reacted with sodium nitrate and 2 M sulfuric acid in a mixture of DMF and water (1:1 volume ratio), starting at 0° C. and warming to room temperature over 2 hours to provide a compound with a hydroxyl moiety. The resulting alcohol can then be acylated and, optionally, further functionalized, utilizing processes known in the art, to achieve a compound as disclosed herein having X as O.

Preparation of Acid Chloride A

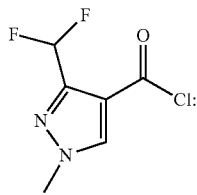

The above compound, acid chloride A, was prepared as follows:

3-(Difluoromethyl)-1-methyl-1H-pyrazole-4-carboxylic acid (106 mg, 0.60 mmol) was dissolved in 3.0 mL dry CH$_2$Cl$_2$, then cooled to 0° C. Oxalyl chloride (50 μL, 0.60 mmol) was added dropwise, followed by the addition of 5 μL dry DMF. The reaction mixture was stirred 10 min at 0° C. before removing the cold bath and stirring an additional 1.5 hrs at room temp; reaction vessel was vented periodically in first 30 min following DMF addition to account for gas evolution. This stock solution was suitable for use in any procedure that calls for acid chloride A. $^1$H NMR (CDCl$_3$, 500 MHz): δ=8.07 (s, 1H, pyr), 6.93 (t, 1H, J$_{CF}$=54.3 Hz, —CHF$_2$), 4.01 (s, 3H, —NMe) ppm.

Preparation of

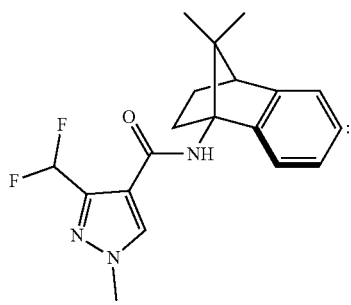

The above compound was prepared as follows:

Employing the general procedure outlined in Scheme 3, the requisite Schiff base-protected aminocyclopropane (78.5 mg) was dissolved in dry acetonitrile (2.5 mL), degassed with three freeze-pump-thaw cycles, and irradiated for 12 hrs while cooling with a fan. The crude reaction mixture was poured into 20 mL 1:1 saturated NaHCO$_3$ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (10% ethyl acetate:hexanes; loaded residue with PhMe). The desired Schiff base-protected compound was obtained.

Removal of the Schiff base protecting group was achieved by dissolving the protected compound (84.0 mg) in a 3:1 MeCN:H$_2$O mixture (0.6 mL:0.2 mL) before adding acetic acid (0.2 mL). The reaction mixture was flushed with argon gas, capped, and stirred at room temp for 20 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (13.1 mg) in dry dichloromethane (0.75 mL), followed by addition of the requisite carboxylic acid (18.5 mg), DMAP (13 mg), and EDC.HCl (20 mg), respectively. The reaction was flushed with argon gas, capped, and stirred at room temp 14 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+ 1% triethylamine mobile phase). The final compound was obtained. $^1$H NMR (CDCl$_3$, 500 MHz): δ=8.02 (s, 1H, pyrazole), 7.24-7.21 (m, 1H, Ar), 7.13-7.09 (m, 3H, Ar), 6.82 (t, 1H, J$_{CF}$=54.2 Hz, —CHF$_2$), 6.69 (br s, 1H, —NH), 3.94 (s, 3H, pyrazole —NMe), 2.80 (d, 1H, J=3.7 Hz, C4), 2.41-2.35 (m, 1H, C2-eq.), 2.25-2.19 (m, 2H, C3-eq, C2-ax), 1.32-1.26 (m, 1H, C3-ax), 1.13 (s, 3H, C7-Me), 0.68 (s, 3H, C7-Me) ppm; HRMS (ES+, m/z) calculated for $C_{19}H_{22}F_2N_3O^+$: 346, Found: 346.

Preparation of

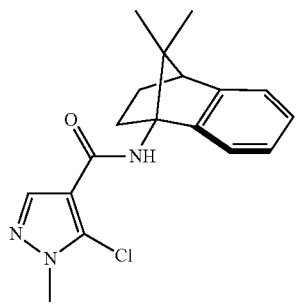

:

The above compound was prepared as follows:

The aminated compound, as obtained using the steps described in paragraphs [0079]-[0080] was acylated by dissolving the starting material (14.0 mg) in dry dichloromethane, followed by addition of the requisite carboxylic acid (18 mg), DMAP (14 mg), and EDC.HCl (21.5 mg), respectively. The reaction was flushed with argon gas, capped, and stirred at room temp. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+1% triethylamine mobile phase). The desired compound was obtained. $^1$H NMR (CDC$_3$, 500 MHz): δ=8.03 (s, 1H, pyrazole), 7.23-7.20 (m, 1H, Ar), 7.14-7.10 (m, 3H, Ar), 6.39 (br s, 1H, —NH), 3.90 (s, 3H, pyrazole —NMe), 2.83 (d, 1H, J=4.1 Hz, C4), 2.45 (ddd, 1H, J=12.3, 10.2, 4.0 Hz, C2-eq.), 2.26-2.21 (m, 1H, C3-eq), 2.16 (ddd, 1H, J=14.6, 9.2, 4.2 Hz, C2-ax), 1.30 (ddd, 1H, J=12.5, 9.5, 4.1 Hz, C3-ax), 1.15 (s, 3H, C7-Me), 0.70 (s, 3H, C7-Me) ppm; HRMS (ES+, m/z) calculated for $C_{18}H_{22}ClN_3O^+$: 330, Found: 330.

Preparation of and

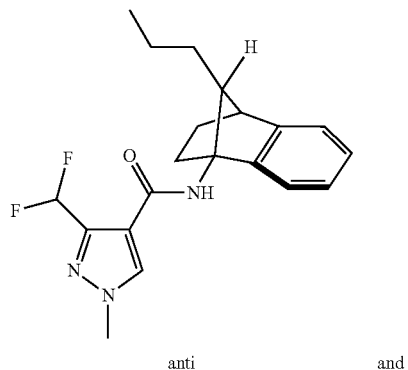

anti and

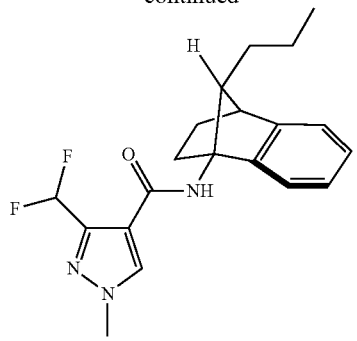

syn :

The above compounds were prepared as follows:

Employing the general procedure outlined in Scheme 3, the requisite Schiff base-protected aminocyclopropane (67.8 mg) was dissolved in dry acetonitrile (2.0 mL), degassed with three freeze-pump-thaw cycles, and irradiated for 8 hrs while cooling with a fan. The crude reaction mixture was poured into 20 mL 1:1 saturated NaHCO$_3$ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (2 to 3 to 5 to 7 to 10 to 15 to 25 to 35% ethyl acetate:hexanes; loaded residue with PhMe). The desired Schiff base-protected compound was obtained.

Removal of the Schiff base protecting group was achieved by dissolving the protected compound (31.8 mg) in a 3:1 MeCN:H$_2$O mixture (0.6 mL:0.2 mL) before adding acetic acid (0.2 mL). The reaction mixture was flushed with argon gas, capped, and stirred at room temp for 24 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (13.9 mg) in dry dichloromethane, followed by addition of the requisite carboxylic acid (18 mg), DMAP (13 mg), and EDC.HCl (20 mg), respectively. The reaction was flushed with argon gas, capped, and stirred at room temp. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+1% triethylamine mobile phase). The desired compounds were obtained and the individual isomers were obtained through iterative chromatography and recrystallization protocols. syn isomer: $^1$H NMR (CDC₃, 500 MHz): δ=7.98 (s, 1H, pyrazole), 7.21-7.15 (m, 4H, Ar), 6.98 (br s, 1H, —NH), 6.85 (t, 1H, J$_{CF}$=54.2 Hz, —CHF₂), 3.95 (s, 3H, pyrazole —NMe), 3.18 (d, 1H, J=4.0 Hz, C4), 2.79 (app. td, 2H, J=11.0, 4.1 Hz, C7, C2-eq), 2.13 (app. tt, 1H, J=11.2, 4.3 Hz, C3-eq), 1.46 (ddd, 1H, J=11.3, 9.4, 4.4 Hz, C2-ax), 1.30-1.24 (m, 1H, C3-ax), 1.26-1.19 (m, 2H, C7-CH₂CH₂CH₃), 1.07-1.02 (m, 1H, C7-CH₂CH₂CH₃), 0.77 (t, 1H, J=7.4 Hz, C7-CH₂CH₂CH₃), 0.61 (dtd, 1H, J=13.6, 10.2, 5.4 Hz, C7-CH₂CH₂CH₃) ppm; HRMS (ES+, m/z) calculated for C$_{20}$H$_{24}$F$_2$N$_3$O$^+$: 360, Found: 360. anti isomer: ¹H NMR (CDCl₃, 500 MHz): δ=7.95 (s, 1H, pyrazole), 7.16-7.14 (m, 1H, Ar), 7.12-7.08 (m, 3H, Ar), 6.87 (t, 1H, J$_{CF}$=54.2 Hz, —CHF₂), 6.84 (br s, 1H, —NH), 3.91 (s, 3H, pyrazole —NMe), 3.15 (d, 1H, J=3.6 Hz, C4), 2.57 (dd, 1H, J=10.2, 2.6 Hz, C7), 2.07 (app. tt, 1H, J=11.5, 3.9 Hz, C3-eq), 2.00 (app. td, 1H, J=10.9, 3.8 Hz, C2-eq), 1.67-1.63 (m, 1H, C2-ax), 1.44-1.38 (m, 1H, C7-CH₂CH₂CH₃), 1.36-1.27 (m, 2H, C7-CH₂CH₂CH₃, C7-CH₂CH₂CH₃), 1.30-1.24 (m, 1H, C3-ax), 1.21-1.14 (m, 2H, C7-CH₂CH₂CH₃), 0.92 (t, 1H, J=7.1 Hz, C7-CH₂CH₂CH₃) ppm; HRMS (ES+, m/z) calculated for C$_{20}$H$_{24}$F$_2$N$_3$O$^+$: 360, Found: 360.
Preparation of

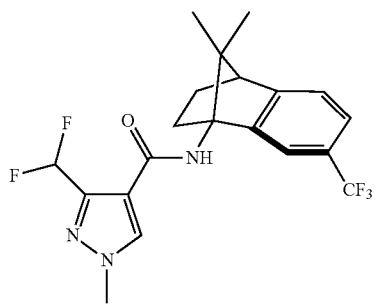

:

The above compound was prepared as follows:
Employing the general procedure outlined in Scheme 3, the requisite Schiff base-protected aminocyclopropane (72.8 mg) was dissolved in dry acetonitrile (2.2 mL), degassed with three freeze-pump-thaw cycles, and irradiated for 8 hrs while cooling with a fan. The crude reaction mixture was poured into 20 mL 1:1 saturated NaHCO₃ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (5 to 10 to 15 to 25% ethyl acetate:hexanes; loaded residue with PhMe). The desired Schiff base-protected compound was obtained.
Removal of the Schiff base protecting group was achieved by dissolving the protected compound (53.6 mg) in a 3:1 MeCN:H₂O mixture (0.9 mL:0.3 mL) before adding acetic acid (0.3 mL). The reaction mixture was flushed with argon gas, capped, and stirred at room temp for 18 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (16.5 mg) in 0.7 mL dry dichloromethane, followed by addition of the requisite carboxylic acid (16 mg), DMAP (13 mg), and EDC.HCl (19 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+1% triethylamine mobile phase). The desired compound was obtained. ¹H NMR (CDC₃, 500 MHz): δ=8.05 (s, 1H, pyrazole), 7.48 (app. s, 1H, Ar), 7.40 (d, 1H, J=7.6 Hz, Ar), 7.21 (d, 1H, J=7.6 Hz, Ar), 6.79 (t, 1H, J$_{CF}$=54.2 Hz, —CHF₂), 6.71 (br s, 1H, —NH), 3.95 (s, 3H, pyrazole —NMe), 2.88 (d, 1H, J=3.8 Hz, C4), 2.36-2.31 (m, 1H, C2-eq.), 2.29-2.23 (m, 2H, C3-eq, C2-ax), 1.31-1.25 (m, 1H, C3-ax), 1.14 (s, 3H, C7-Me), 0.68 (s, 3H, C7-Me) ppm; HRMS (ES+, m/z) calculated for C$_{20}$H$_{21}$F$_5$N$_3$O$^+$: 414, Found: 414.
Preparation of

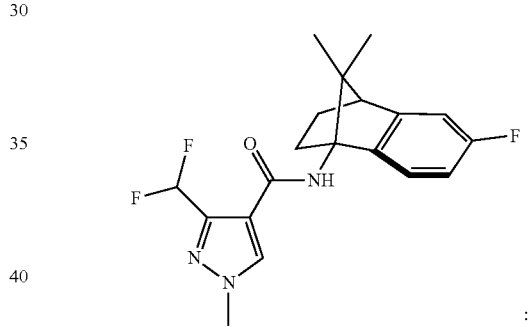

:

The above compound was prepared as follows:
Employing the general procedure outlined in Scheme 3, the requisite Schiff base-protected aminocyclopropane (69.5 mg) was dissolved in dry acetonitrile (2.0 mL), degassed with three freeze-pump-thaw cycles, and irradiated for 8 hrs while cooling with a fan. The crude reaction mixture was poured into 20 mL 1:1 saturated NaHCO₃ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (20 to 30 to 40% ethyl acetate:hexanes; loaded residue with PhMe). The desired Schiff base-protected compound was obtained.
Removal of the Schiff base protecting group was achieved by dissolving the protected compound (47.6 mg) in a 3:1 MeCN:H₂O mixture (0.9 mL:0.3 mL) before adding acetic acid (0.3 mL). The reaction mixture was flushed with argon gas, capped, and stirred at room temp for 18 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (14 mg) in 0.7 mL dry dichloromethane, followed by addition of the requisite carboxylic acid (16 mg), DMAP (13 mg), and EDC.HCl (19 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+1% triethylamine mobile phase). The desired compound was obtained. $^1$H NMR (CDC$_3$, 500 MHz): δ=8.01 (s, 1H, pyrazole), 7.16 (dd, 1H, J=8.1, 5.1 Hz, Ar), 6.85 (dd, 1H, J=8.4, 2.3 Hz, Ar), 6.80 (t, 1H, J$_{CF}$=54.2 Hz, —CHF$_2$), 6.77 (ddd, 1H, J=10.1, 8.1, 2.4 Hz, Ar), 6.68 (br s, 1H, —NH), 3.94 (s, 3H, pyrazole —NMe), 2.80 (d, 1H, J=3.7 Hz, C4), 2.34-2.29 (m, 1H, C2-eq.), 2.25-2.19 (m, 2H, C3-eq, C2-ax), 1.31-1.25 (m, 1H, C3-ax), 1.12 (s, 3H, C7-Me), 0.69 (s, 3H, C7-Me) ppm; HRMS (ES+, m/z) calculated for C$_{19}$H$_{21}$F$_3$N$_3$O$^+$: 364, Found: 364.
Preparation of

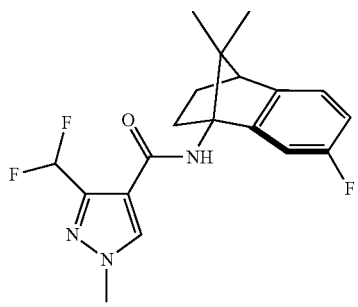

:

The above compound was prepared as follows:
Employing the general procedure outlined in Scheme 3, the requisite Schiff base-protected aminocyclopropane (64.7 mg) was dissolved in dry acetonitrile (2.0 mL), degassed with three freeze-pump-thaw cycles, and irradiated for 8 hrs while cooling with a fan. The crude reaction mixture was poured into 20 mL 1:1 saturated NaHCO$_3$ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (10% ethyl acetate:hexanes; loaded residue with PhMe). The desired Schiff base-protected compound was obtained.

Removal of the Schiff base protecting group was achieved by dissolving the protected compound (54.3 mg) in a 3:1 MeCN:H$_2$O mixture (0.9 mL:0.3 mL) before adding acetic acid (0.3 mL). The reaction mixture was flushed with argon gas, capped, and stirred at room temp for 24 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (12.6 mg) in 0.7 mL dry dichloromethane, followed by addition of the requisite carboxylic acid (16 mg), DMAP (11 mg), and EDC.HCl (18 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+1% triethylamine mobile phase). The desired compound was obtained. $^1$H NMR (CDC$_3$, 500 MHz): δ=8.02 (s, 1H, pyrazole), 7.03 (dd, 1H, J=7.9, 4.9 Hz, Ar), 6.98 (dd, 1H, J=8.5, 2.4 Hz, Ar), 6.81 (t, 1H, J$_{CF}$=54.2 Hz, —CHF$_2$), 6.77 (ddd, 1H, J=10.7, 8.1, 2.7 Hz, Ar), 6.68 (br s, 1H, —NH), 3.95 (s, 3H, pyrazole —NMe), 2.79 (d, 1H, J=3.9 Hz, C4), 2.32-2.19 (m, 3H, C2-eq, C3-eq, C2-ax), 1.27 (ddd, 1H, J=12.6, 8.9, 3.7 Hz, C3-ax), 1.11 (s, 3H, C7-Me), 0.69 (s, 3H, C7-Me) ppm; HRMS (ES+, m/z) calculated for C$_{19}$H$_{21}$F$_3$N$_3$O$^+$: 364, Found: 364.
Preparation of

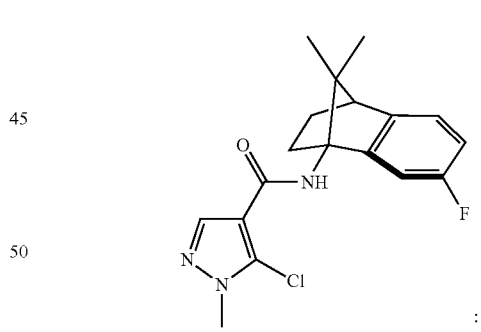

:

The aminated compound, as obtained using the methods described in paragraphs [0097]-[0098], was acylated by dissolving the starting material (14.2 mg) in dry dichloromethane, followed by addition of the requisite carboxylic acid (17 mg), DMAP (13 mg), and EDC.HCl (20 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+1% triethylamine mobile phase). The desired compound was obtained. $^1$H NMR (CDC$_3$, 500 MHz): δ=8.03 (s, 1H, pyrazole), 7.04 (dd, 1H, J=7.9, 4.9 Hz, Ar), 6.97 (dd, 1H, J=8.4, 2.3 Hz, Ar), 6.80-6.76 (m, 1H, Ar), 6.36 (br s, 1H, —NH), 3.91 (s, 3H, pyrazole —NMe), 2.81 (d, 1H, J=3.7 Hz, C4), 2.37-2.32 (m, 1H, C2-eq.), 2.25-2.19 (m, 2H, C3-eq, C2-ax), 1.30-1.25 (m, 1H, C3-ax), 1.13 (s, 3H, C7-Me), 0.71 (s, 3H, C7-Me) ppm; HRMS (ES+, m/z) calculated for $C_1H_{20}ClFN_3O^+$: 348, Found: 348.

Preparation of

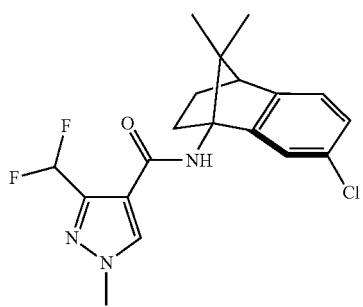

:

The above compound was prepared as follows:

Employing the general procedure outlined in Scheme 3, the requisite Schiff base-protected aminocyclopropane (59.9 mg) was dissolved in dry acetonitrile (1.7 mL), degassed with three freeze-pump-thaw cycles, and irradiated for 7 hrs while cooling with a fan. The crude reaction mixture was poured into 20 mL 1:1 saturated NaHCO$_3$ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (2 to 5 to 10 to 15% ethyl acetate:hexanes; loaded residue with PhMe). The desired Schiff base-protected compound was obtained.

Removal of the Schiff base protecting group was achieved by dissolving the protected compound (40.5 mg) in a 3:1 MeCN:H$_2$O mixture (0.75 mL:0.25 mL) before adding acetic acid (0.25 mL). The reaction mixture was flushed with argon gas, capped, and stirred at room temp for 24 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (13.3 mg) in 0.7 mL dry dichloromethane, followed by addition of the requisite carboxylic acid (16 mg), DMAP (11 mg), and EDC.HCl (18 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+1% triethylamine mobile phase). The desired compound was obtained. $^1$H NMR (CDC$_3$, 500 MHz): δ=8.04 (s, 1H, pyrazole), 7.23 (d, 1H, J=1.8 Hz, Ar), 7.08 (dd, 1H, J=7.7, 1.9 Hz, Ar), 7.03 (d, 1H, J=7.7 Hz, Ar), 6.80 (t, 1H, J$_{CF}$=54.2 Hz, —CHF$_2$), 6.67 (br s, 1H, —NH), 3.95 (s, 3H, pyrazole —NMe), 2.80 (d, 1H, J=4.0 Hz, C4), 2.31-2.25 (m, 2H, C2-eq, C3-eq), 2.25-2.19 (m, 1H, C2-ax), 1.16 (ddd, 1H, J=12.5, 10.7, 6.0 Hz, C3-ax), 1.11 (s, 3H, C7-Me), 0.69 (s, 3H, C7-Me) ppm; HRMS (ES+, m/z) calculated for $C_{19}H_{21}ClF_2N_3O^+$: 380, Found: 380.

Preparation of

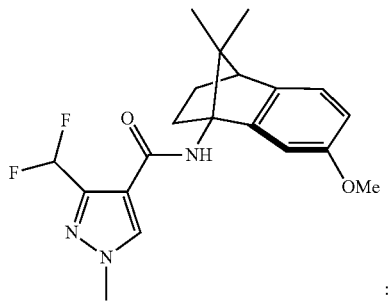

:

The above compound was prepared as follows:

Employing the general procedure outlined in Scheme 3, the Schiff base-protected aminocyclopropane (53.5 mg) was dissolved in dry acetonitrile (1.6 mL), degassed with three freeze-pump-thaw cycles, and irradiated for 6 hrs while cooling with a fan. The crude reaction mixture was poured into 20 mL 1:1 saturated NaHCO$_3$ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (10% ethyl acetate:hexanes; loaded residue with PhMe). The desired Schiff base-protected compound was obtained.

Removal of the Schiff base protecting group was achieved by dissolving the protected compound (37.2 mg) in a 3:1 MeCN:H$_2$O mixture (0.75 mL:0.25 mL) before adding acetic acid (0.25 mL). The reaction mixture was flushed with argon gas, capped, and stirred at room temp for 24 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (18.9 mg) in 0.9 mL dry dichloromethane, followed by addition of the requisite carboxylic acid (23 mg), DMAP (16 mg), and EDC.HCl (25 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (30 to 50 to 80% ethyl acetate:pentane; loaded residue with PhMe; silica was pre-neutralized with a 30% ethyl acetate:pentane+1% triethylamine mobile phase). The desired compound was obtained. $^1$H NMR (CDCl$_3$, 500 MHz): δ=8.01 (s, 1H, pyrazole), 7.01 (d, 1H, J=7.9 Hz, Ar), 6.85 (d, 1H, J=1.5 Hz, Ar), 6.81 (t, 1H, J$_{CF}$=54.2 Hz, —CHF$_2$), 6.64 (br s, 1H, —NH), 6.62 (dd, 1H, J=8.0, 1.9 Hz, Ar), 3.94 (s, 3H, pyrazole —NMe), 3.76 (s, 3H, —OMe), 2.75 (d, 1H, J=4.1 Hz, C4), 2.43-2.38 (m, 1H, C2-eq.), 2.23-2.17 (m, 2H, C3-eq, C2-ax), 1.30-1.25 (m, 1H, C3-ax), 1.11 (s, 3H, C7-Me), 0.69 (s, 3H, C7-Me) ppm; HRMS (ES+, m/z) calculated for C$_{20}$H$_{24}$F$_2$N$_3$O$_2$$^+$: 376, Found: 376.

Preparation of

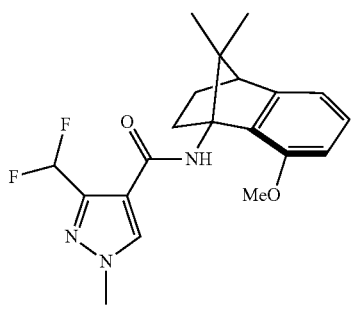

:

Employing the general procedure outlined in Scheme 3, the Schiff base-protected aminocyclopropane (68.7 mg) was dissolved in dry acetonitrile (2.0 mL), degassed with three freeze-pump-thaw cycles, and irradiated for 8 hrs while cooling with a fan. The crude reaction mixture was poured into 20 mL 1:1 saturated NaHCO$_3$ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (10 to 70% ethyl acetate:hexanes, increasing in 10% increments; loaded residue with PhMe). The desired Schiff base-protected compound was obtained.

Removal of the Schiff base protecting group was achieved by dissolving the protected compound (21.3 mg) in a 3:1 MeCN:H$_2$O mixture (0.45 mL:0.15 mL) before adding acetic acid (0.15 mL). The reaction mixture was flushed with argon gas, capped, and stirred at room temp for 60 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (14.2 mg) in 0.7 mL dry dichloromethane, followed by addition of the requisite carboxylic acid (17 mg), DMAP (12 mg), and EDC.HCl (19 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (20 to 100% ethyl acetate:pentane, increasing in 20% increments; loaded residue with PhMe; silica was pre-neutralized with a 20% ethyl acetate:pentane+1% triethylamine mobile phase). The desired compound was obtained. $^1$H NMR (CDCl$_3$, 500 MHz): δ=7.82 (s, 1H, pyrazole), 7.34 (br s, 1H, —NH), 7.10 (dd, 1H, J=8.1, 7.4 Hz, Ar), 7.00 (t, 1H, J$_{CF}$=54.2 Hz, —CHF$_2$), 6.79 (d, 1H, J=7.2 Hz, Ar), 6.71 (d, 1H, J=7.2 Hz, Ar), 3.96 (s, 3H, pyrazole —NMe), 3.76 (s, 3H, —OMe), 3.16 (ddd, 1H, J=12.1, 10.3, 4.0 Hz, C2-eq), 2.72 (d, 1H, J=4.1 Hz, C4), 1.87 (app. ddt, 1H, J=12.1, 10.3, 4.1 Hz, C3-eq), 1.66 (ddd, 1H, J=12.8, 8.4, 3.7 Hz, C2-ax), 1.20 (s, 3H, C7-Me), 1.21-1.18 (m, 1H, C3-ax), 0.73 (s, 3H, C7-Me) ppm; HRMS (ES+, m/z) calculated for C$_{20}$H$_{24}$F$_2$N$_3$O$_2$$^+$: 376, Found: 376.

Preparation of

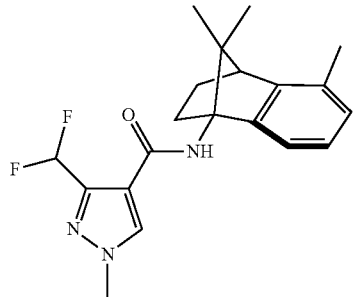

:

Employing the general procedure outlined in Scheme 3, the Schiff base-protected aminocyclopropane (47.4 mg) was dissolved in dry acetonitrile (1.5 mL), degassed with three freeze-pump-thaw cycles, and irradiated for 6 hrs while cooling with a fan. The crude reaction mixture was poured into 20 mL 1:1 saturated NaHCO$_3$ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (8% ethyl acetate:hexanes; loaded residue with PhMe). The desired Schiff base-protected compound was obtained.

Removal of the Schiff base protecting group was achieved by dissolving the protected compound (33.9 mg) in a 3:1 MeCN:H$_2$O mixture (0.75 mL:0.25 mL) before adding acetic acid (0.25 mL). The reaction mixture was flushed with argon gas, capped, and stirred at room temp for 24 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (20.3 mg) in 1.0 mL dry dichloromethane, followed by addition of the requisite carboxylic acid (27 mg), DMAP (18 mg), and EDC.HCl (29 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+1% triethylamine mobile phase) to provide the desired compound. $^1$H NMR (CDC$_3$, 500 MHz): δ=8.01 (s, 1H, pyrazole), 7.05 (d, 1H, J=7.3 Hz, Ar), 7.01 (app. t, 1H, J=7.4 Hz, Ar), 6.93 (d, 1H, J=7.5 Hz, Ar), 6.81 (t, 1H, J$_{CF}$=54.2 Hz, —CHF$_2$), 6.67 (br s, 1H, —NH), 3.95 (s, 3H, pyrazole —NMe), 2.91 (d, 1H, J=3.8 Hz, C4), 2.44-2.39 (m, 1H, C2-eq.), 2.27 (s, 3H, C11-Me), 2.24-2.16 (m, 2H, C3-eq, C2-ax), 1.27-1.22 (m, 1H, C3-ax), 1.13 (s, 3H, C7-Me), 0.68 (s, 3H, C7-Me) ppm; HRMS (ES+, m/z) calculated for C$_{20}$H$_{24}$F$_2$N$_3$O$^+$: 360, Found: 360.
Preparation of

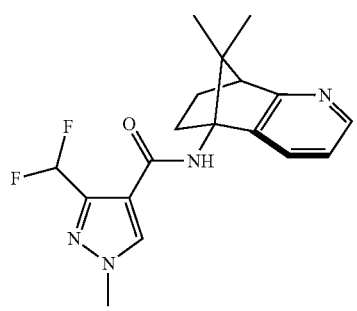

Employing the general procedure outlined in Scheme 3, the Schiff base-protected aminocyclopropane (69.3 mg) was dissolved in dry acetonitrile (2.2 mL), degassed with three freeze-pump-thaw cycles, and irradiated for 8.5 hrs while cooling with a fan. The crude reaction mixture was poured into 20 mL 1:1 saturated NaHCO$_3$ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (10 to 20 to 40 to 60 to 80 to 100% ethyl acetate:hexanes; loaded residue with PhMe). The desired Schiff base-protected compound was obtained.

Removal of the Schiff base protecting group was achieved by dissolving the protected compound (46.9 mg) in a 3:1 MeCN:H$_2$O mixture (0.9 mL:0.3 mL) before adding acetic acid (0.3 mL). The reaction mixture was flushed with argon gas, capped, and stirred at room temp for 24 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (12.5 mg) in 0.7 mL dry dichloromethane, followed by addition of the requisite carboxylic acid (18 mg), DMAP (12 mg), and EDC.HCl (19 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (5 to 10 to 20 to 30 to 50 to 75% acetone:dichloromethane; loaded residue with PhMe; silica was pre-neutralized with a 5% acetone:dichloromethane+1% triethylamine mobile phase). The desired compound was obtained. $^1$H NMR (CDC$_3$, 500 MHz): δ=8.23 (dd, 1H, J=5.1, 1.1 Hz, pyridine), 8.01 (s, 1H, pyrazole), 7.52 (d, 1H, J=6.8 Hz, pyridine), 7.01 (dd, 1H, J=7.3, 5.3 Hz, pyridine), 6.80 (t, 1H, J$_{CF}$=54.2 Hz, —CHF$_2$), 6.75 (br s, 1H, —NH), 3.95 (s, 3H, pyrazole —NMe), 2.93 (d, 1H, J=3.2 Hz, C4), 2.32-2.23 (m, 3H, C2-eq, C3-eq, C2-ax), 1.44-1.33 (m, 1H, C3-ax), 1.15 (s, 3H, C7-Me), 0.72 (s, 3H, C7-Me) ppm; HRMS (ES+, m/z) calculated for C$_{18}$H$_{21}$F$_2$N$_4$O$^+$: 347, Found: 347.
Preparation of

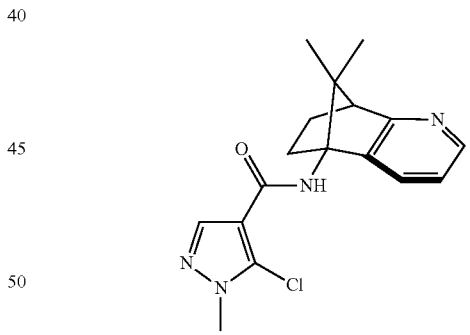

The above compound was prepared as follows:
The aminated compound, obtained using the steps described in paragraphs [00115]-[00116], was acylated by dissolving the starting material (12.4 mg) in 0.7 mL dry dichloromethane, followed by addition of the requisite carboxylic acid (16 mg), DMAP (12 mg), and EDC.HCl (19 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (5 to 10 to 20 to 30 to 50 to 75% acetone:dichloromethane; loaded residue with PhMe; silica was pre-neutralized with a 5% acetone:dichloromethane+1% triethylamine mobile phase). The desired compound was obtained. ¹H NMR (CDCl₃, 500 MHz): δ=8.24 (dd, 1H, J=5.2, 1.1 Hz, pyridine), 8.03 (s, 1H, pyrazole), 7.53 (d, 1H, J=7.3 Hz, pyridine), 7.02 (dd, 1H, J=7.3, 5.2 Hz, pyridine), 6.43 (br s, 1H, —NH), 3.91 (s, 3H, pyrazole —NMe), 2.96 (d, 1H, J=3.7 Hz, C4), 2.31-2.22 (m, 3H, C2-eq, C3-eq, C2-ax), 1.42-1.37 (m, 1H, C3-ax), 1.17 (s, 3H, C7-Me), 0.75 (s, 3H, C7-Me) ppm; HRMS (ES+, m/z) calculated for $C_{17}H_{20}ClN_4O^+$: 331, Found: 331.

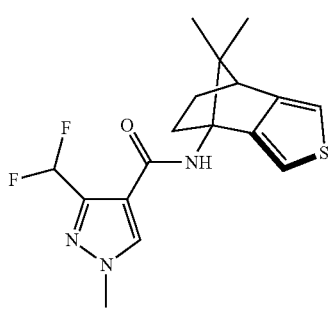

Preparation of

The above compound was prepared as follows:

Employing the general procedure outlined in Scheme 3, the Schiff base-protected aminocyclopropane (50.0 mg) was dissolved in dry acetonitrile (1.6 mL), degassed with three freeze-pump-thaw cycles, and irradiated for 7 hrs while cooling with a fan. The crude reaction mixture was poured into 20 mL 1:1 saturated NaHCO₃ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (1 to 3 to 5 to 10% ethyl acetate:hexanes; loaded residue with PhMe). The desired Schiff base-protected compound was obtained.

Removal of the Schiff base protecting group was achieved by dissolving the protected compound (46.2 mg) in a 3:1 MeCN:H₂O mixture (0.9 mL:0.3 mL) before adding acetic acid (0.3 mL). The reaction mixture was flushed with argon gas, capped, and stirred at room temp for 24 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (10.6 mg) in 0.6 mL dry dichloromethane, followed by addition of the requisite carboxylic acid (15 mg), DMAP (10 mg), and EDC.HCl (16 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (20 to 100% ethyl acetate:pentane, increasing in 20% increments; loaded residue with PhMe; silica was pre-neutralized with a 20% ethyl acetate:pentane+1% triethylamine mobile phase). The desired compound was obtained. ¹H NMR (CDC₃, 500 MHz): δ=8.00 (s, 1H, pyrazole), 6.90 (d, 1H, J=2.0 Hz, thiophene), 6.80 (t, 1H, $J_{CF}$=54.2 Hz, —CHF₂), 6.71 (d, 1H, J=2.1 Hz, thiophene), 6.66 (br s, 1H, —NH), 3.93 (s, 3H, pyrazole —NMe), 2.78 (d, 1H, J=3.9 Hz, C4), 2.34-2.28 (m, 1H, C2-eq), 2.26-2.22 (m, 1H, C3-eq), 2.23-2.18 (m, 1H, C2-ax), 1.43-1.37 (m, 1H, C3-ax), 1.12 (s, 3H, C7-Me), 0.72 (s, 3H, C7-Me) ppm; HRMS (ES+, m/z) calculated for $C_{17}H_{20}F_2N_3OS^+$: 352, Found: 352.

Preparation of

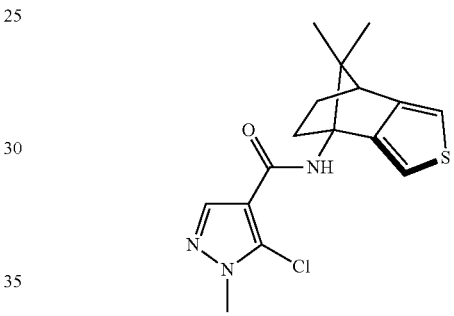

The above compound was prepared as follows:

The aminated compound, as obtained using the steps described in paragraphs [00122]-[00123], was acylated by dissolving the starting material (12.0 mg) in 0.7 mL dry dichloromethane, followed by addition of the requisite carboxylic acid (15 mg), DMAP (11 mg), and EDC.HCl (18 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+1% triethylamine mobile phase). The final compound was. ¹H NMR (CDCl₃, 500 MHz): δ=8.01 (s, 1H, pyrazole), 6.90 (d, 1H, J=1.9 Hz, thiophene), 6.72 (d, 1H, J=2.1 Hz, thiophene), 6.35 (br s, 1H, —NH), 3.89 (s, 3H, pyrazole —NMe), 2.80 (d, 1H, J=3.9 Hz, C4), 2.35-2.17 (m, 3H, C2-eq, C3-eq, C2-ax), 1.44-1.37 (m, 1H, C3-ax), 1.14 (s, 3H, C7-Me), 0.74 (s, 3H, C7-Me) ppm; HRMS (ES+, m/z) calculated for $C_{16}H_{19}ClN_3OS^+$: 336, Found: 336.

Preparation of

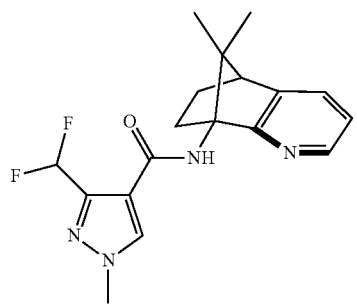

:

The above compound was prepared as follows:

Employing the general procedure outlined in Scheme 3, the requisite Schiff base-protected aminocyclopropane (58.0 mg) was dissolved in dry acetonitrile (1.8 mL), degassed with three freeze-pump-thaw cycles, and irradiated for 8 hrs while cooling with a fan. The crude reaction mixture was poured into 20 mL 1:1 saturated NaHCO$_3$ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (30 to 50 to 75 to 100% ethyl acetate:hexanes; loaded residue with PhMe). The desired Schiff base-protected compound was obtained.

Removal of the Schiff base protecting group was achieved by dissolving the protected compound (20.2 mg) in a 3:1 MeCN:H$_2$O mixture (0.45 mL:0.15 mL) before adding acetic acid (0.15 mL). The reaction mixture was flushed with argon gas, capped, and stirred at room temp for 60 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (7.9 mg) in 0.5 mL dry dichloromethane, followed by addition of the requisite carboxylic acid (11 mg), DMAP (8 mg), and EDC.HCl (12 mg), respectively. The reaction was flushed with argon gas, capped, and stirred at room temp 16 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (5 to 10 to 15 to 25 to 35 to 50% acetone:dichloromethane; loaded residue with PhMe; silica was pre-neutralized with a 5% acetone:dichloromethane+1% triethylamine mobile phase). The desired compound was obtained. $^1$H NMR (CDC$_3$, 500 MHz): δ=8.26 (dd, 1H, J=5.3, 1.0 Hz, pyridine), 7.94 (s, 1H, pyrazole), 7.43 (d, 1H, J=7.3 Hz, pyridine), 7.07 (br s, 1H, —NH), 7.09-7.05 (m, 1H, pyridine), 7.04 (t, 1H, J$_{CF}$=54.2 Hz, —CHF$_2$), 3.96 (s, 3H, pyrazole —NMe), 3.29 (ddd, 1H, J=12.2, 10.7, 3.9 Hz, C2-eq), 2.85 (d, 1H, J=3.2 Hz, C4), 2.35 (app. dt, 1H, J=10.5, 4.2 Hz, C3-eq), 1.47 (ddd, 1H, J=12.4, 9.6, 4.4 Hz, C2-ax), 1.32 (s, 3H, C7-Me), 1.29 (ddd, 1H, J=12.4, 9.6, 4.1 Hz, C3-ax), 0.61 (s, 3H, C7-Me) ppm; HRMS (ES+, m/z) calculated for C$_{18}$H$_{21}$F$_2$N$_4$O$^+$: 347, Found: 347.

Preparation of and

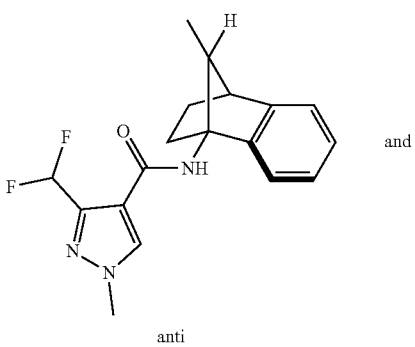

and anti

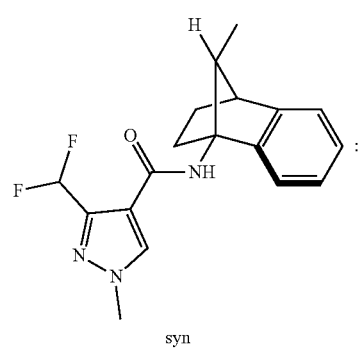

:

syn

The above compounds were prepared as follows:

Employing the general procedure outlined in Scheme 3, the requisite Schiff base-protected aminocyclopropane (50.1 mg) was dissolved in dry acetonitrile (1.7 mL), degassed with three freeze-pump-thaw cycles, and irradiated for 7 hrs while cooling with a fan. The crude reaction mixture was poured into 20 mL 1:1 saturated NaHCO$_3$ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (1 to 3 to 5 to 10 to 15% ethyl acetate:hexanes; loaded residue with PhMe). The desired Schiff base-protected compound was obtained.

Removal of the Schiff base protecting group was achieved by dissolving the protected compound (20.8 mg) in a 3:1

MeCN:H₂O mixture (0.6 mL:0.2 mL) before adding acetic acid (0.2 mL). The reaction mixture was flushed with argon gas, capped, and stirred at room temp for 24 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (11.0 mg) in 0.7 mL dry dichloromethane, followed by addition of the requisite carboxylic acid (17 mg), DMAP (12 mg), and EDC.HCl (18 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (20 to 100% ethyl acetate:pentane, increasing in 20% increments; loaded residue with PhMe; silica was pre-neutralized with a 20% ethyl acetate:pentane+1% triethylamine mobile phase). The desired compounds were obtained and the isomers were isolated through iterative chromatography and recrystallization protocols. syn isomer: ¹H NMR (CDCl₃, 500 MHz): δ=7.98 (s, 1H, pyrazole), 7.21-7.16 (m, 4H, Ar), 6.97 (br s, 1H, —NH), 6.85 (t, 1H, $J_{CF}$=54.2 Hz, —CHF₂), 3.95 (s, 3H, pyrazole —NMe), 3.06 (d, 1H, J=4.3 Hz, C4), 2.90 (quart., 1H, J=6.8 Hz, C7), 2.73 (app. td, 1H, J=11.0, 4.1 Hz, C2-eq), 2.15 (app. tt, 1H, J=11.2, 4.3 Hz, C3-eq), 1.55-1.49 (m, 1H, C2-ax), 1.30-1.24 (m, 1H, C3-ax), 0.59 (d, 1H, J=6.6 Hz, C7-Me) ppm; HRMS (ES+, m/z) calculated for $C_{18}H_{20}F_2N_3O^+$: 332, Found: 332. anti isomer: ¹H NMR (CDC₃, 500 MHz): δ=7.95 (s, 1H, pyrazole), 7.16-7.08 (m, 4H, Ar), 6.85 (t, 1H, $J_{CF}$=54.2 Hz, —CHF₂), 6.82 (br s, 1H, —NH), 3.93 (s, 3H, pyrazole —NMe), 3.04 (d, 1H, J=2.7 Hz, C4), 2.68 (quart., 1H, J=6.7 Hz, C7), 2.17-2.09 (m, 1H, C3-eq), 2.00 (app. td, 1H, J=10.9, 3.6 Hz, C2-eq), 1.70-1.64 (m, 1H, C2-ax), 1.28-1.20 (m, 1H, C3-ax), 0.95 (d, 1H, J=6.8 Hz, C7-Me) ppm; HRMS (ES+, m/z) calculated for $C_{18}H_{20}F_2N_3O^+$: 332, Found: 332. Preparation of and

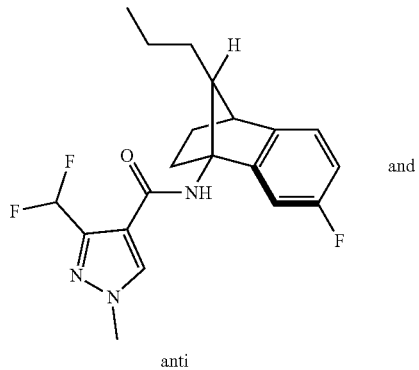

anti

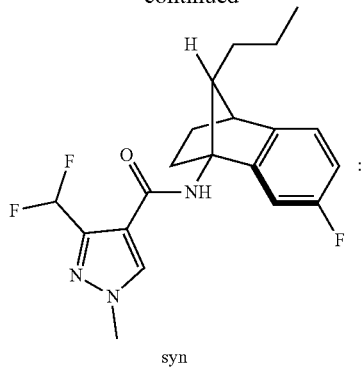

syn and

The above compounds were prepared as follows:

Employing the general procedure outlined in Scheme 3, the requisite Schiff base-protected aminocyclopropane (68.9 mg) was dissolved in dry acetonitrile (2.0 mL), degassed with three freeze-pump-thaw cycles, and irradiated for 8 hrs while cooling with a fan. The crude reaction mixture was poured into 20 mL 1:1 saturated NaHCO₃ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (8 to 40% ethyl acetate:hexanes, increasing in 8% increments; loaded residue with PhMe). The desired Schiff base-protected compound was obtained.

Removal of the Schiff base protecting group was achieved by dissolving the protected compound (43.2 mg) in a 3:1 MeCN:H₂O mixture (0.75 mL:0.25 mL) before adding acetic acid (0.25 mL). The reaction mixture was flushed with argon gas, capped, and stirred at room temp for 24 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was.

The aminated compound was acylated by dissolving the starting material (14.4 mg) in 0.7 mL dry dichloromethane, followed by addition of the requisite carboxylic acid (17 mg), DMAP (12 mg), and EDC.HCl (19 mg), respectively. The reaction was flushed with argon gas, capped, and stirred at room temp 18 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+1% triethylamine mobile phase). The desired compounds were obtained and the individual isomers were obtained through iterative chromatography and recrystallization protocols. syn isomer:

¹H NMR (CDCl₃, 500 MHz): δ=7.99 (s, 1H, pyrazole), 7.11 (dd, 1H, J=8.0, 4.9 Hz, Ar), 6.94-6.91 (m, 1H, Ar), 6.91 (br s, 1H, —NH), 6.85 (t, 1H, $J_{CF}$=54.2 Hz, —CHF₂), 6.83 (ddd, 1H, J=9.7, 7.6, 2.6 Hz, Ar), 3.95 (s, 3H, pyrazole —NMe), 3.16 (d, 1H, J=3.9 Hz, C4), 2.69 (app. td, 2H, J=11.1, 4.1 Hz, C7, C2-eq), 2.12 (app. tt, 1H, J=11.1, 4.2 Hz, C3-eq), 1.57 (ddd, 1H, J=11.0, 9.8, 4.2 Hz, C2-ax), 1.31-1.17 (m, 3H, C3-ax, C7-CH₂CH₂CH₃), 1.10-1.03 (m, 1H, C7-CH₂CH₂CH₃), 0.78 (t, 1H, J=7.3 Hz, C7-CH₂CH₂CH₃), 0.67-0.59 (m, 1H, C7-CH₂CH₂CH₃) ppm; HRMS (ES+, m/z) calculated for $C_{20}H_{23}F_3N_3O^+$: 378, Found: 378. anti isomer: ¹H NMR (CDCl₃, 500 MHz): δ=7.96 (s, 1H, pyrazole), 7.07 (dd, 1H, J=8.0, 4.9 Hz, Ar), 6.84 (t, 1H, $J_{CF}$=54.2 Hz, —CHF₂), 6.82 (dd, 1H, J=8.4, 2.4 Hz, Ar), 6.81 (br s, 1H, —NH), 6.77 (ddd, 1H, J=10.2, 8.0, 2.4 Hz, Ar), 3.94 (s, 3H, pyrazole —NMe), 3.14 (d, 1H, J=3.4 Hz, C4), 2.61 (dd, 1H, J=10.0, 2.3 Hz, C7), 2.07 (app. tt, 1H, J=11.5, 3.9 Hz, C3-eq), 1.97 (app. td, 1H, J=10.9, 3.7 Hz, C2-eq), 1.65-1.59 (m, 1H, C2-ax), 1.44-1.25 (m, 3H, C7-Pr), 1.23-1.11 (m, 1H, C3-ax, C7-CH₂CH₂CH₃), 0.91 (t, 1H, J=7.0 Hz, C7-CH₂CH₂CH₃) ppm; HRMS (ES+, m/z) calculated for $C_{20}H_{23}F_3N_3O^+$: 378, Found: 378.
Preparation of and

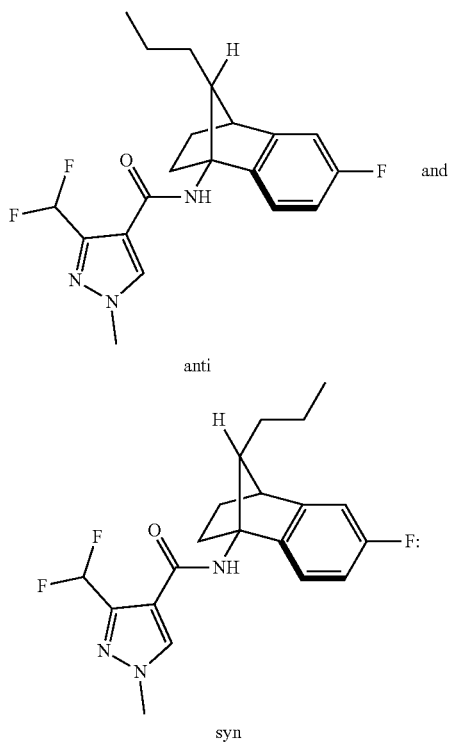

anti syn

The above compounds were prepared as follows:
Employing the general procedure outlined in Scheme 3, the requisite Schiff base-protected aminocyclopropane (68.8 mg) was dissolved in dry acetonitrile (2.0 mL), degassed with three freeze-pump-thaw cycles, and irradiated for 8 hrs while cooling with a fan. The crude reaction mixture was poured into 20 mL 1:1 saturated NaHCO₃ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (8 to 40% ethyl acetate:hexanes, increasing in 8% increments; loaded residue with PhMe). The desired Schiff base-protected compound was obtained.

Removal of the Schiff base protecting group was achieved by dissolving the protected compound (37.9 mg) in a 3:1 MeCN:H₂O mixture (0.75 mL:0.25 mL) before adding acetic acid (0.25 mL). The reaction mixture was flushed with argon gas, capped, and stirred at room temp for 24 hrs. The reaction was diluted with 2 mL water and 2 mL ether. The phases were separated, and the slightly acidic aqueous phase was washed with 2 mL ether two additional times. The aqueous phase was made basic through the addition of 0.5 mL of 6 M NaOH (aq.) then diluted with 2 mL ether. Phases were separated, and the aqueous phase was extracted with 3 portions of ether, 2 mL each. The organic phases from the basic extraction were combined, dried over anhydrous magnesium sulfate, filtered to remove solids, and concentrated under a stream of nitrogen. The desired aminated compound was obtained.

The aminated compound was acylated by dissolving the starting material (14.5 mg) in 0.7 mL dry dichloromethane, followed by addition of the requisite carboxylic acid (17 mg), DMAP (12 mg), and EDC.HCl (19 mg), respectively. The reaction was flushed with argon gas, capped, and stirred at room temp 18 hrs. The crude residue was diluted with 4 mL water and 2 mL ethyl acetate. The phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (15 to 75% ethyl acetate:pentane, increasing in 15% increments; loaded residue with PhMe; silica was pre-neutralized with a 15% ethyl acetate:pentane+1% triethylamine mobile phase). The desired compounds were obtained and the individual isomers were obtained through iterative chromatography and recrystallization protocols. syn isomer: ¹H NMR (CDC₃, 500 MHz): δ=7.98 (s, 1H, pyrazole), 7.11 (dd, 1H, J=8.0, 4.8 Hz, Ar), 6.93 (br s, 1H, —NH), 6.91 (dd, 1H, J=8.4, 2.3 Hz, Ar), 6.85 (ddd, 1H, J=10.1, 7.9, 2.4 Hz, Ar), 6.84 (t, 1H, $J_{CF}$=54.2 Hz, —CHF₂), 3.94 (s, 3H, pyrazole —NMe), 3.17 (d, 1H, J=4.0 Hz, C4), 2.72 (app. td, 2H, J=11.0, 4.1 Hz, C7, C2-eq), 2.13 (app. tt, 1H, J=10.9, 4.2 Hz, C3-eq), 1.54-1.49 (m, 1H, C2-ax), 1.31-1.18 (m, 3H, C3-ax, C7-CH₂CH₂CH₃), 1.10-1.02 (m, 1H, C7-CH₂CH₂CH₃), 0.79 (t, 1H, J=7.3 Hz, C7-CH₂CH₂CH₃), 0.67-0.59 (m, 1H, C7-CH₂CH₂CH₃) ppm; HRMS (ES+, m/z) calculated for $C_{20}H_{23}F_3N_3O^+$: 378, Found: 378. anti isomer: ¹H NMR (CDC₃, 500 MHz): δ=7.95 (s, 1H, pyrazole), 7.03 (dd, 1H, J=8.1, 5.0 Hz, Ar), 6.87 (dd, 1H, J=8.5, 2.3 Hz, Ar), 6.84 (t, 1H, $J_{CF}$=54.2 Hz, —CHF₂), 6.81 (br s, 1H, —NH), 6.77 (ddd, 1H, J=10.3, 8.1, 2.4 Hz, Ar), 3.94 (s, 3H, pyrazole —NMe), 3.14 (d, 1H, J=3.6 Hz, C4), 2.59 (d, 1H, J=10.1, 2.4 Hz, C7), 2.07 (app. tt, 1H, J=10.9, 3.9 Hz, C3-eq), 1.98 (app. td, 1H, J=10.8, 3.8 Hz, C2-eq), 1.66-1.60 (m, 1H, C2-ax), 1.44-1.26 (m, 3H, C7-Pr), 1.25-1.19 (m, 1H, C3-ax), 1.20-1.11 (m, 1H, C7-CH₂CH₂CH₃), 0.91 (t, 1H, J=7.0 Hz, C7-CH₂CH₂CH₃) ppm; HRMS (ES+, m/z) calculated for $C_{20}H_{23}F_3N_3O^+$: 378, Found: 378.

Preparation of

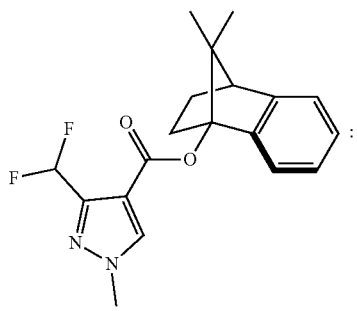

:

The above compound was prepared as follows:

In a dry vial under inert atmosphere, the requisite aminated compound (21.3 mg, 114 μmol) was dissolved in 300 μL dry DMF, then cooled to 0° C. Added 300 μL of 2 M H$_2$SO$_4$ (aq.). Prepared stock of NaNO$_2$ in HPLC-grade water to yield a stock concentration of 118 mg/600 μL (prepared 1.4 mL in total; 276 mg NaNO$_2$). The NaNO$_2$ stock was added (600 μL, 1.7 mmol) slowly down the side of the vial over the course of 3 min. The cold bath was removed, and the mixture was stirred at room temp for 2 hrs. Quenched by diluting with 2 mL ether then adding 2 mL of 3 M NaOH (aq.) slowly over 1 min followed by 500 μL sat. Na$_2$S$_2$O$_3$ (aq.). Phases were separated. The aqueous phase was extracted with three additional portions of 2 mL ether. Combined organics were dried over anhydrous magnesium sulfate, filtered to remove solids, and concentrated under a stream of nitrogen. Crude residue was purified via pipet chromatography over silica (5 to 10 to 20% ethyl acetate: pentane; loaded residue with PhMe). The desired hydroxylated compound was obtained.

The hydroxylated compound was acylated by dissolving the starting material (13.0 mg) in 0.75 mL dry dichloromethane, followed by addition of the requisite carboxylic acid (18 mg), DMAP (13 mg), and EDC.HCl (20 mg), respectively. The reaction was flushed with argon gas, capped, and stirred at 40° C. 24 hrs. The crude residue was diluted with 4 mL water and 2 mL ethyl acetate. Phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (3 to 6 to 10 to 15 to 25 to 35 to 50 to 75% ethyl acetate:pentane; loaded residue with PhMe; silica was pre-neutralized with a 3% ethyl acetate:pentane+1% triethylamine mobile phase). The desired compound was obtained. $^1$H NMR (CDCl$_3$, 500 MHz): δ=7.98 (s, 1H, pyrazole), 7.17 (d, 1H, J=6.9 Hz, Ar), 7.14 (t, 1H, J$_{CF}$=54.2 Hz, —CHF$_2$), 7.14-7.09 (m, 3H, Ar), 4.00 (s, 3H, pyrazole —NMe), 2.79 (d, 1H, J=4.1 Hz, C4), 2.35 (ddd, 1H, J=11.8, 9.5, 4.0 Hz, C2-eq), 2.27 (app. ddt, 1H, J=15.9, 11.9, 4.1 Hz, C3-eq), 2.18 (ddd, 1H, J=11.6, 10.6, 3.9 Hz, C2-ax), 1.35 (ddd, 1H, J=11.9, 9.8, 3.9 Hz, C3-ax), 1.18 (s, 3H, C7-Me), 0.73 (s, 3H, C7-Me) ppm; HRMS (ES+, m/z) calculated for C$_{19}$H$_{21}$F$_2$N$_2$O$_2$$^+$: 347, Found: 347.

Preparation of

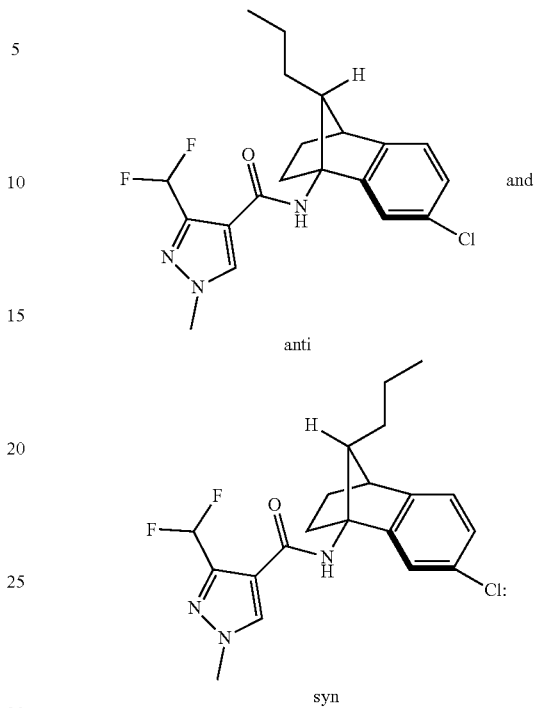

The above compounds were prepared as follows:

Employing the general procedure outlined in Scheme 3, the requisite Schiff base-protected aminocyclopropane (304 mg) was dissolved in dry acetonitrile (8.3 mL), degassed with three freeze-pump-thaw cycles, and irradiated for 16 hrs while cooling with a fan. The crude reaction mixture was poured into 20 mL 1:1 saturated NaHCO$_3$ (aq.):water and diluted with 10 mL ether. Phases were separated, and the aqueous phase was further extracted with 10 mL ether three times. Combined organics were washed with 10 mL brine, dried over anhydrous magnesium sulfate, filtered to remove solids, and concentrated in vacuo. The crude residue was purified via flash chromatography over basic alumina (5 to 10% ethyl acetate:hexanes; loaded residue with 1:1 PhMe: pentane), providing a mixture of starting material and the desired Schiff base-protected 1-aminonorbornane products.

The mixture of starting material and the desired Schiff base-protected 1-aminonorbornane products was exposed to a second irradiation following the procedure above, employing 6.5 mL dry MeCN and irradiating for 18 hrs. The crude reaction mixture was acidified via the addition of 50 μL 2 M HCl in MeOH. After 20 min at room temp, a freshly prepared stock of acid chloride A in 4.9 mL CH$_2$Cl$_2$ (0.97 mmol; see above for preparation). The vial was then flushed with Ar and sealed before heating to 50° C. for 1.5 hrs. Upon cooling to room temp, the reaction mixture was quenched by pouring into 50 mL of 1:1 sat. NaHCO$_3$:1 M NaOH, followed by dilution with 25 mL ethyl acetate. The phases were separated. The aqueous phase was extracted with three 25 mL portions of ethyl acetate. The combined organics were then washed with 50 mL brine containing 2 drops 6 M NaOH (aq.), dried over anhydrous magnesium sulfate, filtered to remove solids, and concentrated under vacuum. The crude residue was purified via flash chromatography over silica (10 to 70% ethyl acetate:hexanes, increasing in 10% increments; loaded crude residue with PhMe; silica was pre-neutralized by treatment with 10% ethyl acetate:hexanes+1% NEt$_3$). The products were obtained and collected separately, and further purified by successive recrystallizations from ethyl acetates:hexanes mixtures. syn isomer: $^1$H NMR (CDC$_3$, 500 MHz): δ=7.99 (s, 1H, pyrazole), 7.17 (d, 1H, J=1.5 Hz, Ar), 7.14 (dd, 1H, J=7.7, 1.8 Hz, Ar), 7.10 (d, 1H, J=7.7 Hz, Ar), 6.89 (br s, 1H, —NH), 6.85 (t, 1H, J$_{CF}$=54.2 Hz, —CHF$_2$), 3.95 (s, 3H, pyrazole —NMe), 3.16 (d, 1H, J=3.9 Hz, C4), 2.67 (app. td, 2H, J=11.2, 4.1 Hz, C7, C2-eq), 2.12 (app. tt, 1H, J=11.2, 4.3 Hz, C3-eq), 1.61 (ddd, 1H, J=11.5, 9.4, 4.4 Hz, C2-ax), 1.30-1.16 (m, 3H, C3-ax, C7-CH$_2$CH$_2$CH$_3$), 1.11-1.03 (m, 1H, C7-CH$_2$CH$_2$CH$_3$), 0.78 (t, 1H, J=7.3 Hz, C7-CH$_2$CH$_2$CH$_3$), 0.67-0.58 (m, 1H, C7-CH$_2$CH$_2$CH$_3$) ppm; HRMS (ES+, m/z) calculated for C$_{20}$H$_{23}$ClF$_2$N$_3$O$^+$: 394, Found: 394. anti isomer: $^1$H NMR (CDC$_3$, 500 MHz): δ=7.97 (s, 1H, pyrazole), 7.08-7.06 (m, 3H, Ar), 6.84 (t, 1H, J$_{CF}$=54.2 Hz, —CHF$_2$), 6.80 (br s, 1H, —NH), 3.94 (s, 3H, pyrazole —NMe), 3.14 (d, 1H, J=3.4 Hz, C4), 2.61 (d, 1H, J=9.9 Hz, C7), 2.07 (app. tt, 1H, J=11.4, 3.8 Hz, C3-eq), 2.00 (app. td, 1H, J=10.9, 3.7 Hz, C2-eq), 1.67-1.61 (m, 1H, C2-ax), 1.45-1.25 (m, 3H, C7-Pr), 1.24-1.13 (m, 1H, C3-ax, C7-CH$_2$CH$_2$CH$_3$), 0.91 (t, 1H, J=7.0 Hz, C7-CH$_2$CH$_2$CH$_3$) ppm; HRMS (ES+, m/z) calculated for C$_{20}$H$_{23}$ClF$_2$N$_3$O$^+$: 394, Found: 394.
Preparation of

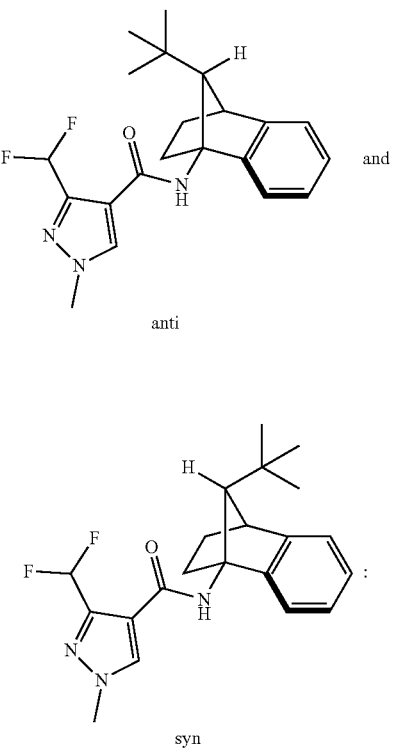

anti syn

The above compounds were prepared as follows:
Employing the general procedure outlined in Scheme 3, the requisite Schiff base-protected aminocyclopropane (305 mg) was dissolved in dry acetonitrile (8.8 mL), degassed with three freeze-pump-thaw cycles, and irradiated for 14 hrs while cooling with a fan. The crude reaction mixture was poured into 50 mL 1:1 saturated NaHCO$_3$ (aq.):water and diluted with 50 mL ether. Phases were separated, and the aqueous phase was further extracted with 25 mL ether three times. Combined organics were washed with 50 mL brine with 2 drops of 6 M NaOH added, dried over anhydrous magnesium sulfate, filtered to remove solids, and concentrated in vacuo. The crude residue was purified via flash chromatography over basic alumina (2 to 3 to 5 to 10 to 15% ethyl acetate:hexanes; loaded residue with 1:1 PhMe:pentane), providing the desired Schiff base-protected 1-aminonorbornane products.

Removal of the Schiff base protecting group was achieved by dissolving the protected compound (104 mg) in a 3:1 MeCN:H2O mixture (1.8 mL:0.6 mL) before adding acetic acid (0.6 mL). The reaction mixture was flushed with argon gas, capped, and stirred at room temp for 16 hrs. The reaction was diluted with 10 mL water and 10 mL ether. The phases were separated, and the slightly acidic aqueous phase was washed with 10 mL ether two additional times. The aqueous phase was made basic through the addition of 10 mL of 1 M NaOH (aq.) then diluted with 10 mL ether. Phases were separated, and the aqueous phase was extracted with 3 portions of ether, 10 mL each. The organic phases from the basic extraction were combined, dried over anhydrous magnesium sulfate, filtered to remove solids, and concentrated under a stream of nitrogen.

The 1-aminonorbornane mixture was acylated by dissolving the starting material (35.5 mg) in 1.7 mL dry dichloromethane, followed by addition of the requisite carboxylic acid (44 mg), DMAP (30 mg), and EDC.HCl (47 mg), respectively. The reaction was flushed with argon gas, capped, and stirred at room temp 16 hrs. The crude residue was diluted with 10 mL water and 10 mL ethyl acetate. Phases were separated, and the aqueous phase was extracted with 3 portions of ethyl acetate, 10 mL each. The organic phases were combined, dried over anhydrous magnesium sulfate, filtered to remove solids, and concentrated under a stream of nitrogen. The crude residue was purified with flash chromatography over silica (20 to 30 to 40 to 60 to 80% ethyl acetate:hexanes; loaded residue with PhMe; silica was pre-neutralized with a 20% ethyl acetate:pentane+1% triethylamine mobile phase). The desired compounds were obtained separately. Individual isomers were further purified through iterative chromatography and recrystallization protocols. syn isomer: $^1$H NMR (CDCl$_3$, 500 MHz): δ=7.99 (s, 1H, pyrazole), 7.23-7.13 (m, 4H, Ar), 7.16 (br s, 1H, —NH), 6.88 (t, 1H, J$_{CF}$=54.2 Hz, —CHF$_2$), 3.94 (s, 3H, pyrazole —NMe), 3.28 (app. td, 1H, J=9.9, 2.8 Hz, C2-eq), 3.27 (d, 1H, J=4.3 Hz, C4), 2.75 (d, 1H, J=0.7 Hz, C7), 2.10 (app. tt, 1H, J=11.5, 4.3 Hz, C3-eq), 1.19-1.08 (m, 2H, C2-ax, C3-ax), 0.61 (s, 9H, C7-tBu) ppm; HRMS (ES+, m/z) calculated for C$_{21}$H$_{26}$F$_2$N$_3$O$^+$: 374, Found: 374. anti isomer: $^1$H NMR (CDC$_3$, 500 MHz): δ=7.96 (s, 1H, pyrazole), 7.12-7.10 (m, 1H, Ar), 7.09-7.04 (m, 2H, Ar), 7.00-6.98 (m, 1H, Ar), 6.98 (br s, 1H, —NH), 6.88 (t, 1H, J$_{CF}$=54.2 Hz, —CHF$_2$), 3.93 (s, 3H, pyrazole —NMe), 3.32 (d, 1H, J=3.8 Hz, C4), 2.46 (s, 1H, C7), 2.32 (app. td, 1H, J=10.9, 3.6 Hz, C2-eq), 2.15 (app. tt, 1H, J=10.6, 4.2, C3-eq), 1.60-1.55 (m, 1H, C2-ax), 1.25-1.21 (m, 1H, C3-ax), 1.06 (s, 1H, C7-tBu) ppm; HRMS (ES+, m/z) calculated for C21H$_{26}$F$_2$N$_3$O$^+$: 374, Found: 374.

Preparation of

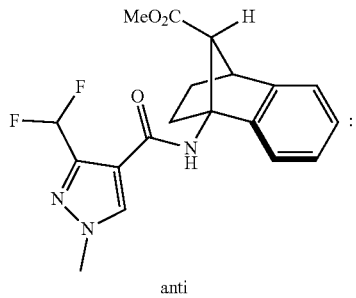

anti

The above compound was prepared as follows:

Employing the general procedure outlined in Scheme 3, the requisite Schiff base-protected aminocyclopropane (390 mg) was dissolved in 4 separate vials with dry acetonitrile (2.8 mL each vial), degassed with three freeze-pump-thaw cycles, and irradiated for 8 hrs with two 390 nm lamps while cooling with a fan. The crude reaction mixture was poured into 50 mL 1:1 saturated $NaHCO_3$ (aq.):water and diluted with 50 mL ether. Phases were separated, and the aqueous phase was further extracted with 25 mL ether three times. Combined organics were washed with 50 mL brine with 2 drops of 6 M NaOH added, dried over anhydrous magnesium sulfate, filtered to remove solids, and concentrated in vacuo. The crude residue was purified via flash chromatography over basic alumina (5 to 35% ethyl acetate:hexanes, increasing in 5% increments; loaded residue with PhMe), providing the anti Schiff base-protected 1-aminonorbornane product, as well as a mixture of anti and syn isomers.

Removal of the Schiff base protecting group (effective for either isomer individually, shown here with the mixture) was achieved by dissolving the protected compound (74 mg) in a 3:1 MeCN:H2O mixture (1.5 mL:0.5 mL) before adding acetic acid (0.5 mL). The reaction mixture was flushed with argon gas, capped, and stirred at room temp for 16 hrs. The reaction was diluted with 10 mL water and 10 mL ether. The phases were separated, and the slightly acidic aqueous phase was washed with 10 mL ether two additional times. The aqueous phase was made basic through the addition of 10 mL of 1 M NaOH (aq.) then diluted with 10 mL ether. Phases were separated, and the aqueous phase was extracted with 3 portions of ether, 10 mL each. The organic phases from the basic extraction were combined, dried over anhydrous magnesium sulfate, filtered to remove solids, and concentrated under a stream of nitrogen.

The 1-aminonorbornane mixture was acylated by dissolving the starting material (33.0 mg) in 1.5 mL dry dichloromethane, followed by addition of the requisite carboxylic acid (40 mg), DMAP (28 mg), and EDC.HCl (44 mg), respectively. The reaction was flushed with argon gas, capped, and stirred at room temp 16 hrs. The crude residue was diluted with 10 mL water and 10 mL ethyl acetate. Phases were separated, and the aqueous phase was extracted with 3 portions of ethyl acetate, 10 mL each. The organic phases were combined, dried over anhydrous magnesium sulfate, filtered to remove solids, and concentrated under a stream of nitrogen. The crude residue was purified with flash chromatography over silica (10 to 70% ethyl acetate:hexanes, increasing in 10% increments; loaded residue with PhMe; silica was pre-neutralized with a 10% ethyl acetate:pentane+1% triethylamine mobile phase). The desired compounds were obtained separately. Individual isomers were further purified through iterative chromatography and recrystallization protocols. The anti isomer was used in the preparation of the following compound. anti isomer: $^1$H NMR (CDCl$_3$, 500 MHz): δ=7.94 (s, 1H, pyrazole), 7.18-7.16 (m, 1H, Ar), 7.16-7.12 (m, 3H, Ar), 7.11 (br s, 1H, —NH), 6.92 (t, 1H, $J_{CF}$=54.2 Hz, —CHF$_2$), 3.93 (s, 3H, pyrazole —NMe), 3.67 (s, 3H, C7-CO$_2$Me), 3.60-3.58 (m, 2H, C4, C7), 2.27 (app. dt, 1H, J=14.9, 3.6 Hz, C2-eq.), 2.18 (app. td, 1H, J=10.9, 4.0 Hz, C3-eq), 1.73-1.67 (m, 1H, C2-ax), 1.33-1.28 (m, 1H, C3-ax) ppm; HRMS (ES+, m/z) calculated for $C_{19}H_{20}F_2N_3O_3^+$: 376, Found: 376.

Preparation of

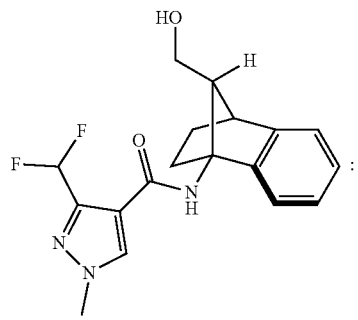

The above compound was prepared as follows:

The anti isomer from the above protocol (6.4 mg) was dissolved in 0.3 mL dry THF under inert atmosphere. This was added to a suspension of LiAlH$_4$ in 0.3 mL dry THF cooled to 0° C. The transfer was quantified with three 0.1 mL rinses with dry THF. Reaction mixture was heated to 40° C. for 7 hrs. Upon cooling to room temperature, the reaction mixture was slowly quenched with a mixture of 2 mL Rochelle salt with 2 mL 1 M NaOH in water and stirred for 30 min at room temperature. The mixture was diluted with 2 mL ether, then the phases were separated. The aqueous phase was extracted with 2 mL ethyl acetate three times. The combined organic phases were dried over anhydrous sodium sulfate, filtered to remove solids, and concentrated under vacuum. The desired 1-aminonorbornane protected intermediate was obtained The 1-aminonorbornane protected intermediate was acylated by dissolving the starting material (4.9 mg) in 0.5 mL dry dichloromethane, followed by addition of the requisite carboxylic acid (4.8 mg), DMAP (4.9 mg), and EDC.HCl (7.8 mg), respectively. The reaction was flushed with argon gas, capped, and stirred at room temp 16 hrs. The crude residue was diluted with 4 mL water and 2 mL ethyl acetate. The phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen to yield the bis-acylated material.

The bis-acylated species was selectively saponified by exposing to 0.4 mL ethanol, 0.4 mL water, and 94 mg KOH at 75° C. for 4 hrs. The crude mixture was diluted with 4 mL water and 2 mL ethyl acetate. The phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (2 to 10 to 25% acetone:ethyl acetate, with each increment containing 0.2% triethylamine). The desired compound was obtained. $^1$H NMR (CDCl$_3$, 500 MHz): δ=7.94 (s, 1H, pyrazole), 7.22 (d, 1H, J=6.2 Hz, Ar), 7.18 (br s, 1H, —NH), 7.18-7.12 (m, 3H, Ar), 6.91 (t, 1H, J$_{CF}$=8.8 Hz, —CHF$_2$), 3.94 (s, 3H, pyrazole —NMe), 3.81 (dd, 1H, J=11.1, 8.2 Hz, C7-CH$_2$OH), 3.66 (dd, 1H, J=11.0, 5.3 Hz, C7-CH$_2$OH), 3.21 (d, 1H, J=3.6 Hz, C4), 2.66 (t, 1H, J=6.7 Hz, C7), 2.34 (app. td, 1H, J=11.2, 4.0 Hz, C2-eq), 2.18 (br s, 1H, —OH), 2.10-2.04 (m, 1H, C3-eq), 1.69-1.64 (m, 1H, C2-ax), 1.30 (ddd, 1H, J=11.7, 9.5, 3.9 Hz, C3-ax) ppm; HRMS (ES+, m/z) calculated for C$_{18}$H$_{20}$F$_2$N$_3$O$_2^+$: 348, Found: 348.

Preparation of

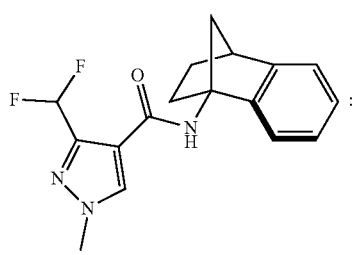

The above compound was prepared as follows:

The C7-CO$_2$Me species from above (21.4 mg) was saponified by dissolving in 0.3 mL THF, diluting with 0.3 mL 2 M NaOH (aq.), and heating to 60° C. for 4 hrs. After cooling to room temperature, the crude residue was diluted with 4 mL water and 2 mL 1:1 ethyl acetate:hexanes. The phases were separated, and the basic aqueous phase was washed with 2 portions of 1:1 ethyl acetate:hexanes, 2 mL each. The aqueous phase was acidified to pH=5 with 0.35 mL 2 M HCl (aq.), then diluted with 2 mL ethyl acetate. The phases were separated, and the acidic aqueous phase was extracted with 4 portions of ethyl acetate, 2 mL each. The organic phases were combined, dried over anhydrous magnesium sulfate, filtered to remove solids, and concentrated under a stream of nitrogen.

The C7-CO$_2$H species from the above transformation was dissolved in 0.3 mL isopropanol and 0.3 mL dry DMF prior to adding 1.6 mg of [Ir(dF[CF$_3$]ppy)$_2$(dtbbpy)](PF$_6$) and 50 mg potassium phosphate dibasic. The reaction mixture was degassed using three freeze-pump-thaw cycles. The reaction mixture was then irradiated with two 440 nm PR-160 Kessil lamps for 18 hrs while cooling with a fan. The crude reaction mixture was diluted with 4 mL water and 2 mL ethyl acetate. The phases were separated, and the aqueous phase was extracted with 3 portions of ethyl acetate, 2 mL each. The organic phases were combined, dried over anhydrous magnesium sulfate, filtered to remove solids, and concentrated under a stream of nitrogen. The crude residue was purified with flash chromatography over silica (40 to 70 to 100% ethyl acetate:pentane; loaded residue with PhMe; silica was pre-neutralized with a 40% ethyl acetate:pentane+1% triethylamine mobile phase). The desired compound was obtained. $^1$H NMR (CDCl$_3$, 500 MHz): δ=7.96 (s, 1H, pyrazole), 7.19-7.11 (m, 4H, Ar), 7.07 (br s, 1H, —NH), 6.90 (t, 1H, J$_{CF}$=8.8 Hz, —CHF$_2$), 3.94 (s, 3H, pyrazole —NMe), 3.35 (d, 1H, J=4.0 Hz, C4), 2.38 (app. td, 1H, J=11.0, 4.2 Hz, C2-eq), 2.24-2.22 (m, 1H, C7), 2.18-2.13 (m, 1H, C3-eq), 2.16-2.13 (m, 1H, C7), 1.59-1.54 (m, 1H, C2-ax), 1.34-1.29 (m, 1H, C3-ax) ppm; HRMS (ES+, m/z) calculated for C$_{17}$H$_{18}$F$_2$N$_3$O$^+$: 318, Found: 318.

Example 2: SHD Inhibition Assessment of Disclosed Compounds

The below compounds were evaluated against a panel of fungal pathogens isolated from several different crops from several locations across the Midwest United States.

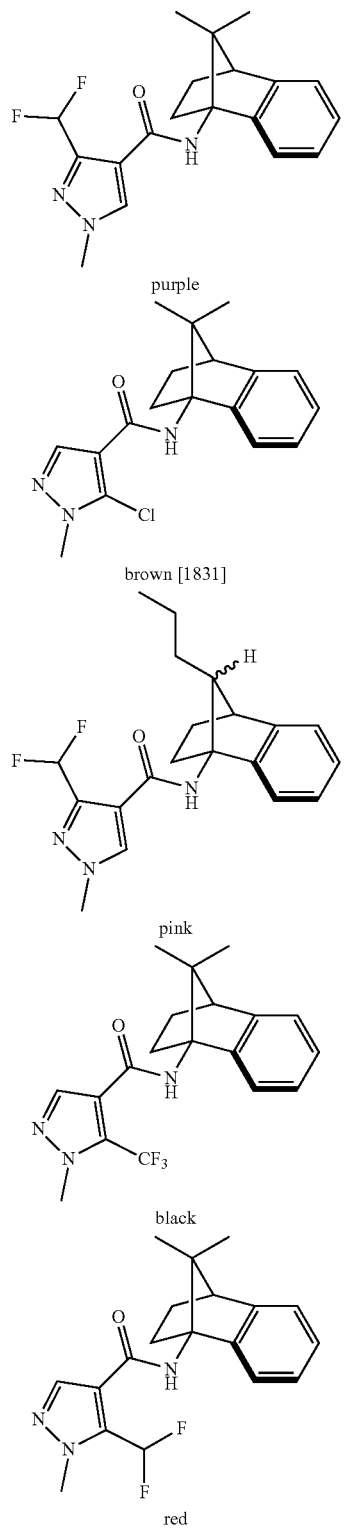

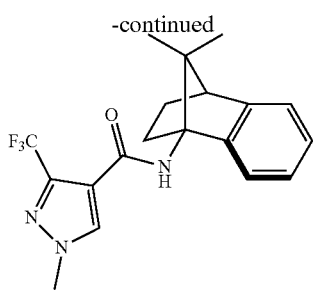

yellow

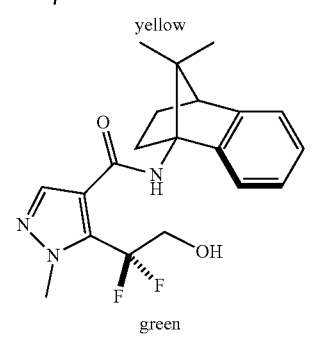

green

The inhibitory effects of these SDHI compounds were evaluated against the various pathogenic isolates grown on half-strength potato dextrose agar (PDA) amended with a given SDHI. SDHIs were formulated as 10,000 ppm stocks in DMSO. Inoculated media were prepared using a ratio of 12 g potato dextrose broth powder to 15 g agar to 1 L of deionized water. Upon autoclaving and cooling to 55° C., the media were inoculated with the SDHI compound of interest (1 mL of 10,000 ppm stock in 1 L media) then poured into plates. This method represented a 10 ppm trial for the SDHI compound. Mycelial plugs were cut from the leading growth of active fungal colonies (supported on full PDA media) and placed mycelia-down in the center of a plate. After an appropriate number of days (3-14 days, depending on pathogen), the radial growth was measured (average of three plates), and reported as the radial mycelial growth or as radial mycelial growth relative to a control. An analogous procedure was employed to determine the $EC_{50}$ value by varying the concentration of the initial SDHI compound DMSO stock. Ranges were adjusted based on compound potency, but in general, approximately 4 orders of magnitude were covered with 6-10 data points to generate the desired dose-response curve. The SDHI compounds were generally tested against a blank control, and in some cases, a positive control. The positive control was a commercially available SDHI fungicide known as fluxapyroxad.

Significantly, these SDHI compounds showed functional activity against four different pathogens when tested at 10 ppm, and in some cases provided growth inhibition greater than 50%, thus the $EC_{50}$ value for the compounds is <10 ppm. Notably, commercial, front-line fungicides for the tested fungal pathogens generally offer $EC_{50}$ values between 1-3 ppm, indicating the compounds of the disclosure are within an order of magnitude from the market standard.

Figure 4:
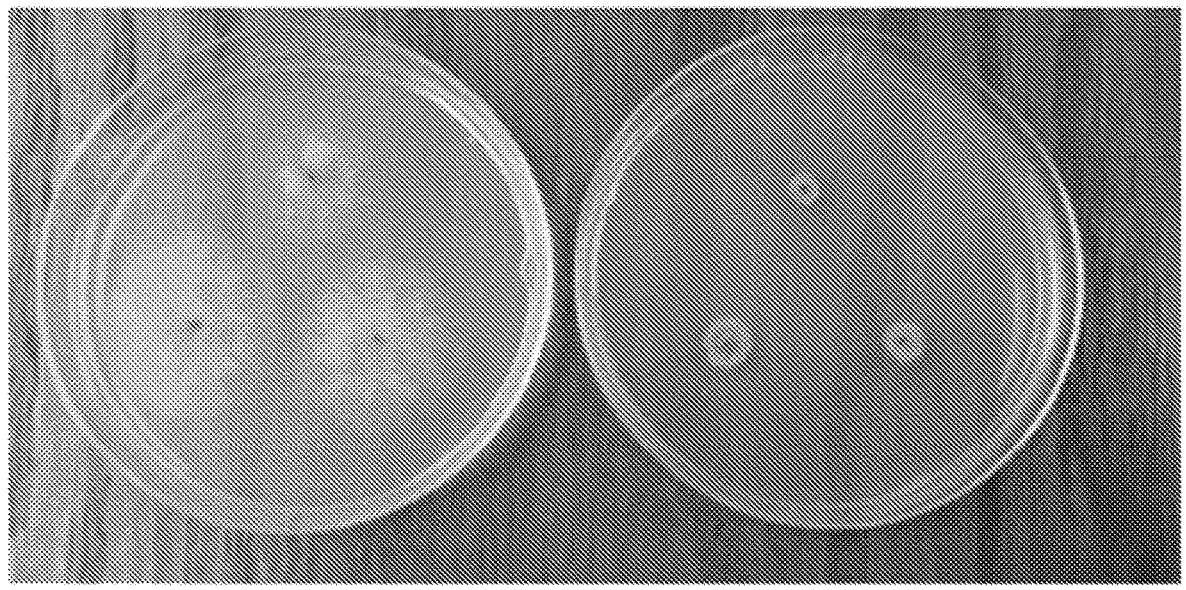
FIG. 4 depicts the fungicidal performance of a compound according to the disclosure ("1831") against *Monilinia fructicola* isolate against a blank control, as compared to fluxapyroxad, a commercially available fungicide ("fluxa").
Figure 4:
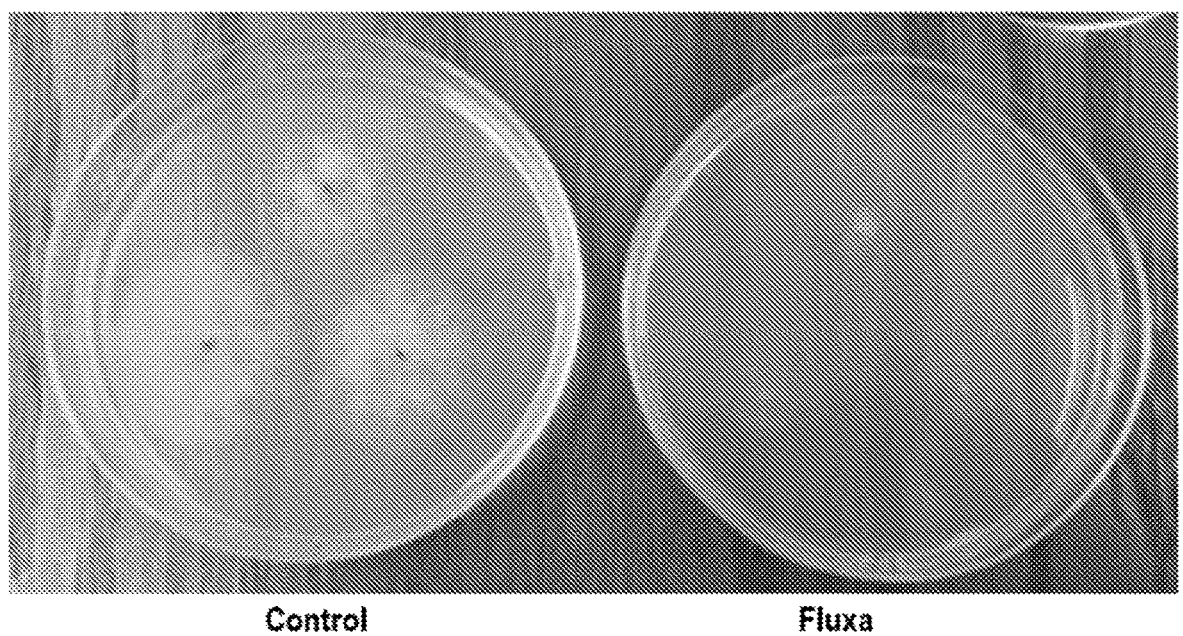
Figure 5:
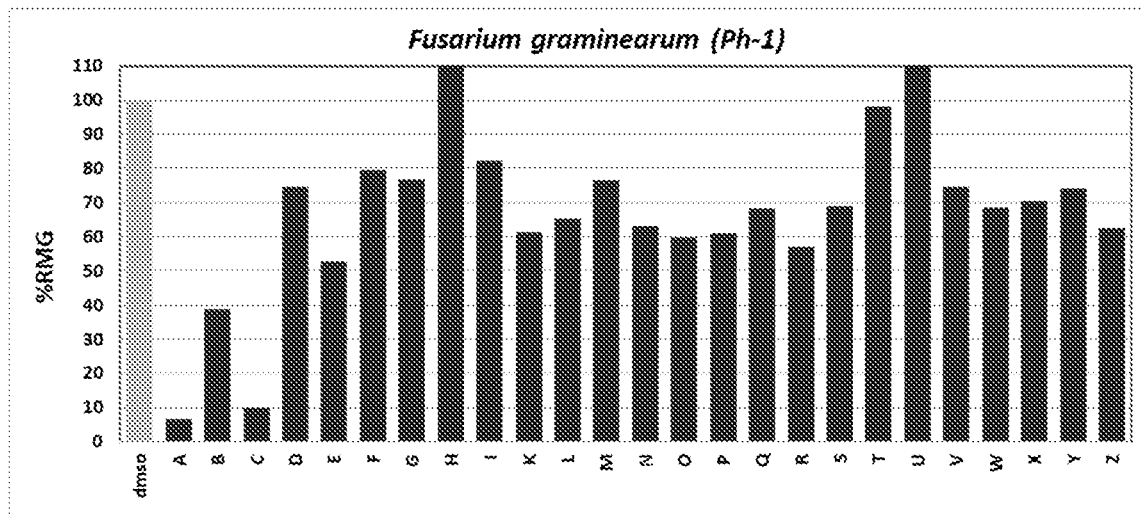
FIG. 5 illustrates the percent radial mycelial growth (% RMG) inhibition of various compounds according to the disclosure against a *Fusarium germinearum* (i.e., ph-1) isolate.
Figure 6:
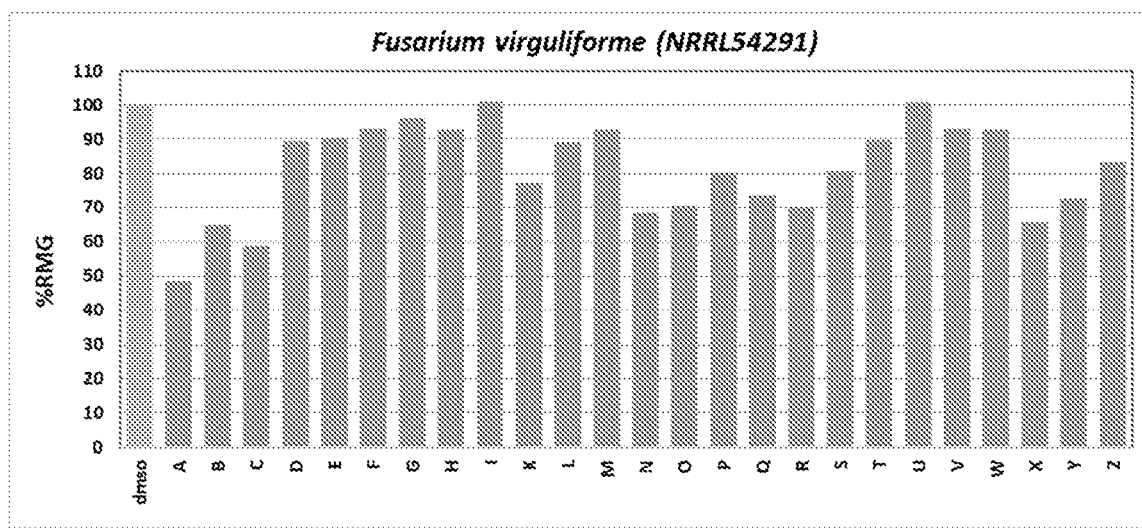
FIG. 6 illustrates the percent radial mycelial growth (% RMG) inhibition of various compounds according to the disclosure against a *Fusarium virguliforme* (i.e., NRRL54291) isolate.
Figure 7:
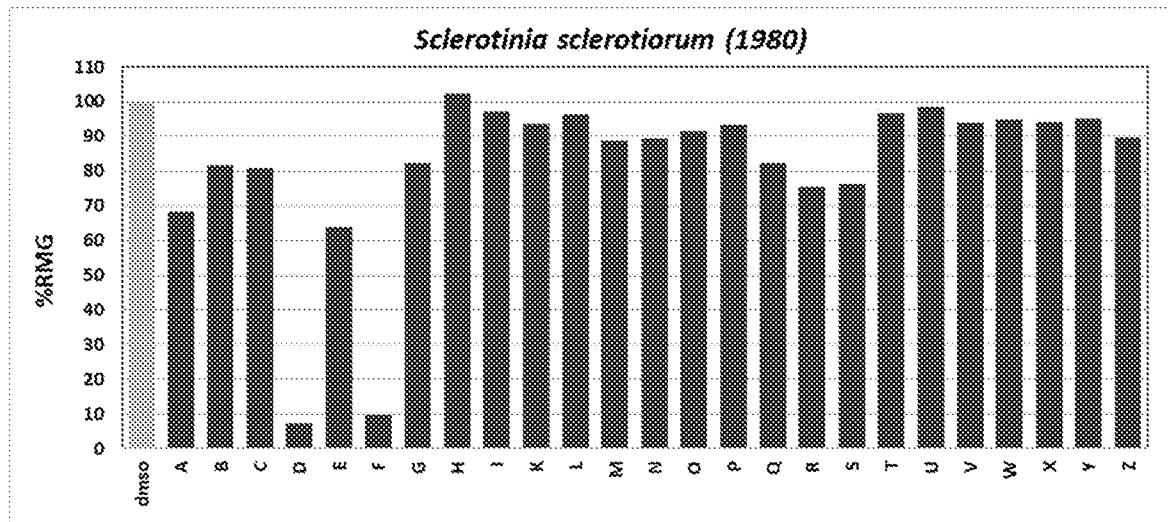
FIG. 7 illustrates the percent radial mycelial growth (% RMG) inhibition of various compounds according to the disclosure against a *Sclerotinia sclerotiorum* (i.e., 1980) isolate.
Figure 8:
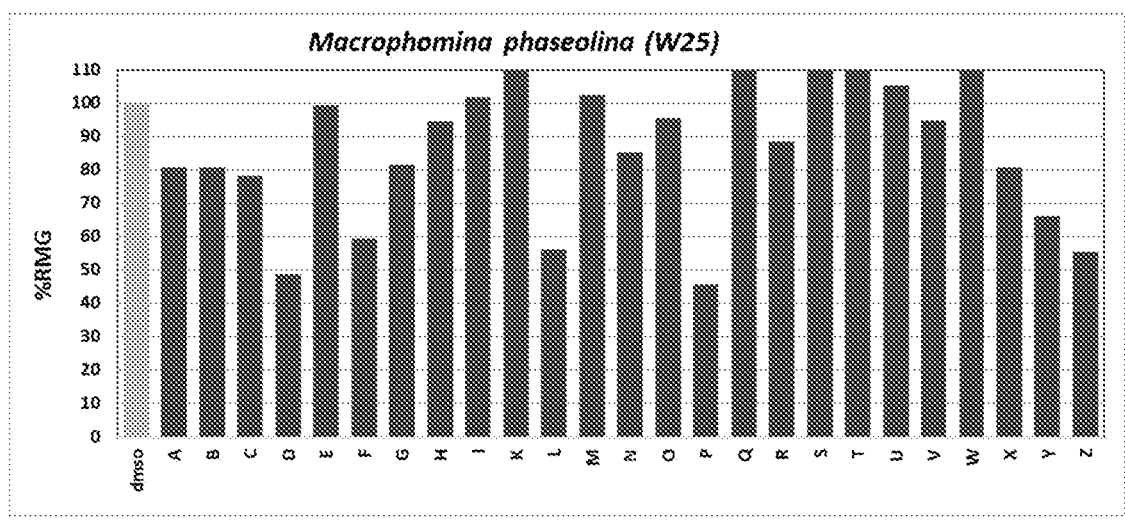
FIG. 8 illustrates the percent radial mycelial growth (% RMG) inhibition of various compounds according to the disclosure against a *Macrophomina phaseolina* (i.e., W25) isolate.

FIGS. 1-4 illustrate the performance of these compounds against the four tested pathogens. Significantly, the brown compound [1831] visibly outperformed the positive control fluxapyroxad, as shown in FIG. 4, where the radial growth for the brown compound reached about half of that seen when the pathogen was treated with fluxapyroxad.

Example 3—SHD Inhibition Assessment of Disclosed Compounds

The following compounds were further evaluated for SDH inhibition. The compound labels are carried throughout this example.

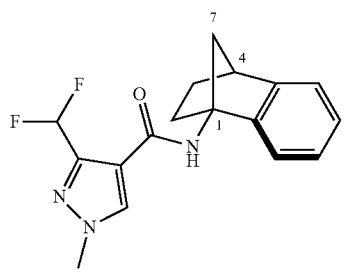

A

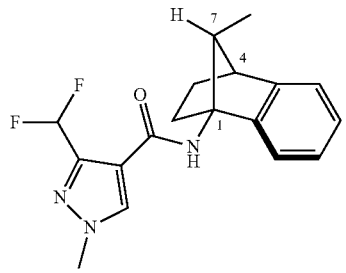

B

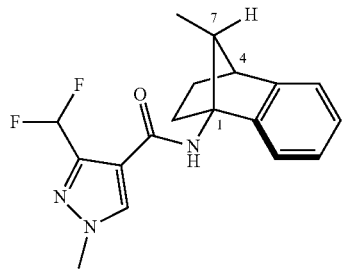

C

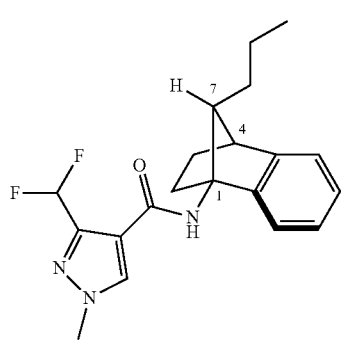

D

E 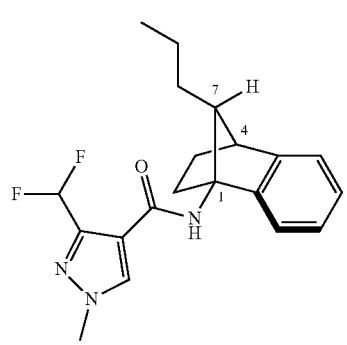
F 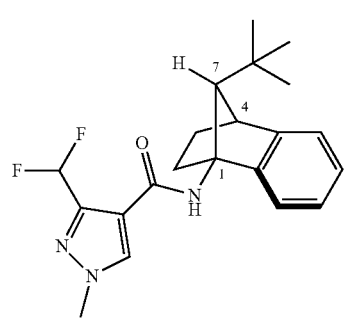
G 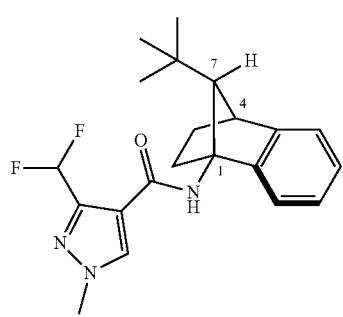
H 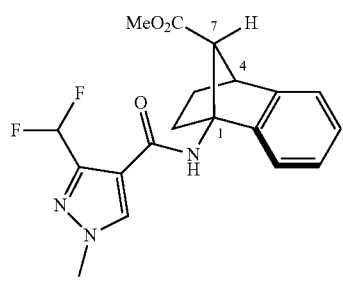
I 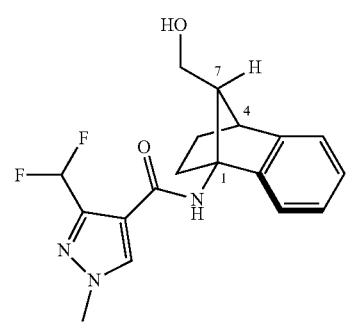
K 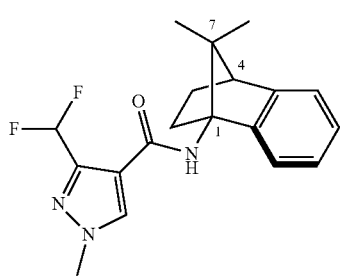
L 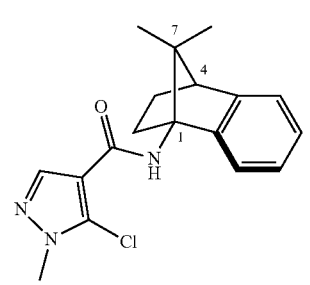
M 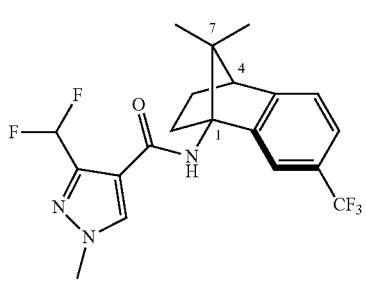
N 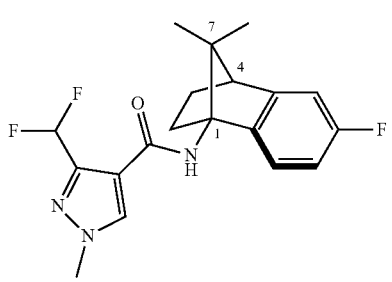
O 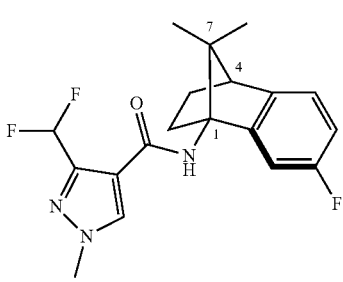

| | |
|---|---|
| 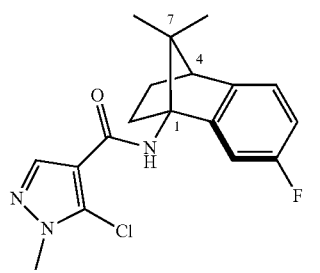 P | 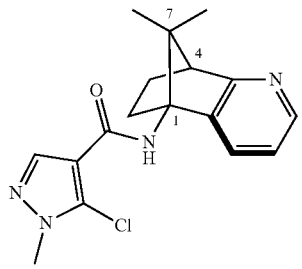 U |
| 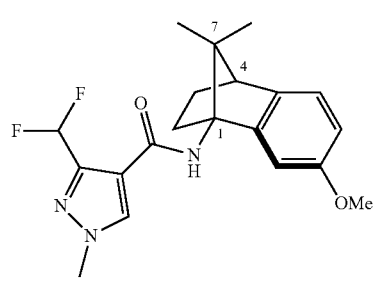 Q | 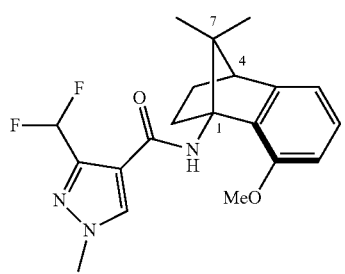 V |
| 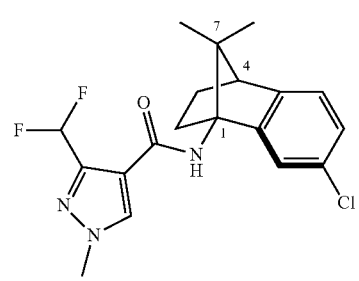 R | 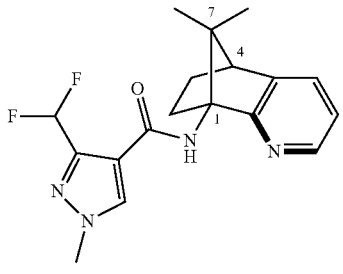 W |
| 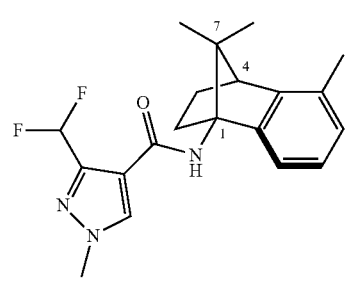 S | 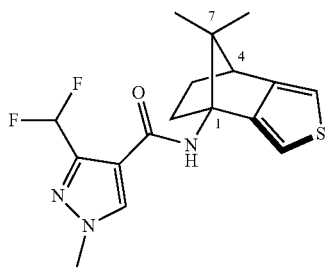 X |
| 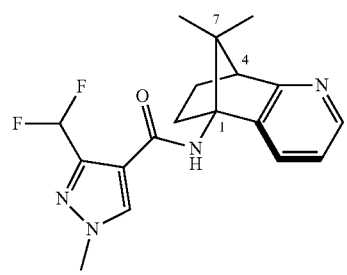 T | 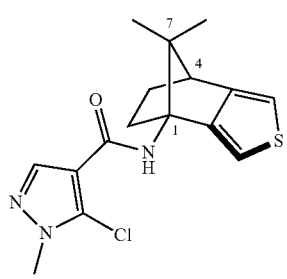 Y |

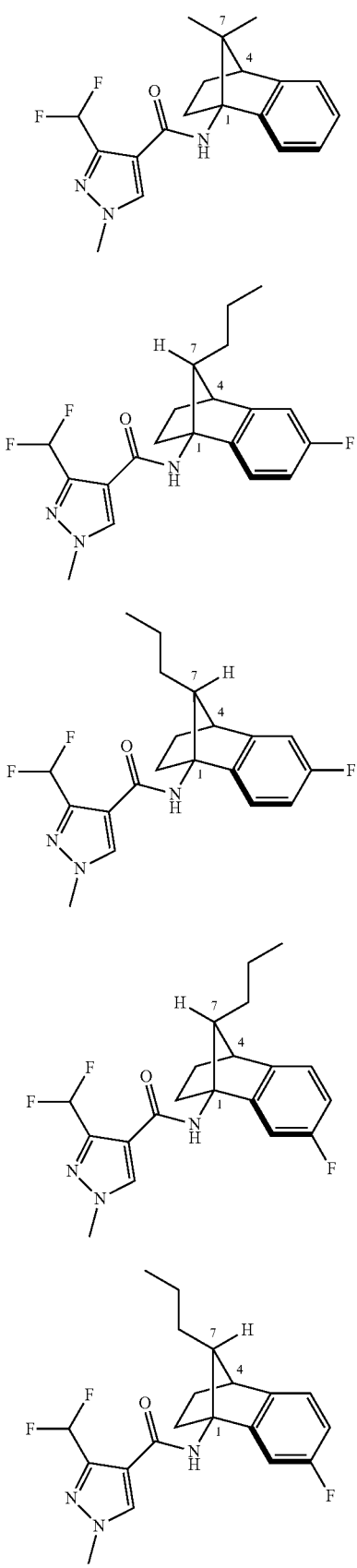

FIGS. 5-8 detail the radial mycelial growth inhibition data for a variety of fungal pathogens. All compounds were dosed at 5-10 ppm in DMSO. Data is presented as percent radial mycelial growth (% RMG), calculated relative to a DMSO control. The data in FIGS. 5-8 show that these compounds were effective in reducing the radial mycelial growth in a variety of fungal pathogens. Of note, commercial SDHIs offer $EC_{50}$ values ranging from 0.5 to 15 ppm against these pathogens, thus all of the tested compound at or near 50% inhibition (i.e. % RMG≤50%) were within an order of magnitude of commercially-relevant activity.

Figures 9, 10:
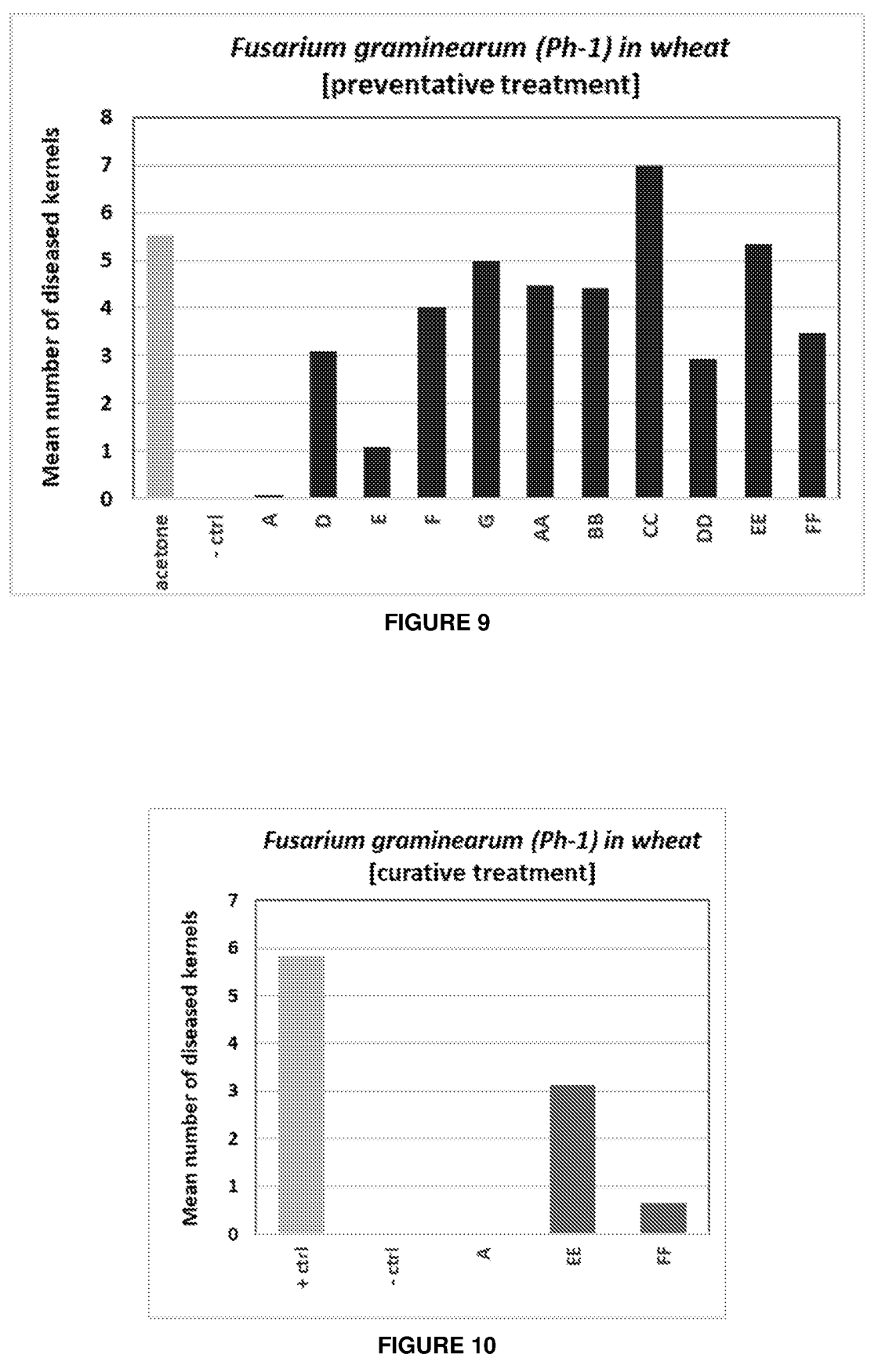

FIGS. 9 and 10 depict the in planta evaluation of selected 1-aminonorbornane-based analogs (i.e., compounds A, D, E, F, G, AA, BB, CC, DD, EE, and FF). The compounds were evaluated in a summer wheat varietal inoculated with *Fusarium graminearum*. Each compound was applied to each head with four 0.15 mL sprays of a 250 ppm solution of the compound in question in acetone, with application occurring approximately 4 hrs prior to inoculation (preventative trial) or 24 hrs after inoculation (curative trial). Data are presented as the average diseased spikelets per plant.

It should be noted that the 250 ppm dosage is approximately 5-fold the field rate dosage of modern commercial agents such as pydiflumetofen (tank concentration for pydiflumetofen is generally 600 ppm, but accounting for application rate and planting density, it calculates to ~0.03 mg/plant; in the assay used herein, the max dose delivered per plant equals 0.15 mg). Significantly, achieving complete or nearly complete control that persisted for 21 days at this dose without any optimization of formulation was highly promising, as many agrochemical companies screen at 10-fold to 100-fold in their initial, un-formulated greenhouse assays. The data suggested that the compounds were either readily taken into the relevant plant tissue or offered highly effective contact kill rates.

Notably, the strong performance in the curative assay (particularly compound A) was significant. SDHIs are typically not expected to offer curative protection (generally reserved for triazoles) with the bulk of commercial applications occurring in a preventative capacity.

We claim:

1. A compound having a structure of Formula (I):

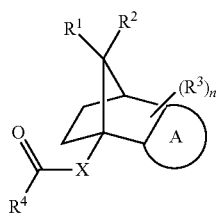

wherein:

X is NH or O;

ring A is $C_{6-10}$ aryl or 5-12 membered heteroaryl having 1-3 ring heteroatoms selected from N, O, and S;

each of $R^1$ and $R^2$ is independently selected from H, halo, $C_{1-18}$ alkyl, $C_{2-18}$ alkenyl, $C_{2-18}$ alkynyl, $C_{1-18}$ alkoxy, $C_{1-18}$ haloalkyl, $C_{1-18}$ hydroxyalkyl, C(O)NHC$_{1-18}$alkyl, C(O)OC$_{1-18}$alkyl, C(O)SC$_{1-18}$alkyl, $C_{2-18}$ heteroalkyl having 1-3 backbone heteroatoms selected from N, O, and S, $C_{6-10}$ aryl, or 5-8 membered heteroaryl having 1-3 ring heteroatoms selected from N, O, and S; or $R^1$ and $R^2$ together form $C_{2-6}$ alkenyl, $C_{3-8}$ cycloalkyl, or $C_{3-8}$ heterocycloalkyl having 1-3 ring heteroatoms selected from N, O, and S, optionally substituted with 1-3 $R^3$ groups;

each $R^3$ is independently halo, CN, OH, $NO_2$, $C_{1-6}$ alkoxy, $C_{1-6}$ alkyl, $C_{1-6}$ hydroxyalkyl, $C_{1-6}$ haloalkyl, or $C_{1-6}$ haloalkylene-OH $R^4$ is $C_{2-6}$ alkyl, $C_{1-6}$ haloalkyl, $C_{1-6}$ heteroalkyl having 1-3 backbone heteroatoms selected from N, O, and S, $C_{3-8}$ cycloalkyl, $C_{6-10}$ aryl, 3-12 membered heterocycloalkyl having 1-3 ring heteroatoms selected from N, O, and S, or 5-12 membered heteroaryl having 1-3 ring heteroatoms selected from N, O, and S, and the aryl or heteroaryl group is optionally substituted with 1-3 $R^3$ groups; and n is 0, 1, 2, or 3;

with the proviso that if ring A is $C_6$ aryl, n is 0, and $R^1$ and $R^2$ are each H, then $R^4$ is not unsubstituted phenyl.

2. The compound of claim 1, wherein ring A is $C_6$ aryl.

3. The compound of claim 1, wherein ring A is a 5-membered heteroaryl having 1 ring S atom or ring A is a 6-membered heteroaryl having 1-2 ring N atoms.

4. The compound of claim 3, wherein ring A comprises pyridyl.

5. The compound of claim 1, wherein $R^4$ is $C_{6-10}$ aryl or 3-8 membered heteroaryl.

6. The compound of claim 1, wherein $R^4$ comprises pyrazolyl.

7. The compound of claim 1, wherein $R^4$ is:

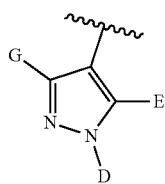

each of G and E is independently H, halo, $C_{1-6}$ alkyl, $C_{1-6}$ hydroxyalkyl, $C_{1-6}$ haloalkylene-OH, or $C_{1-6}$ haloalkyl; and D is H, $C_{1-6}$ alkyl, or $C_{1-6}$ haloalkyl.

8. The compound of claim 7, wherein D is $CH_3$.

9. The compound of claim 7, wherein G is H, $CHF_2$, or $CF_3$.

10. The compound of claim 7, wherein E is H, Cl, $CHF_2$, $CF_3$, or $CF_2CH_2OH$.

11. The compound of claim 1, wherein $R^4$ is

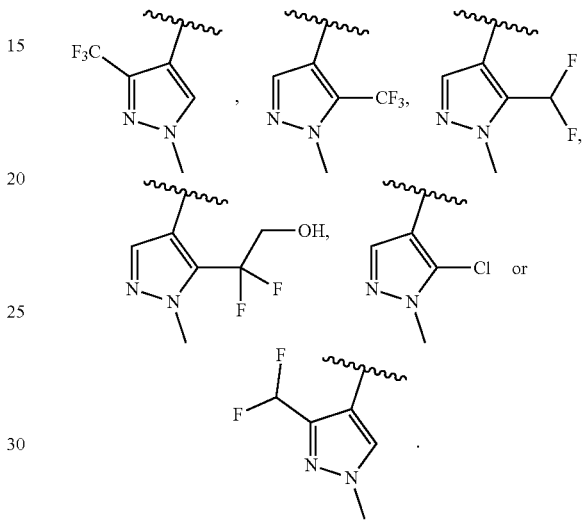

12. The compound of claim 1, wherein at least one of $R^1$ and $R^2$ is $C_{1-6}$ alkyl.

13. The compound of claim 1, having a structure selected from the group consisting of:

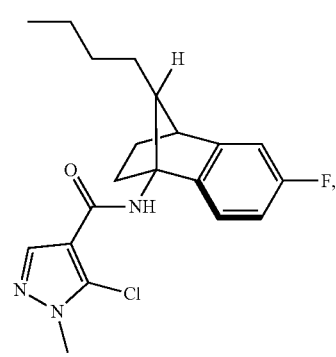

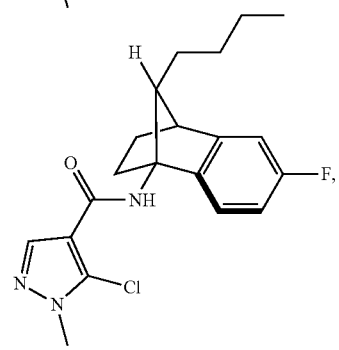

85
-continued
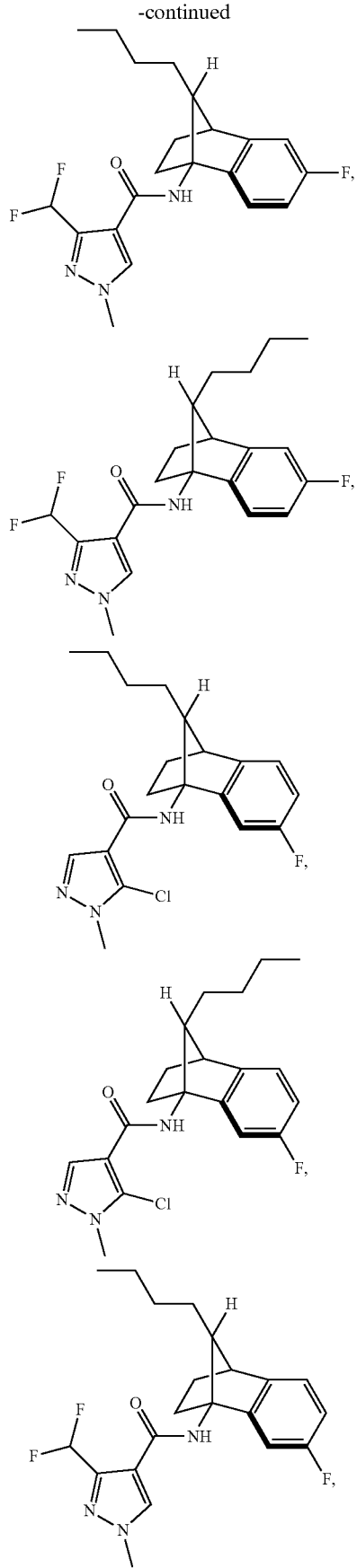
86
-continued
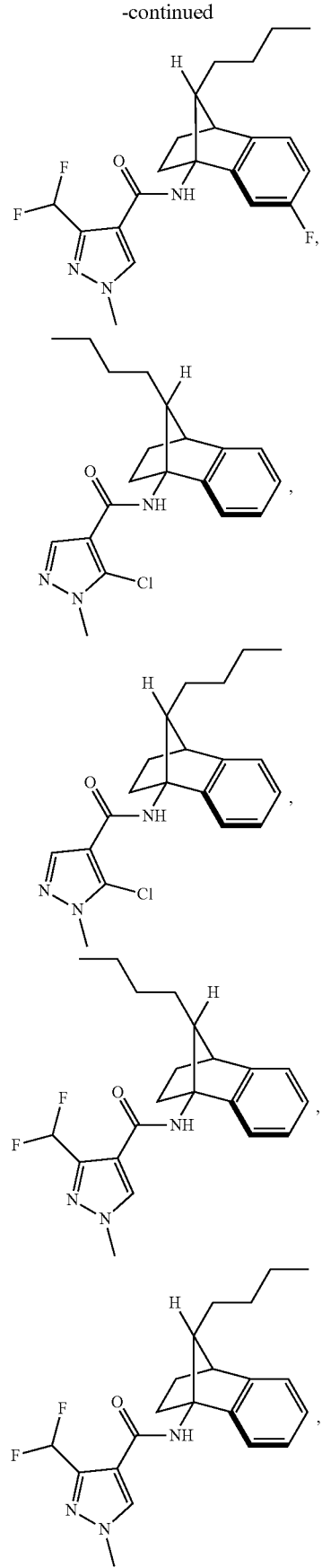

87
-continued
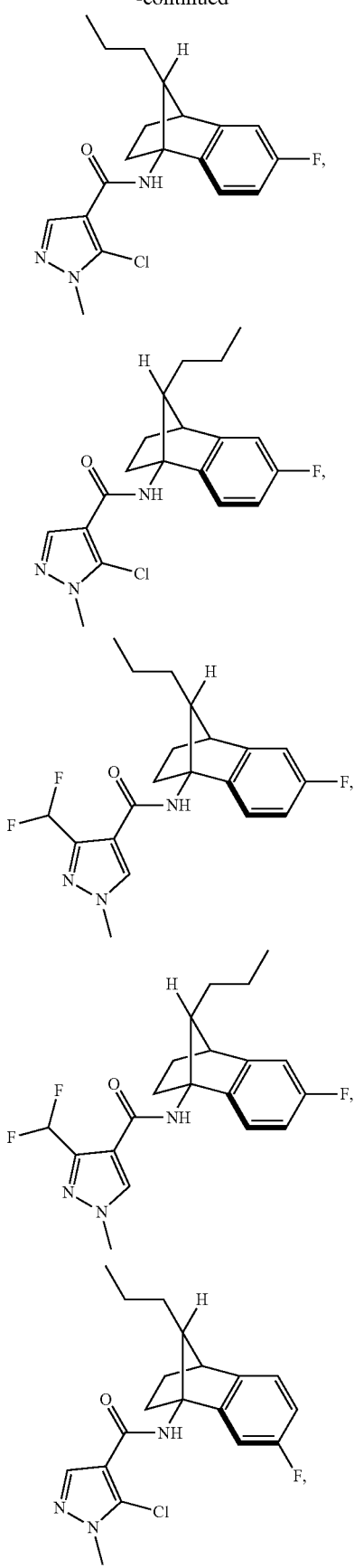
88
-continued
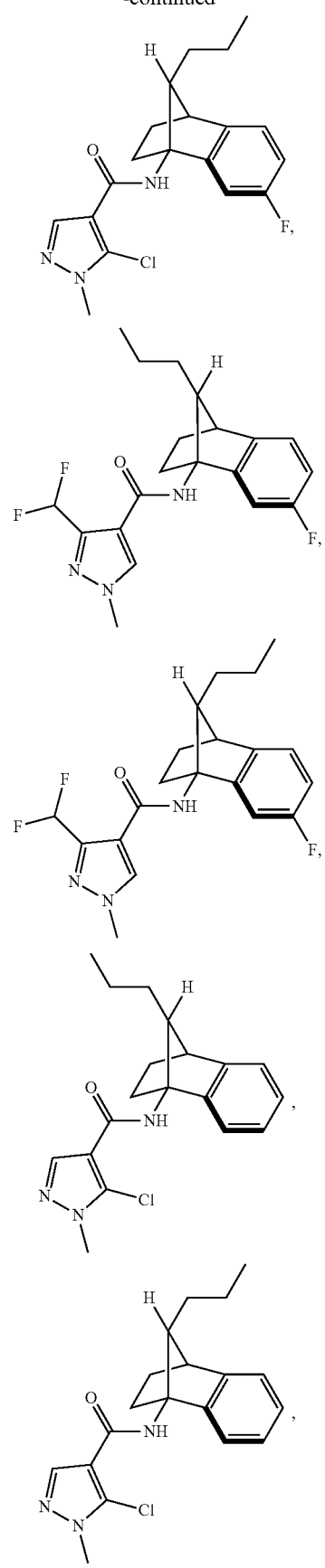

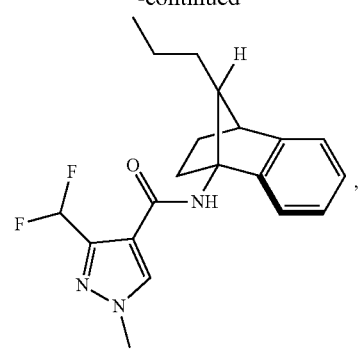
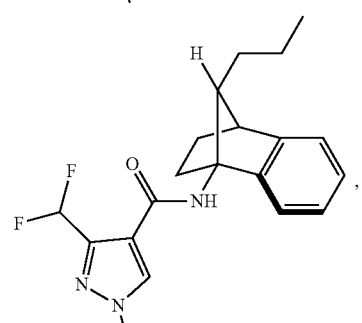
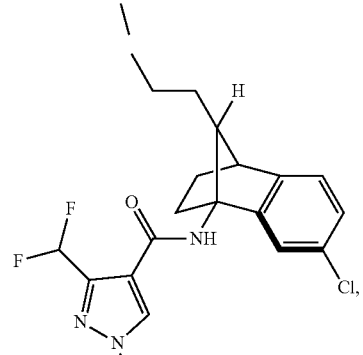
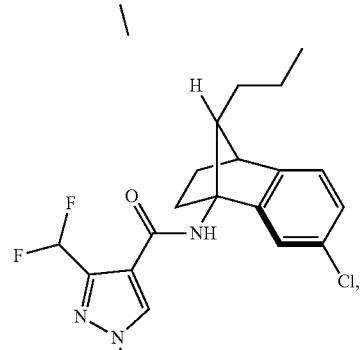
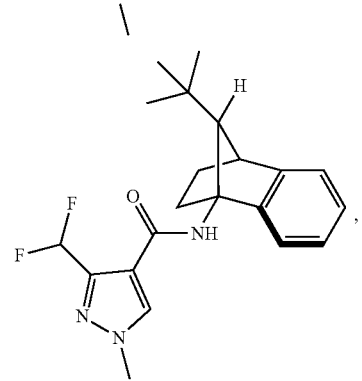
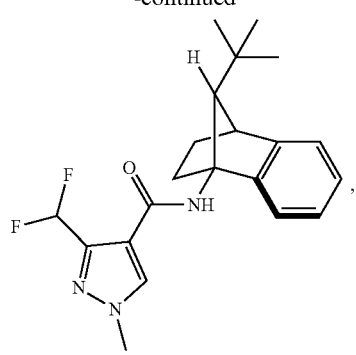
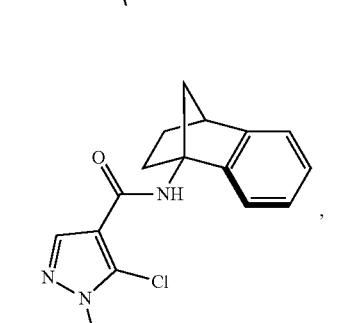
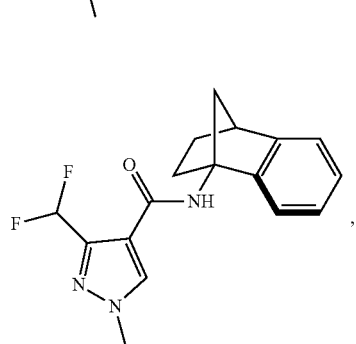
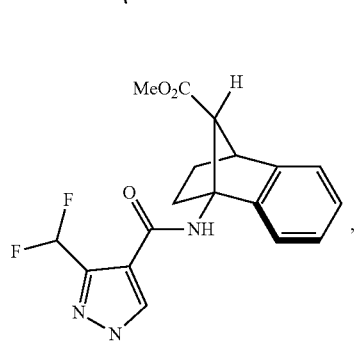
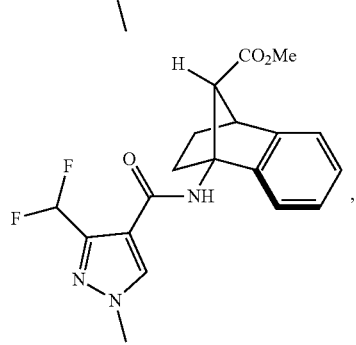

91
-continued
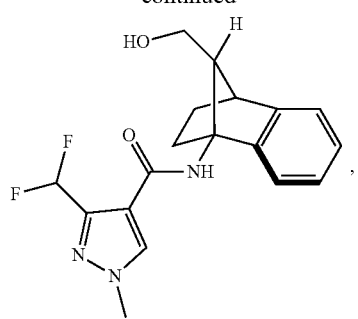,
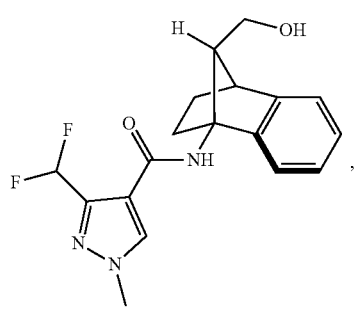,
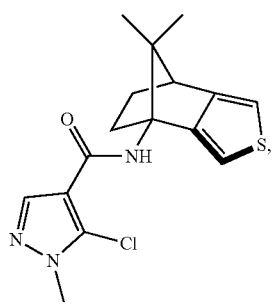,
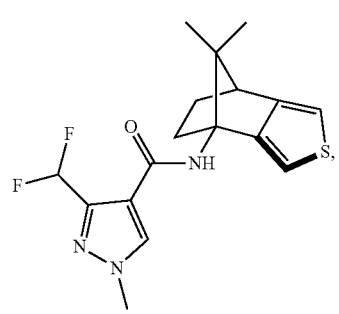,
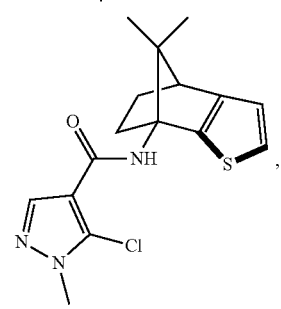,
92
-continued
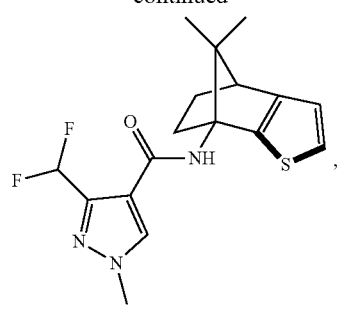,
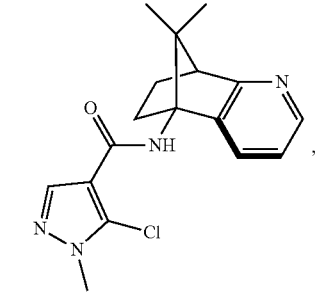,
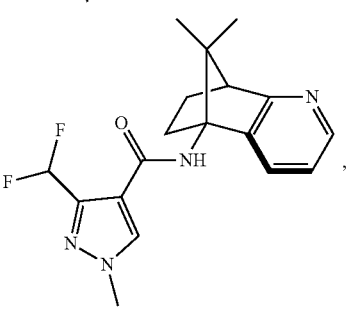,
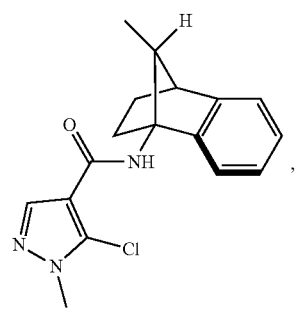,
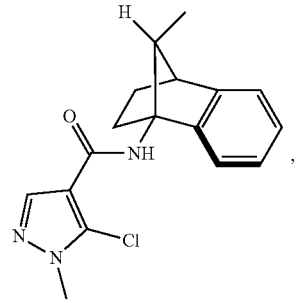,

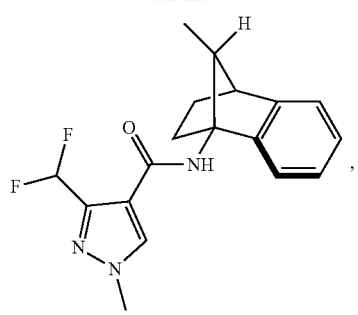
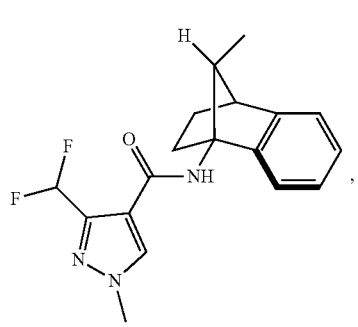
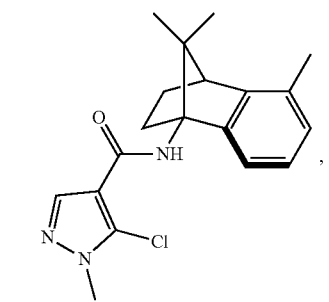
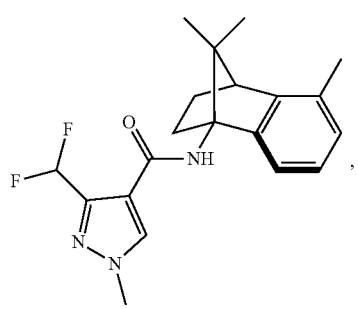
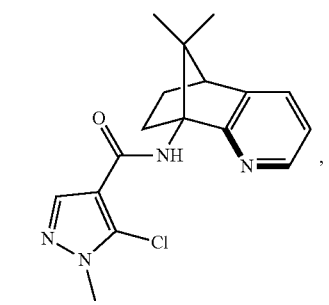
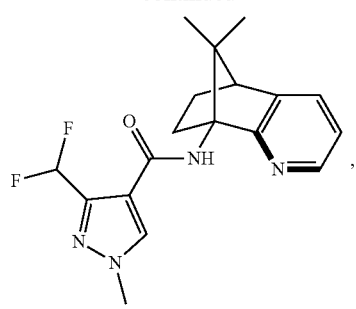
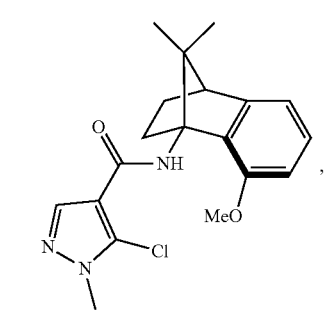
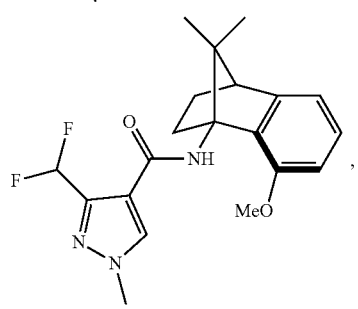
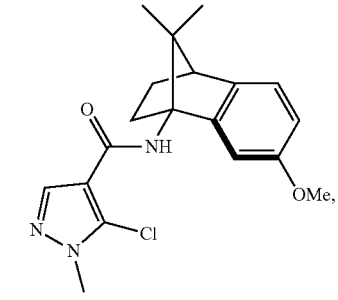
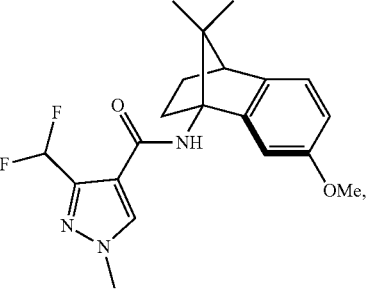

95
-continued
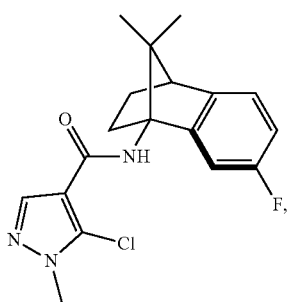
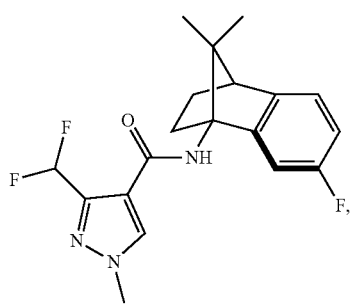
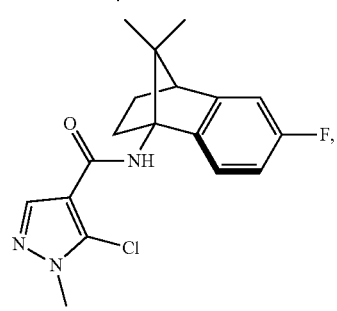
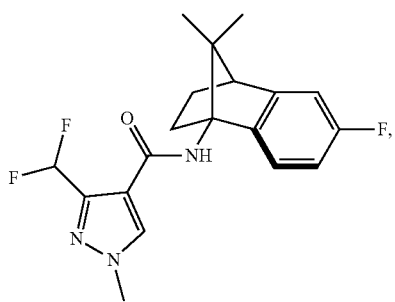
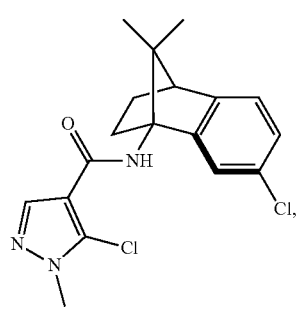
96
-continued
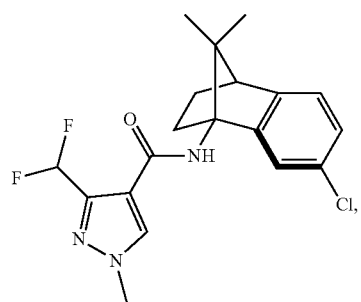
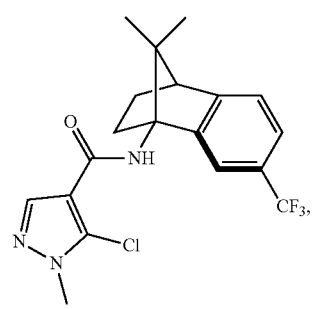
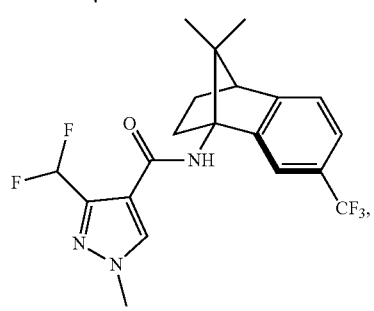
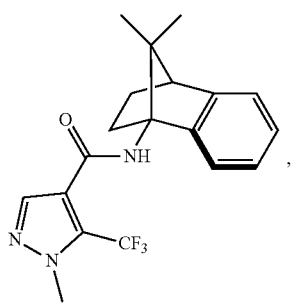
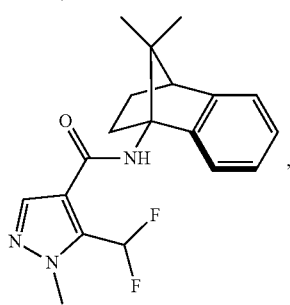

97
-continued
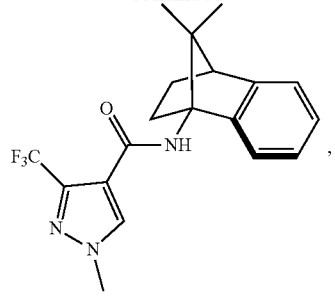
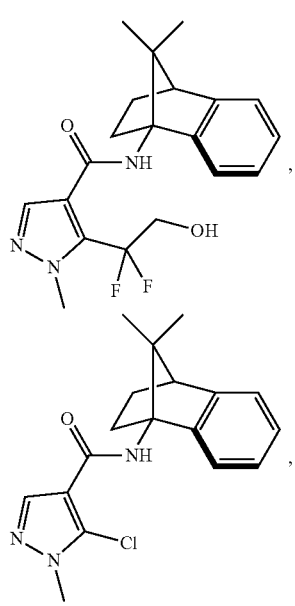
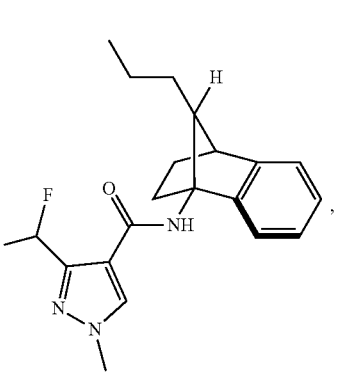
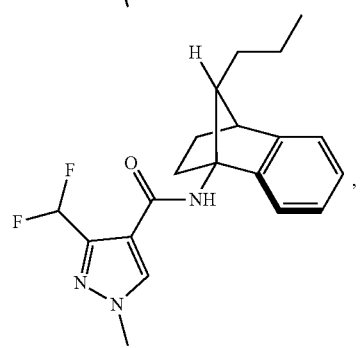
98
-continued
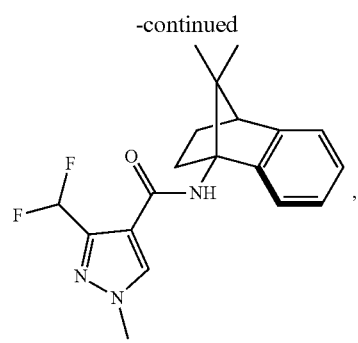
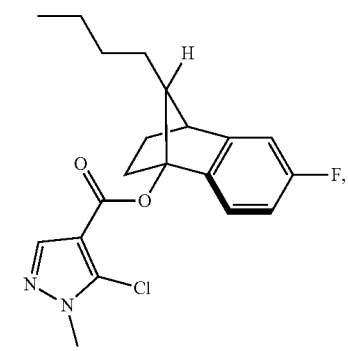
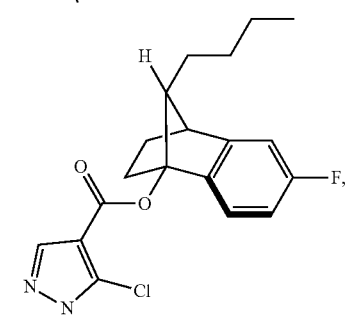
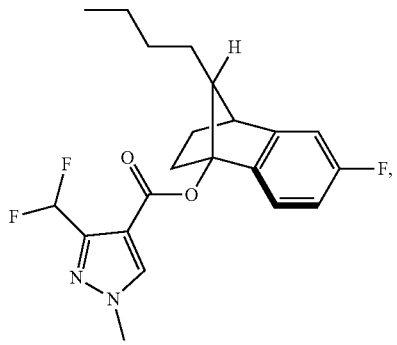
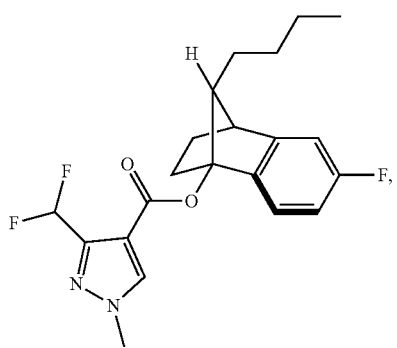

99
-continued
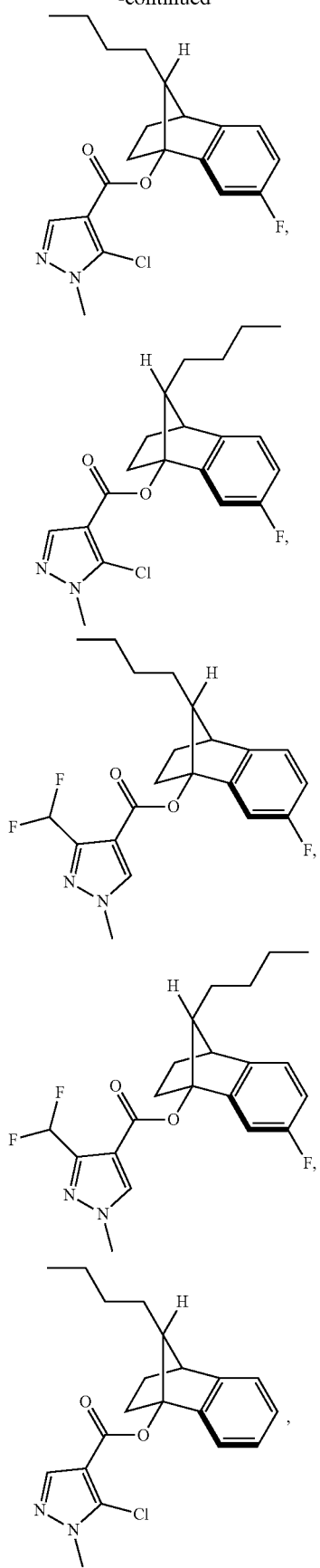
100
-continued
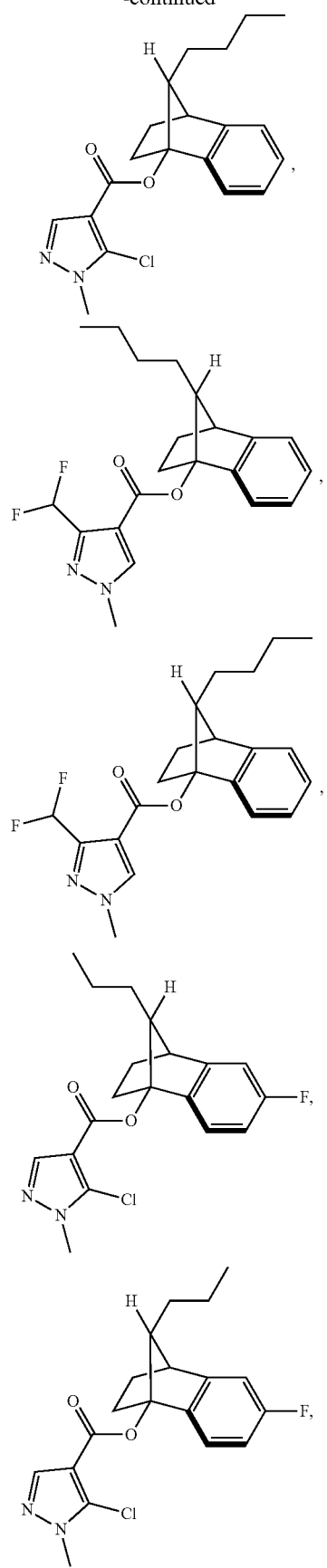

101
-continued
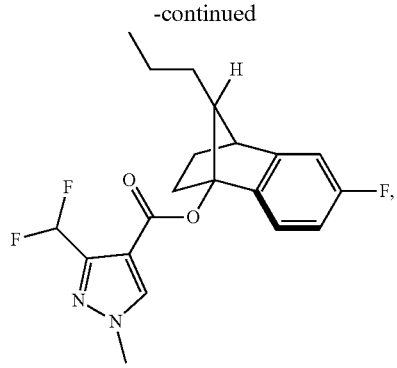
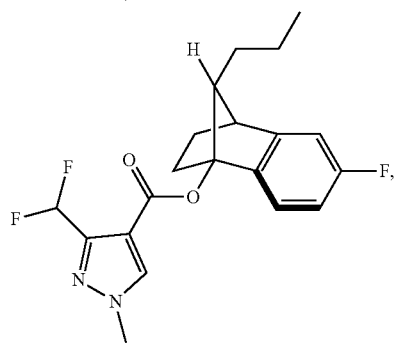
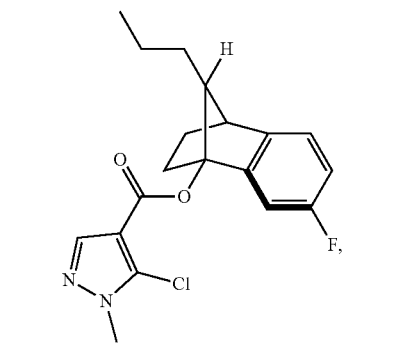
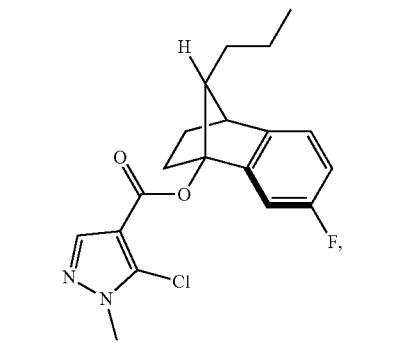
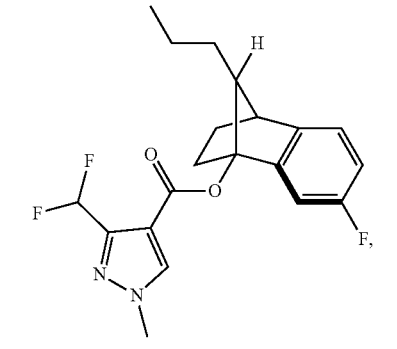
102
-continued
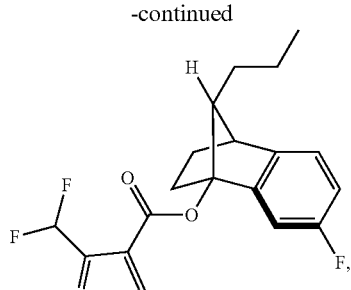
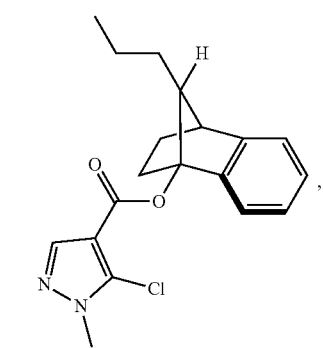
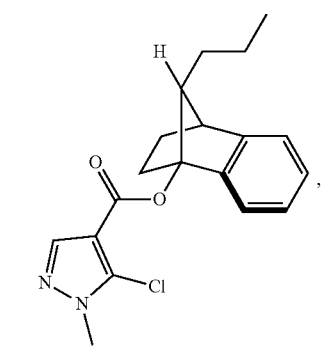
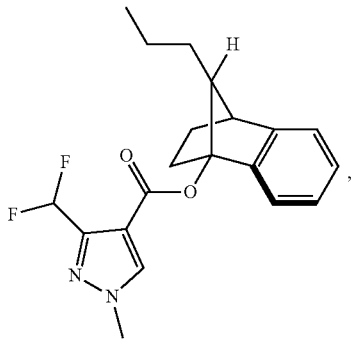
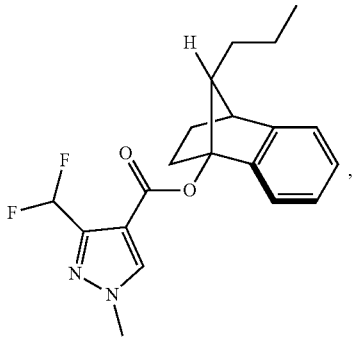

103
-continued
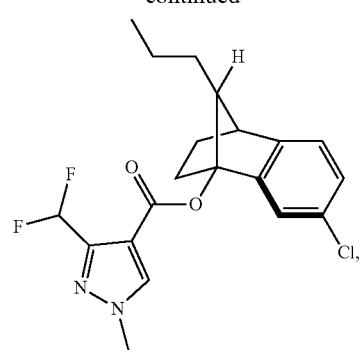
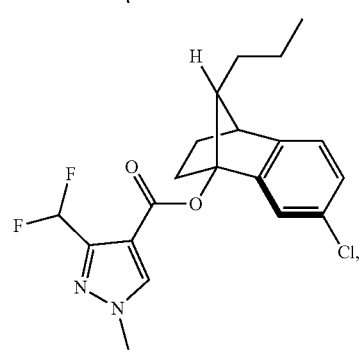
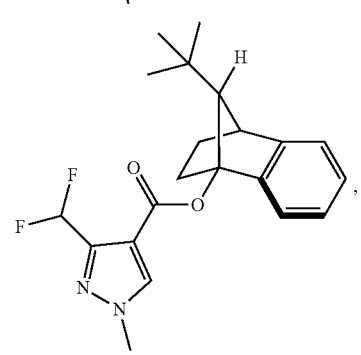
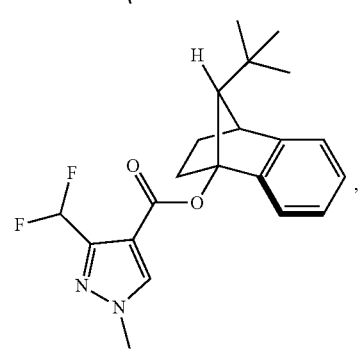
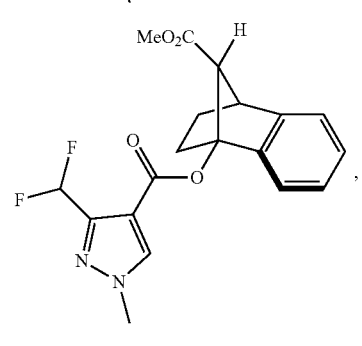
104
-continued
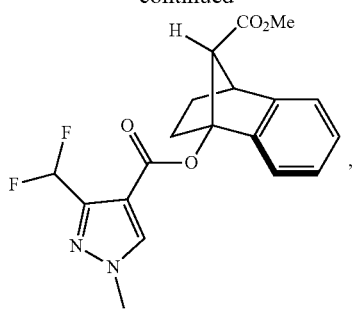
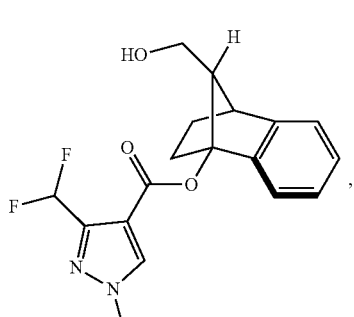
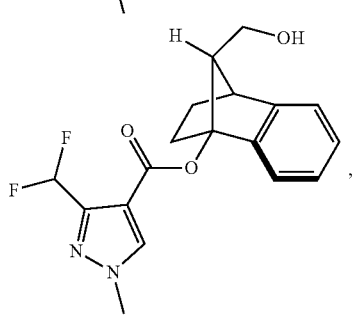
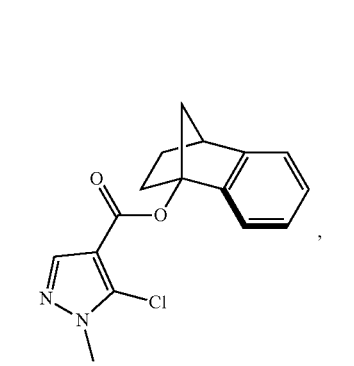
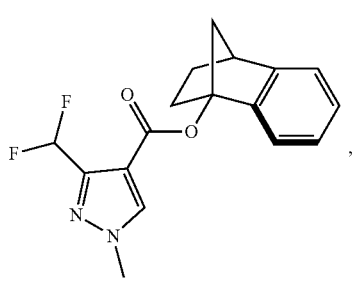

105
-continued
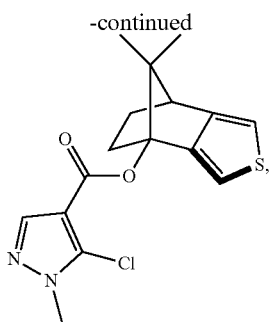
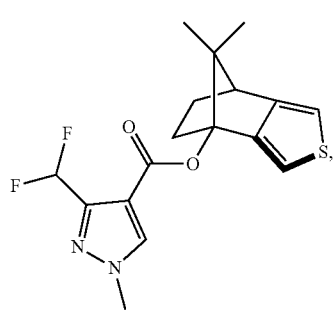
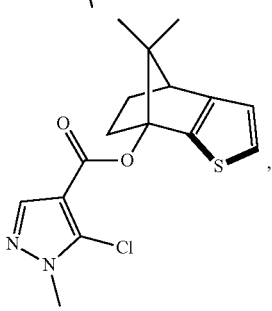
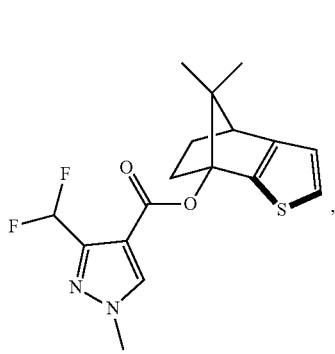
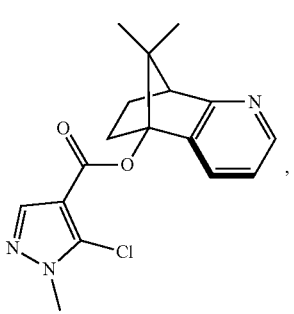
106
-continued
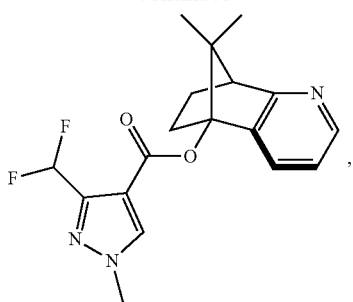
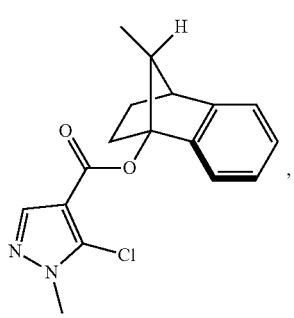
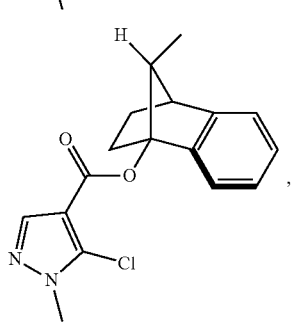
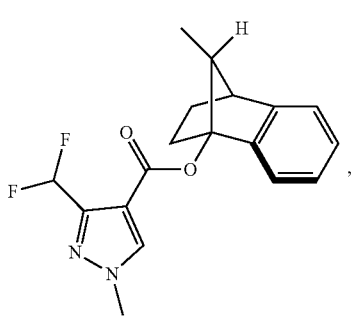
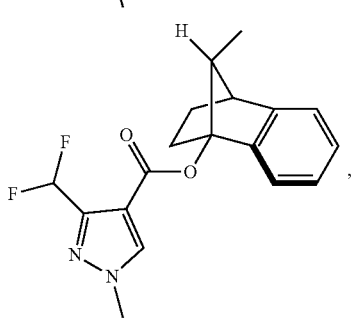

107
-continued
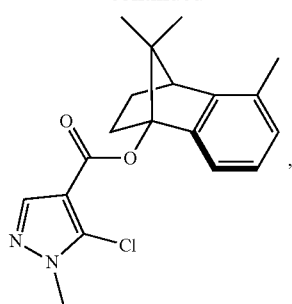
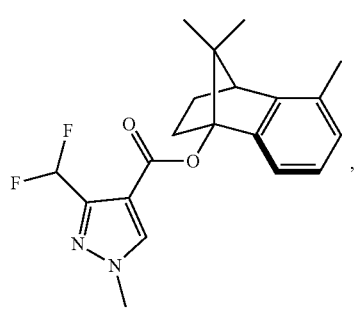
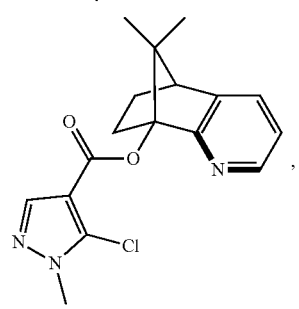
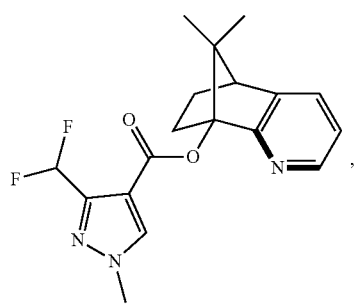
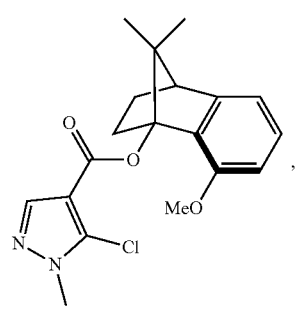
108
-continued
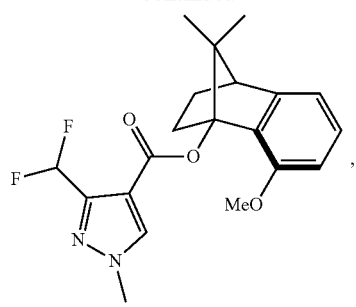
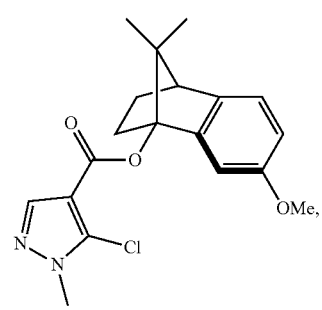
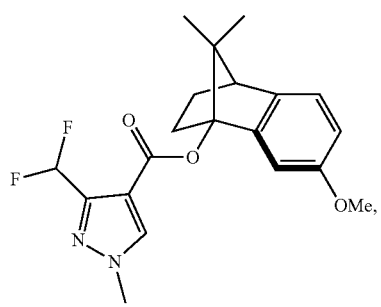
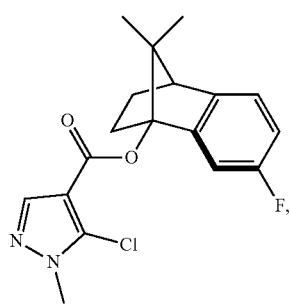
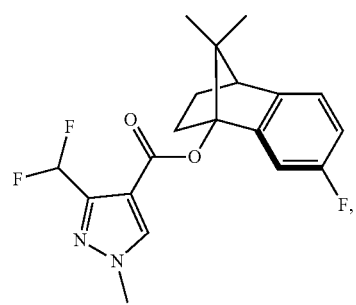

109
-continued
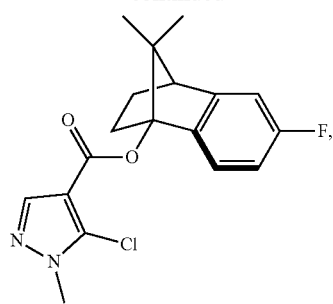
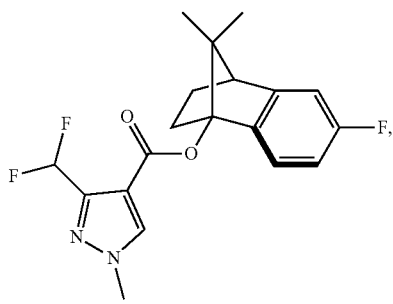
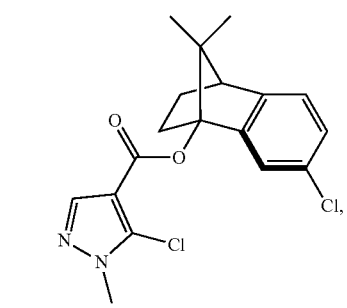
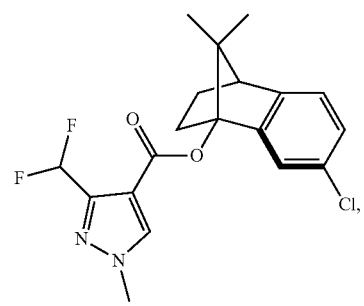
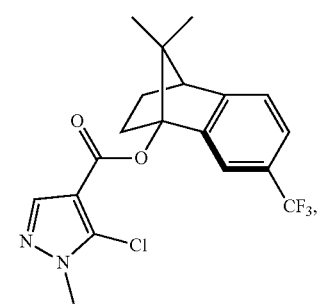
110
-continued
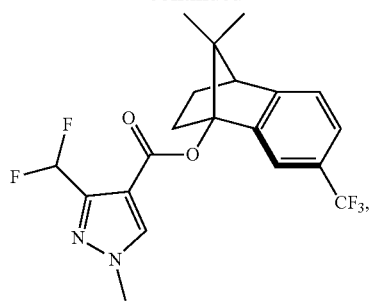
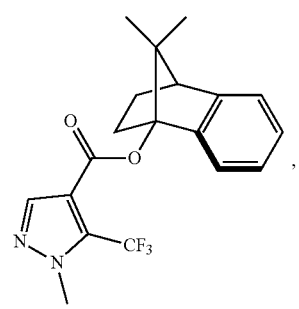
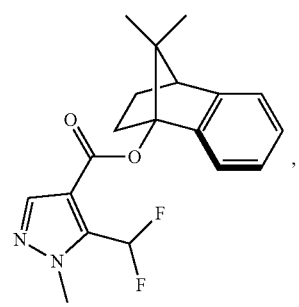
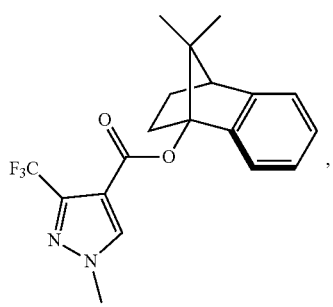
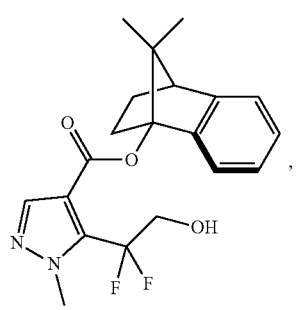

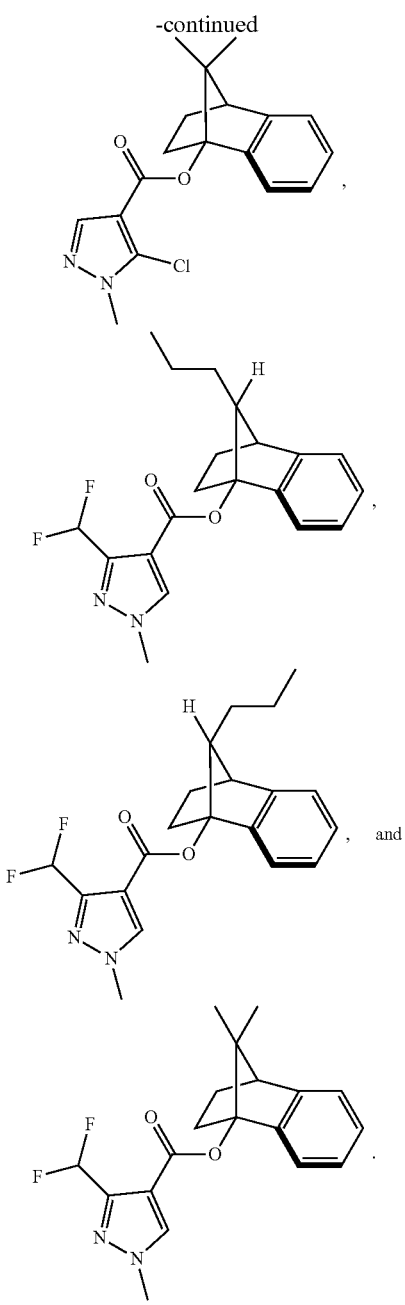, 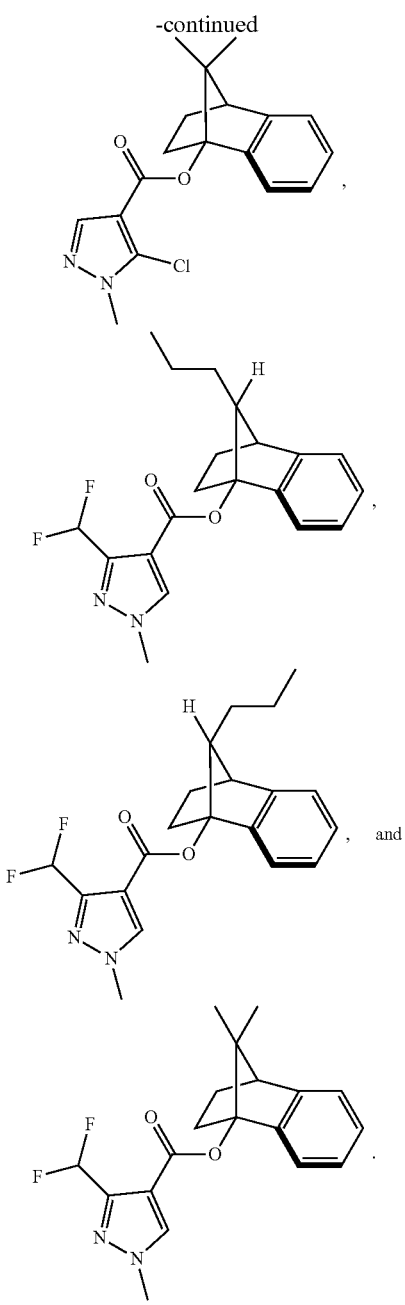, and .

14. A formulation comprising the compound of claim 1 and a carrier.

15. A method of inhibiting or preventing fungal growth on a plant, comprising applying to the plant the compound of claim 1.

16. The method of claim 15, wherein the compound is applied to one or more of an area adjacent to the plant, soil adapted to support growth of the plant, a root of the plant, foliage of the plant, and a seed adapted to produce the plant.

17. The method of claim 15, wherein the fungus is selected from the group consisting of *Sclerotinia*, *Fusarium*, *Macrophomina*, *Monilinia*, *Mycosphaerella*, *Puccinia*, *Microdochium*, *Blumeria*, *Pyrenophora*, *Rhynchosporium*, *Ramularia*, *Botrytis*, *Erysiphe*, *Venturia*, *Podosphaera*, *Sphaerotheca*, *Golovinomyces*, *Alternaria*, *Leptosphaeria*, *Helminthosporium*, *Rhizoctonia*, *Oidium*, *Phakopsora*, *Corynespora*, *Ustilago*, *Aspergillus*, *Zymoseptoria*, *Pyrenophora*, *Didymella*, *Stemphylium*, *Erysiphe*, *Coprinus*, *Blumeriella*, *Pythium*, *Phytophthora*, *Septoria*, *Penicillium*, and *Cerospora*.

18. A method of preparing the compound of claim 1 comprising irradiating a compound of formula (II) to form an intermediate of formula (III):

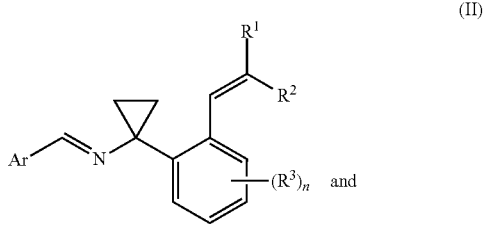

(II)

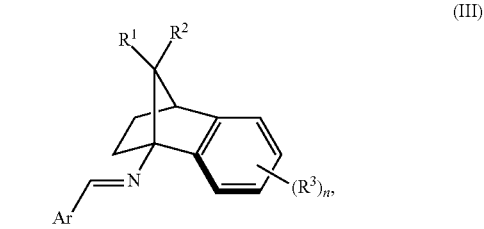

(III)

wherein Ar comprises a $C_6$ aryl; and hydrolyzing the intermediate of Formula (III) to form an amine and acylating the resulting amine to form the compound having a structure of Formula (I); or hydrolyzing the intermediate of Formula (III) to form an amine, converting the resulting amine to an alcohol, and acylating the resulting alcohol to form the compound having a structure of Formula (I); or solvolyzing the intermediate of Formula (III) to form an amine, and reacting the amine with an acyl reagent having a structure

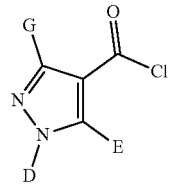

to form the compound of Formula (I).

19. The method of claim 18, wherein Ar comprises nitro-phenyl.

* * * * *